US011426367B2

(12) United States Patent
Witkin et al.

(10) Patent No.: US 11,426,367 B2
(45) Date of Patent: Aug. 30, 2022

(54) METHODS OF TREATING SUBSTANCE ABUSE

(71) Applicant: Perception Neuroscience, Inc., New York, NY (US)

(72) Inventors: Jeffrey M. Witkin, New York, NY (US); Jonathan Sporn, New York, NY (US); Jay D. Kranzler, New York, NY (US)

(73) Assignee: Perception Neuroscience, Inc., New York, NY (US)

( * ) Notice: Subject to any disclaimer, the term of this patent is extended or adjusted under 35 U.S.C. 154(b) by 0 days.

(21) Appl. No.: 17/052,622

(22) PCT Filed: May 3, 2019

(86) PCT No.: PCT/US2019/030644
§ 371 (c)(1),
(2) Date: Nov. 3, 2020

(87) PCT Pub. No.: WO2019/213551
PCT Pub. Date: Nov. 7, 2019

(65) Prior Publication Data
US 2021/0259993 A1  Aug. 26, 2021

Related U.S. Application Data

(60) Provisional application No. 62/666,813, filed on May 4, 2018.

(51) Int. Cl.
| A61P 25/32 | (2006.01) |
| A61K 31/135 | (2006.01) |
| A61P 25/36 | (2006.01) |
| A61P 25/22 | (2006.01) |
| A61P 25/24 | (2006.01) |
| A61K 45/06 | (2006.01) |

(52) U.S. Cl.
CPC ............ *A61K 31/135* (2013.01); *A61K 45/06* (2013.01); *A61P 25/22* (2018.01); *A61P 25/24* (2018.01); *A61P 25/32* (2018.01); *A61P 25/36* (2018.01)

(58) Field of Classification Search
CPC ... A61K 31/135; A61P 25/30–36; A61P 25/32
See application file for complete search history.

(56) References Cited

U.S. PATENT DOCUMENTS

| 3,254,124 | A | 5/1966 | Stevens |
| 4,670,459 | A | 6/1987 | Sjoerdsma |
| 5,543,434 | A | 8/1996 | Weg |
| 5,679,714 | A | 10/1997 | Weg |
| 5,989,582 | A | 11/1999 | Weg |
| 6,040,479 | A | 3/2000 | Steiner et al. |
| 6,248,789 | B1 | 6/2001 | Weg |
| 6,743,949 | B2 | 6/2004 | Russo et al. |
| 6,962,151 | B1 | 11/2005 | Knoch et al. |
| 7,001,609 | B1 | 2/2006 | Matson et al. |
| 7,044,125 | B2 | 5/2006 | Vedrine et al. |
| 7,090,830 | B2 | 8/2006 | Hale et al. |
| 7,273,889 | B2 | 9/2007 | Mermelstein et al. |
| 7,713,440 | B2 | 5/2010 | Anderson |
| 7,973,043 | B2 | 7/2011 | Migaly |
| 8,785,500 | B2 | 7/2014 | Charney et al. |
| 9,539,220 | B2 | 1/2017 | Charney et al. |
| 9,592,207 | B2 | 3/2017 | Charney et al. |
| 9,610,259 | B2 | 4/2017 | Erickson et al. |
| 9,872,841 | B2 | 1/2018 | Hashimoto |
| 9,918,993 | B2 | 3/2018 | Berdahl et al. |
| 10,232,117 | B2 | 3/2019 | Halseth |
| 10,252,982 | B2 | 4/2019 | Nivorozhkin et al. |
| 10,406,121 | B2 | 9/2019 | Hashimoto |
| 10,441,544 | B2 | 10/2019 | Glue et al. |
| 10,478,405 | B2 | 11/2019 | Charney et al. |
| 10,683,262 | B2 | 6/2020 | Xiang et al. |
| 10,744,094 | B2 | 8/2020 | Glue et al. |
| 10,815,196 | B2 | 10/2020 | Chen et al. |
| 10,869,838 | B2 | 12/2020 | Glue et al. |
| 10,881,665 | B2 | 1/2021 | Javitt |
| 10,973,780 | B2 | 4/2021 | Becker et al. |
| 11,007,200 | B2 | 5/2021 | Godek et al. |
| 11,045,424 | B2 | 6/2021 | Glue et al. |
| 11,103,499 | B2 | 8/2021 | Vepachedu et al. |

(Continued)

FOREIGN PATENT DOCUMENTS

| DE | 2062 620 A1 | 7/1971 |
| GB | 1 330 878 A | 9/1973 |

(Continued)

OTHER PUBLICATIONS

Carroll et al., "Behavioral therapies for drug abuse," Am. J. Psychiatry Aug. 2005; 162(8):1452-60. PMID: 16055766. (Year: 2005).*
Abbott, A. & Dolgin, E., "Leading Alzheimer's theory survives drug failure," Nature, 540(7631):15-16 (2016).
Abi-Saab, W. M. et al., "The NMDA Antagonist Model for Schizophrenia: Promise and Pitfalls," Pharmacopsychiat. 31(Suppl):104-109 (1998).
Ashry, E. E. et al., "Protective Effect of Ketamine against Acetic Acid-Induced Ulcerative Colitis in Rats," Pharmacology & Pharmacy, 7:9-18 (2016).
Barch, D. M. & Ceaser, A., "Cognition in schizophrenia: core psychological and neural mechanisms," Trends in Cognitive Sciences, 16(1):27-34 (2012).
Bell, D. S., "The Motivation of Addiction," Acta Neurochir (Wien), 132:185-191 (1995).
Berman, R. M. et al., "Antidepressant Effects of Ketamine in Depressed Patients," Biological Psychiatry, 47:351-354 (2000).

(Continued)

*Primary Examiner* — Theodore R. Howell
(74) *Attorney, Agent, or Firm* — Cooley LLP; Ivor R. Elrifi; Matthew Pavao

(57) ABSTRACT

The disclosure provides a method of treating a substance use disorder in a subject, comprising administering to the subject a therapeutically effective amount of a composition comprising R(−)-ketamine or a pharmaceutically acceptable salt thereof, wherein the composition is substantially free of S(+)-ketamine or a pharmaceutically acceptable salt thereof.

19 Claims, 23 Drawing Sheets

(56) References Cited

U.S. PATENT DOCUMENTS

| | | |
|---|---|---|
| 11,191,734 B2 | 12/2021 | Tang et al. |
| 11,207,279 B2 | 12/2021 | Hashimoto |
| 11,253,487 B2 | 2/2022 | Kagan et al. |
| 11,286,230 B2 | 3/2022 | Toupy et al. |
| 2004/0248964 A1 | 12/2004 | Crooks et al. |
| 2012/0225949 A1 | 9/2012 | Papalos |
| 2013/0236573 A1 | 9/2013 | Singh et al. |
| 2014/0057988 A1 | 2/2014 | Weg |
| 2014/0093592 A1 | 4/2014 | Singh et al. |
| 2014/0274981 A1 | 9/2014 | Basstanie et al. |
| 2014/0275276 A1 | 9/2014 | Basstanie et al. |
| 2014/0275277 A1 | 9/2014 | Basstanie et al. |
| 2014/0275278 A1 | 9/2014 | Basstanie et al. |
| 2015/0056308 A1 | 2/2015 | Charney et al. |
| 2015/0196501 A1 | 7/2015 | Erickson et al. |
| 2016/0045455 A1 | 2/2016 | Revets et al. |
| 2016/0067196 A1 | 3/2016 | Charney et al. |
| 2016/0175266 A1 | 6/2016 | Mermelstein et al. |
| 2016/0220513 A1* | 8/2016 | Hashimoto ............ A61P 25/22 |
| 2019/0060254 A1 | 2/2019 | Sherman et al. |
| 2019/0083420 A1 | 3/2019 | Wainer et al. |
| 2019/0117591 A1 | 4/2019 | Basstanie et al. |
| 2019/0343781 A1 | 11/2019 | Hashimoto |
| 2019/0350879 A1 | 11/2019 | Jay |
| 2020/0000748 A1 | 1/2020 | Kagan et al. |
| 2020/0069674 A1 | 3/2020 | Vepachedu et al. |
| 2020/0121619 A1 | 4/2020 | Rey |
| 2020/0147005 A1 | 5/2020 | Kagan et al. |
| 2020/0261442 A1 | 8/2020 | Vepachedu |
| 2020/0297734 A1 | 9/2020 | Saadeh |
| 2020/0360307 A1 | 11/2020 | Denny et al. |
| 2020/0360308 A1 | 11/2020 | Becker et al. |
| 2020/0405663 A1 | 12/2020 | Hashimoto |
| 2021/0000762 A1 | 1/2021 | Hashimoto |
| 2021/0032194 A1 | 2/2021 | Kandula |
| 2021/0196654 A1 | 7/2021 | Gershon et al. |
| 2021/0251969 A1 | 8/2021 | Abdallah et al. |
| 2021/0378989 A1 | 12/2021 | Kagan |
| 2022/0041540 A1 | 2/2022 | Kruegel |
| 2022/0071929 A1 | 3/2022 | Hashimoto |
| 2022/0119338 A1 | 4/2022 | Lin et al. |
| 2022/0151955 A1 | 5/2022 | Wolfson et al. |

FOREIGN PATENT DOCUMENTS

| | | |
|---|---|---|
| JP | 4401613 B2 | 1/2010 |
| WO | WO 01/062932 A1 | 8/2001 |
| WO | WO 01/098265 A2 | 12/2001 |
| WO | WO 2004/028522 A1 | 4/2004 |
| WO | WO 2007/038949 A1 | 4/2007 |
| WO | WO 2007/111880 A2 | 10/2007 |
| WO | WO 2011/020061 A2 | 2/2011 |
| WO | WO 2013/138322 A1 | 9/2013 |
| WO | WO 2015/051259 A1 | 4/2015 |
| WO | WO 2016/073653 A1 | 5/2016 |
| WO | WO 2016/170124 A2 | 10/2016 |
| WO | WO 2016/180984 A1 | 11/2016 |
| WO | WO 2016/186968 A1 | 11/2016 |
| WO | WO 2017/087691 A1 | 5/2017 |
| WO | WO 2019/065900 A1 | 4/2019 |
| WO | WO 2019/160057 A1 | 8/2019 |
| WO | WO 2019/169165 A1 | 9/2019 |
| WO | WO 2019/213551 A1 | 11/2019 |
| WO | WO 2019/243791 A1 | 12/2019 |
| WO | WO 2020/138491 A1 | 7/2020 |
| WO | WO 2020/198039 A1 | 10/2020 |
| WO | WO 2020/212510 A1 | 10/2020 |
| WO | WO 2021/121366 A1 | 6/2021 |
| WO | WO 2021/137147 A1 | 7/2021 |
| WO | WO 2021/150985 A1 | 7/2021 |
| WO | WO 2021/195627 A1 | 9/2021 |
| WO | WO 2021/207359 A1 | 10/2021 |
| WO | WO 2021/231905 A1 | 11/2021 |
| WO | WO 2021/252971 A1 | 12/2021 |
| WO | WO 2021/255737 A1 | 12/2021 |

OTHER PUBLICATIONS

Bloch, M. H. et al., "Effects of Ketamine in Treatment-Refractory Obsessive-Compulsive Disorder," Biol Psychiatry, 72(11):964-970 (2012).

Carlezon, W. A. & Wise, R. A., "Microinjections of phencyclidine (PCP) and related drugs into nucleus accumbens shell potentiate medial forebrain bundle brain stimulation reward," Psychopharmacology, 128:413-420 (1996).

Carlezon, W. A. & Chartoff, E. H., "Intracranial self-stimulation (ICSS) in rodents to study the neurobiology of motivation," Nature Protocols, 2(11):2987-2995 (2007).

Cooper, M. D. et al., "Strategies to mitigate dissociative and psychotomimetic effects of ketamine in the treatment of major depressive episodes: a narrative review," The World Journal of Biological Psychiatry, 18:6, 410-423 (2017).

Deneau, G. A. & Seevers, M. H., "Pharmacological Aspects of Drug Dependence," Advances in Pharmacology, 3:267-283 (1964).

Diazgranados, N. et al., "A randomized add-on trial of an N-methyl-D-aspartate antagonist in treatment-resistant bipolar depression," Arch Gen Psychiatry, 67(8):793-802 (2010).

Diazgranados, N. et al., "Rapid Resolution of Suicidal Ideation After a Single Infusion of an N-Methyl-D-Aspartate Antagonist in Patients With Treatment-Resistant Major Depressive Disorder," J Clin Psychiatry, 71(12):1605-1611 (2010).

Diniz, B. D. et al., "Late-life depression and risk of vascular dementia and Alzheimer's disease: systematic review and meta-analysis of community-based cohort studies," The British Journal of Psychiatry, 202:329-335 (2013).

Domino, E. F., "Taming the ketamine tiger," Anesthesiology, 113(3):678-686 (2010).

Domino, E. F. & Luby, E. D., "Phencyclidine/Schizophrenia: One View Toward the Past, The Other to the Future," Schizophrenia Bulletin, 38(5):914-919 (2012).

Ebert, B. et al., "Norketamine, the main metabolite of ketamine, is a non-competitive NMDA receptor antagonist in the rat cortex and spinal cord," European Journal of Pharmacology, 333:99-104 (1997).

Elvevåg, B. & Goldberg, T. E., "Cognitive Impairment in Schizophrenia Is the Core of the Disorder," Critical Reviews in Neurobiology, 14(1):1-21 (2000).

Erami, E. et al., "Blockade of orexin receptor 1 attenuates the development of morphine tolerance and physical dependence in rats," Pharmacology, Biochemistry and Behavior, 103:212-219 (2012).

Fan, J.-C. et al., "Neuron-protective effect of subanesthestic-dosage ketamine on mice of Parkinson's disease," Asian Pacific Journal of Tropical Medicine, 10(10):1007-1010 (2017).

Feder, A. et al., "Efficacy of Intravenous Ketamine for Treatment of Chronic Posttraumatic Stress Disorder: A Randomized Clinical Trial," JAMA Psychiatry, 71(6):681-688 (2014).

Ferro, M. M. et al., "Neuroprotective effect of ketamine/xylazine on two rat models of Parkinson's disease," Brazilian Journal of Medical and Biological Research, 40:89-96 (2007).

Fidecka, S., "Interactions of Ketamine, Naloxone and Morphine in the Rat," Pol. J. Pharmacol. Pharm., 39:33-40 (1987).

Freo, U. & Ori, C., "Effects of Anesthesia and Recovery from Ketamine Racemate and Enantiomers on Regional Cerebral Glucose Metabolism in Rats," Anesthesiology, 100:1172-1178 (2004).

Frohlich, J. & Van Horn, J. D., "Reviewing the ketamine model for schizophrenia," Journal of Psychopharmacology, 28(4):287-302 (2014). doi: 10.1177/0269881113512909. Epub Nov. 20, 2013; 16 pages.

Fujita, A. et al., "MPTP-induced dopaminergic neurotoxicity in mouse brain is attenuated after subsequent intranasal administration of (R)-ketamine: a role of TrkB signaling," Psychopharmacology, 237:83-92 (2020); doi: 10.1007/S00213-019-05346-5, Aug. 15, 2019.

Fukumoto, K. et al., "Antidepressant Potential of (R)-Ketamine in Rodent Models: Comparison with (S)-Ketamine," J Pharmacol Exp Ther, 361:9-16 (2017).

Gastambide, F. et al., "Temporally distinct cognitive effects following acute administration of ketamine and phencyclidine in the rat," European Neuropsychopharmacology, 23:1414-1422 (2013).

(56) References Cited

OTHER PUBLICATIONS

Ginski, M. J. & Witkin, J. M., "Sensitive and rapid behavioral differentiation of N-methyl-D-aspartate receptor antagonists," Psychopharmacology, 114:573-582 (1994).
Golden, S. A. et al., "A standardized protocol for repeated social defeat stress in mice," Nature Protocols, 6(8):1183-1191, (2011), including 1 page corrigendum.
Graf, B. M., "Ketamine Has Stereospecific Effects in the Isolated Perfused Guinea Pig Heart," Anesthesiology, 82(6):1426-1437 (1995).
Hachinski, V. et al., "National Institute of Neurological Disorders and Stroke-Canadian Stroke Network Vascular Cognitive Impairment Harmonization Standards," Stroke, 37:2220-2241 (2006).
Han, M. et al., "Intake of 7,8-Dihydroxyflavone During Juvenile and Adolescent Stages Prevents Onset of Psychosis in Adult Offspring After Maternal Immune Activation," Scientific Reports, 6:36087 (2016), 10 pages; doi:10.1038/srep36087.
Hashimoto, K., "Emerging role of glutamate in the pathophysiology of major depressive disorder," Brain Research Reviews, 61:105-123 (2009).
Hashimoto, K. et al., "Reduction of dopamine $D_{2/3}$ receptor binding in the striatum after a single administration of esketamine, but not R-ketamine: a PET study in conscious monkeys," Eur Arch Psychiatry Clin Neurosci, 267:173-176 (2017).
Hashimoto, K. et al., "Phencyclidine-induced cognitive deficits in mice are improved by subsequent subchronic administration of clozapine, but not haloperidol," European Journal of Pharmacology, 519:114-117 (2005).
Hashimoto, K. et al., "Phencyclidine-Induced Cognitive Deficits in Mice are Improved by Subsequent Subchronic Administration of Fluvoxamine: Role of Sigma-1 Receptors," Neuropsychopharmacology, 32:514-521 (2007).
Hashimoto, K. et al., "Phencyclidine-Induced Cognitive Deficits in Mice Are Improved by Subsequent Subchronic Administration of the Novel Selective α7 Nicotinic Receptor Agonist SSR180711," Biol Psychiatry, 63:92-97 (2008).
Hatzigiakoumis, D. S. et al., "Anhedonia and substance dependence: clinical correlates and treatment options," Front. Psychiatry, 2(10):1-12 (2011); https://doi.org/10.3389/fpsyt.2011.00010; 12 pages.
Herman, B. H. et al., "The Effects of NMDA Receptor Antagonists and Nitric Oxide Synthase Inhibitors on Opioid Tolerance and Withdrawal Medication Development Issues for Opiate Addiction," Neuropsychopharmacology, 13(4):269-293 (1995).
Higgins, G. A. & Sellers, E. M., "Antagonist-Precipitated Opioid Withdrawal in Rats: Evidence for Dissociations Between Physical and Motivational Signs," Pharmacology Biochemistry and Behavior, 48(1):1-8 (1994).
Higgins, G. A. et al., "The NMDA Antagonist Dizocilpine (MK801) Attenuates Motivational as well as Somatic Aspects of Naloxone Precipitated Opioid Withdrawal," Life Sciences, 50:PL-167-PL-172 (1992).
Hillhouse, T. M. et al., "Dissociable effects of the noncompetitive NMDA receptor antagonists ketamine and MK-801 on intracranial self-stimulation in rats," Psychopharmacology, 231:2705-2716 (2014).
Hillhouse, T. M. & Porter, J. H., "Ketamine, but not MK-801, produces antidepressant-like effects in rats responding on a differential-reinforcement-of-low-rate operant schedule," Behavioural Pharmacology, 25:80-91 (2014).
Huhn, A. S. et al., Evidence of anhedonia and differential reward processing in prefrontal cortex among post-withdrawal patients with prescription opiate dependence, Brain Research Bulletin, 123:102-109 (2016).
Irwin, S. A. et al., "Daily Oral Ketamine for the Treatment of Depression and Anxiety in Patients Receiving Hospice Care: A 28-Day Open-Label Proof-of-Concept Trial," Journal of Palliative Medicine, 16(8):958-965 (2013).
Jackson-Lewis, V. & Przedborski, S., "Protocol for the MPTP mouse model of Parkinson's disease," Nature Protocols, 2(1):141-151 (2007).
Javitt, D. C. & Zukin, S. R., "Recent Advances in the Phencyclidine Model of Schizophrenia," Am J Psychiatry, 148:1301-1308 (1991).
Ji, D. et al., "NMDA Receptor in Nucleus Accumbens is Implicated in Morphine Withdrawal in Rats," Neorochemical Research, 29(11):2113-2120 (2004).
Johnson, K. M., "Phencyclidine: it ain't excitin', but it sure is toxic," Amino Acids, 45:588-589 (2013).
Jovaiša, T. et al., "Effects of ketamine on precipitated opiate withdrawal," Medicina (Kaunas), 42(8):625-634 (2006).
Kadriu, B. et al., "Acute ketamine administration corrects abnormal inflammatory bone markers in major depressive disorder," Molecular Psychiatry, 23:1626-1631 (2018).
Khanna, J. M. et al., "Effect of NMDA receptor antagonists on rapid tolerance to ethanol," European Journal of Pharmacology, 230:23-31 (1993).
Kolesnikov, Y. et al., "Blockade of Morphine-Induced Hindlimb Myoclonic Seizures in Mice by Ketamine," Pharmacology Biochemistry and Behavior, 56(3): 423-425 (1997).
Koob, G. F. "Neural Mechanisms of Drug Reinforcement," In P. W. Kalivas & H. H. Samson (Eds.), Annals of the New York Academy of Sciences: New York Academy of Sciences, 654:171-191 (1992).
Koob, G. F., "Neurobiological substrates for the dark side of compulsivity in addiction," Neuropharmacology, 56:18-31 (2009).
Koob, G. F. & Volkow, N. D., "Neurobiology of addiction: a neurocircuitry analysis," Lancet Psychiatry, 3:760-773 (2016).
Khorramzadeh, E. & Lofty, A. O., "The Use of Ketamine in Psychiatry," Psychosomatics, 14(6):344-346 (1973).
Koyuncuoğlu, H. et al., "Suppression by Ketamine and Dextromethorphan of Precipitated Abstinence Syndrome in Rats," Pharmacol Biochem Behav, 35(4):829-832 (1990).
Krystal, J. H. et al., "Subanesthetic Effects of the Noncompetitive NMDA Antagonist, Ketamine, in Humans," Arch Gen Psychiatry, 51:199-214 (1994).
Krystal, J. H. et al., "Rapid-Acting Glutamatergic Antidepressants: The Path to Ketamine and Beyond," Biol Psychiatry, 73:1133-1141 (2013).
Krupitsky, E. et al., "Anhedonia, depression, anxiety, and craving in opiate dependent patients stabilized on oral naltrexone or an extended release naltrexone implant," The American Journal of Drug and Alcohol Abuse, 42(5):614-620 (2016).
Langdon, K. J. et al., "Comorbidity of opioid-related and anxiety-related symptoms and disorders," Current Opinion in Psychology, 30:17-23 (2019).
Lapidus, K. A. et al., "A Randomized Controlled Trial of Intranasal Ketamine in Major Depressive Disorder," Biol Psychiatry, Published online Apr. 3, 2014, 17 pages; doi: 10.1016/j.biopsych.2014.03.026.
Li, F. et al., "Cannabinoid $CB_1$ receptor antagonist rimonabant attenuates reinstatement of ketamine conditioned place preference in rats," European Journal of Pharmacology, 589:122-126 (2008).
Li, S. X. et al., "Role of the NMDA receptor in cognitive deficits, anxiety and depressive-like behavior in juvenile and adult mice after neonatal dexamethasone exposure," Neurobiology of Disease, 62:124-134 (2014).
Liu, Y. et al., "Ketamine abuse potential and use disorder," Brain Research Bulletin, 126:68-73 (2016).
Lopez, O. L. et al., "Risk Factors for Mild Cognitive Impairment in the Cardiovascular Health Study Cognition Study," Part 2, Arch Neurol., 60:1394-1399 (2003).
Ma, M. et al., "Key role of soluble epoxide hydrolase in the neurodevelopmental disorders of offspring after maternal immune activation," PNAS, 116(14):7083-7088 (2019).
Matsuura, A. et al., "Dietary glucoraphanin prevents the onset of psychosis in the adult offspring after maternal immune activation," Scientific Reports, 8:2158 (2018); doi: 10.1038/s41598-018-20538-3, 12 pages.
Millan, M. J. et al., "Cognitive dysfunction in psychiatric disorders: characteristics, causes and the quest for improved therapy," Nature Reviews Drug Discovery, 11:141-168 (2012).
Miller, N. S. et al., "The Relationship of Addiction, Tolerance, and Dependence to Alcohol and Drugs: A Neurochemical Approach," Journal of Substance Abuse Treatment, 4:197-207 (1987).

(56) References Cited

OTHER PUBLICATIONS

Mohammadi, A. et al., "Dysfunction in Brain-Derived Neurotrophic Factor Signaling Pathway and Susceptibility to Schizophrenia, Parkinson's and Alzheimer's Diseases," Current Gene Therapy, 18:45-63 (2018).

Muelken, P. et al., "A Two-Day Continuous Nicotine Infusion Is Sufficient to Demonstrate Nicotine Withdrawal in Rats as Measured Using Intracranial Self-Stimulation," PLoS One, 10(12):e0144553 (2015), 18 pages; doi:10.1371/journal.pone.0144553.

Napier, T. C. et al., "Using conditioned place preference to identify relapse prevention medications," Neuroscience and Biobehavioral Reviews, 37:2081-2086 (2013).

Negus, S. S. & Miller, L. L., "Intracranial Self-Stimulation to Evaluate Abuse Potential of Drugs," Pharmacol Rev 66:869-917 (2014).

Nikiforuk, A. & Popik, P., "The effects of acute and repeated administration of ketamine on attentional performance in the five-choice serial reaction time task in rats," Eur Neuropsychopharmacol., 24(8):1381-1393 (2014).

Pan, J. et al., "Blockade of the translocation and activation of c-Jun N-terminal kinase 3 (JNK3) attenuates dopaminergic neuronal damage in mouse model of Parkinson's disease," Neurochemistry International, 54:418-425 (2009).

Paslakis, G. et al., "Oral Administration of the NMDA Receptor Antagonist S-Ketamine as Add-On Therapy of Depression: A Case Series," Pharmacopsychiatry, 43:33-35 (2010).

Paul, R. et al., "Comparison of racemic ketamine and S-ketamine in treatment-resistant major depression: Report of two cases," The World Journal of Biological Psychiatry, 10(3):241-244 (2009).

Perry, M. B., "Perceptions of Mindfulness: A Qualitative Analysis of Group Work in Addiction Recovery," Rhode Island Medical Journal, 102:28-31 (2019).

Persson, J. et al., "The analgesic effect of racemic ketamine in patients with chronic ischemic pain due to lower extremity arteriosclerosis obliterans," Acta Anaesthesiol Scand, 42:750-758 (1998).

Persson, J. et al., "Pharmacokinetics and non-analgesic effects of S- and R-ketamines in health volunteers with normal and reduced metabolic capacity," Eur J Clin Pharmacol, 57:869-875 (2002).

Rodriguez, C. I. et al., "Randomized Controlled Crossover Trial of Ketamine in Obsessive-Compulsive Disorder: Proof-of-Concept," Neuropsychopharmacology, 38:2475-2483 (2013).

Pfenninger, E. G. et al., "Cognitive Impairment after Small-dose Ketamine Isomers in Comparison to Equianalgesic Racemic Ketamine in Human Volunteers," Anesthesiology, 96:357-366 (2002).

Rowland, L. M., "Subanesthetic Ketamine: How It Alters Physiology and Behavior in Humans," Aviat Space Environ Med, 76(7, Suppl.):C52-58 (2005).

Sams-Dodd, F., "Phencyclidine-induced stereotyped behaviour and social isolation in rats: a possible animal model of schizophrenia," Behavioural Pharmacology, 7:3-23 (1996).

Schmidt, A. et al., "Cerebral physiological responses to bolus injection of racemic, S(+)- or R(-)-keamine in the pig," Acta Anaesthesiol Scand, 49:1436-1442 (2005).

Sekine, Y. et al., "Methamphetamine-Related Psychiatric Symptoms and Reduced Brain Dopamine Transporters Studied With PET," Am J Psychiatry, 158:1206-1214 (2001).

Shearman, G. T. et al., "Effectiveness of Lofexidine in Blocking Morphine-Withdrawal Signs in the Rat," Pharmacology Biochemistry & Behavior, 12:573-575 (1980).

Streel, E. et al., "Effects of anaesthetic agents in interference of naloxone-induced opiate-withdrawal are dose-dependent in opiate-dependent rats," Life Sciences, 77:650-655 (2005).

Suzuki, T. et al., "Effects of the non-competitive NMDA receptor antagonist ketamine on morphine-induced place preference in mice," Life Sciences, 67:383-389 (2000).

Tannock, I. F. et al., "Cognitive Impairment Associated With Chemotherapy for Cancer: Report of a Workshop," Journal of Clinical Oncology, 22(11):2233-2239 (2004).

Trujillo, K. A., "Effects of Noncompetitive N-Methyl-D-Aspartate Receptor Antagonists on Opiate Tolerance and Physical Dependence," Neuropsychopharmacology, 13:301-307(1995).

Tsai, S.-J., "TrkB partial agonists: Potential treatment strategy for epilepsy, mania, and autism," Medical Hypotheses, 66:173-175 (2006).

Tzschentke, T. M., "Measuring reward with the conditioned place preference (CPP) paradigm: update of the last decade," Addiction Biology, 12:227-462 (2007).

Van Dam, F. S. A. M. et al., "Impairment of Cognitive Function in Women Receiving Adjuvant Treatment for High-Risk Breast Cancer: High-Dose Versus Standard-Dose Chemotherapy," J. Natl Cancer Inst, 90(3):210-218 (1998).

Vayr, F. et al., "Barriers to seeking help for physicians with substance use disorder: A review," Drug and Alcholol Dependence, 199:116-121 (2019).

Vogels, R. L. C. et al., "Cognitive impairment in heart failure: A systematic review of the literature," European Journal of Heart Failure, 9:440-449 (2007).

Volkow, N. D. et al., "Association of Dopamine Transporter Reduction With Psychomotor Impairment in Methamphetamine Abusers," Am J Psychiatry, 158:377-382 (2001).

Volkow, N. D. et al., "Decreased striatal dopaminergic responsiveness in detoxified cocaine-dependent subjects," Nature, 386:830-833 (1997).

Vollenweider, F. X. et al., "Differential psychopathology and patterns of cerebral glucose utilization produced by (S)- and (R)-ketamine in healthy volunteers using positron emission tomography (PET)," Eur. Neuropsychopharmacol. 7:25-38 (1997).

Wang, C. et al., "Brain damages in ketamine addicts as revealed by magnetic resonance imaging," Front. Neuroanat., vol. 7, Article 23 (2013), 8 pages; doi.org/10.3389/fnana.2013.00023.

White, P. F. et al., "Comparative pharmacology of the ketamine isomers," Br. J. Anaesth., 57:197-203 (1985).

Wink, L. K. et al., "Intranasal Ketamine Treatment in an Adult With Autism Spectrum Disorder," J Clin Psychiatry, 75(8):835-836 (2014).

Womble, A. L., "Effects of Ketamine on Major Depressive Disorder in a Patient with Posttraumatic Stress Disorder," AANA Journal, 81(2):118-119 (2013).

Xiaoyin, K. et al., "The profile of cognitive impairments in chronic ketamine users," Psychiatry Research, 266:124-131 (2018).

Xiong, Z. et al., "Beneficial effects of (R)-ketamine, but not its metabolite (2R,6R)-hydroxynorketamine, in the depression-like phenotype, inflammatory bone markers, and bone mineral density in a chronic social defeat stress model," Behavioural Brain Research, 368:111904 (2019), 7 pages; https://doi.org/10.1016/j.bbr.2019.111904.

Yamamoto, N. et al., "Ketamine reduces amyloid-protein degradation by suppressing neprilysin expression in primary cultured astrocytes," Neuroscience Letters, 545:54-58 (2013).

Yang, C. et al., "R-ketamine: a rapid-onset and sustained antidepressant without psychotomimetic side effects," Transl Psychiatry, 5:e632 (2015), 11 pages; doi:10.1038/tp.2015.136.

Yang, C. et al., "Loss of parvalbumin-immunoreactivity in mouse brain regions after repeated intermittent administration of esketamine, but not R-ketamine," Psychiatry Research, 239:281-283 (2016).

Yoon, G. et al., "Association of Combined Naltrexone and Ketamine With Depressive Symptoms in a Case Series of Patients With Depression and Alcohol Use Disorder," JAMA Psychiatry, published online Jan. 9, 2019; doi:10.1001/jamapsychiatry.2018.3990, 2 pages.

Zanos, P. et al., "NMDAR inhibition-independent antidepressant actions of ketamine metabolites," Nature, 533:481-486 (2016), and Methods, 12 pages.

Zarate, C. A. et al., "A Randomized Trial of an N-methyl-d-aspartate Antagonist in Treatment-Resistant Major Depression," Arch Gen Psychiatry, 63: 856-864 (2006).

Zhang, J.-c, Z. et al., "R(-)-ketamine shows greater potency and longer lasting antidepressant effects than S(+)-ketamine," Pharmacology, Biochemistry and Behavior, 116:137-141 (2014).

(56) References Cited

OTHER PUBLICATIONS

Zhang, K. et al., "Role of Inflammatory Bone Markers in the Antidepressant Actions of (R)-Ketamine in a Chronic Social Defeat Stress Model," International Journal of Neuropsychopharmacology, 21(11):1025-1030 (2018).
Zhu, W. et al., "Risks Associated with Misuse of Ketamine as a Rapid-Acting Antidepressant," Neurosci. Bull., 32(6):557-564 (2016).
Ezquerra-Romano, I. I. et al., "Ketamine for the treatment of addiction: Evidence and potential mechanisms," Neuropharmacology, 142:72-82 (2018).
Kawasaki, C. et al., "Ketamine isomers suppress superantigen-induced proinflammatory cytokine production in human whole blood," Can J Anesth, 48(8):819-823 (2001).
Mizukami,K., "Alzheimer's Disease and Depression," Journal of Neurology, 115(11):1122-1125 (2013). English Abstract Only.
Rodan, G. A. & Martin, T., "Therapeutic Approaches to Bone Diseases," Science, 289:1508-1514 (2000).
Shah, S. et al., "Combination of oral ketamine and midazolam as a premedication for a severely autistic and combative patient," J Anesth, 23:126-128 (2009).
Webb, D. R., "Animal models of human disease: Inflammation," Biochemical Pharmacology, 87:121-130 (2014).
Janssen Pharmaceutical Companies. Medication Guide SPRAVATO™ CIII (esketamine) nasal spray: prescribing information. 2020. Titusville, NJ, USA, 44 pages.
Tian, Z. et al. "Expression of heat shock protein HSP-70 in the retrosplenial cortex of rat brain after administration of (R,S)-ketamine and (S)-ketamine, but not (R)-ketamine", Pharmacol Biochem Behav, 2018; 172:17-21.
Tian, Z. et al. "Lack of antidepressant effects of (2R,6R)-hydroxynorketamine in a rat learned helplessness model: comparison with (R)-ketamine", Int J Neuropsychopharmacol, 2018; 21(1):84-88.
Ide, S. et al. Cognitive impairment that is induced by (R)-ketamine is abolished in NMDA GluN2D receptor subunit knockout mice. Int J Neuropsychopharmacol, 2019; 22(7):449-452.
Chang, L. et al. "Comparison of antidepressant and side effects in mice after intranasal administration of (R,S)-ketamine, (R)-ketamine, and (S)-ketamine", Pharmacol Biochem Behav, 2019; 181:53-59.
Chang, L. et al. "Lack of dopamine D1 receptors in the antidepressant actions of (R)-ketamine in a chronic social defeat stress model", Eur Arch Psychiatry Clin Neurosci, 2020; 270:271-275.
Ago, Y. et al. "(R)-ketamine induces a greater increase in prefrontal 5-HT release than (S)-ketamine and ketamine metabolites via an AMPA receptor-independent mechanism", Int J Neuropsychopharmacol, 2019; 22(10):665-674.
Yang, C. et al. "(R)-ketamine shows greater potency and longer lasting antidepressant effects than its metabolite (2R,6R)-hydroxynorketamine", Biol Psychiatry, 2017; 82(5):e43-e44, 2 pages.
Yang, C. et al. "Possible role of the gut microbiota-brain axis in the antidepressant effects of (R)-ketamine in a social defeat stress model", Transl Psychiatry, 2017; 7(12): 1294, 11 pages.
Shirayama, Y. and Hashimoto, K. "Effects of a single bilateral infusion of R-ketamine in the rat brain regions of a learned helplessness model of depression", Eur Arch Psychiatry Clin Neurosci, 2017; 267(2): 177-182.

Yang, C. et al. "AMPA Receptor Activation-Independent Antidepressant Actions of Ketamine Metabolite (S)-Norketamine", Biol Psychiatry, 2018; 84(8):591-600.
Li, J.-M. et al. "Ketamine may exert antidepressant effects via suppressing NLRP3 inflammasome to upregulate AMPA receptors", Neuropharmacology, 2019; 146:149-153.
Zhang, M. et al. "Effects of subanesthetic intravenous ketamine infusion on neuroplasticity-related proteins in the prefrontal cortex, amygdala, and hippocampus of Sprague-Dawley rats", IBRO Rep, 2019; 6:87-94.
Zanos, P. et al. "(R)-ketamine exerts antidepressant actions partly via conversion to (2R,6R)-hydroxynorketamine, while causing adverse effects at sub-anesthetic doses", Br J Pharmacol, 2019; 176(14):2573-2592.
Klepstad, P. et al. "Evidence of a role for NMDA receptors in pain perception", Eur J Pharmacol, 1990; 187(3):513-518.
Mathisen, L.C. et al. "Effect of ketamine, an NMDA receptor inhibitor, in acute and chronic orofacial pain", Pain, 1995; 61(2):215-220.
Oye I, Paulsen O, Maurset A. "Effects of ketamine on sensory perception: evidence for a role of N-methyl-D-aspartate receptors", J Pharmacol Exp Ther, 1992; 260(3):1209-1213.
Pfenninger EG, Durieux ME, Himmelseher S. "Cognitive impairment after small-dose ketamine isomers in comparison to equianalgesic racemic ketamine in human volunteers", Anesthesiology, 2002; 96(2):357-366.
WHO. Depression. 2017; 5 pages; Available from: www.who.int/news-room/factsheets/detail/depression.
CDC. National Violent Death Reporting System. 2015; 2 pages; Available from: www.cdc.gov/violenceprevention/nvdrs/index.html.
Canuso, C.M. et al. "Efficacy and safety of intranasal esketamine for the rapid reduction of symptoms of depression and suicidality in patients at imminent risk for suicide: results of a double-blind, randomized, placebo-controlled study", Am J Psychiatry, 2018; 175(7):620-630.
Souery, D. et al. "Clinical factors associated with treatment resistance in major depressive disorder: results from a European multicenter study", J Clin Psychiatry, 2007; 68(7):1062-1070.
Ivanova, J.I. et al. "Direct and indirect costs of employees with treatment-resistant and non-treatment-resistant major depressive disorder", Curr Med Res Opin, 2010; 26(10):2475-2484.
Chan, W.-H. et al. "Induction of rat hepatic cytochrome P-450 by ketamine and its toxicological implications", J Toxicol Environ Health A, 2005; 68(17-18):1581-1597.
Zanos, P. and Gould, T. D. "Intracellular signaling pathways involved in (S)- and (R)-ketamine antidepressant actions", Biol Psychiatry, 2018; 83(1):2-4.
Zanos, P. et al. "Ketamine and ketamine metabolite pharmacology: insights into therapeutic mechanisms", Pharmacol Rev, 2018; 70(3):621-660.
Leal, G. C. et al. "Intravenous arketamine for treatment-resistant depression: open-label pilot study", Eu Arch Psych Clin Neurosci, 2021, 271:577-582.
Sheehan, D.V. et al. "The Mini-International Neuropsychiatric Interview (M.I.N.I.): the development and validation of a structured diagnostic psychiatric interview for DSM-IV and ICD-10", J Clin Psychiatry 1998; 59 Suppl 20:22-33.

\* cited by examiner

DEX: dexamethasone. LMT: locomotion test. TST: tail suspension test.
FST: force swimming test. SPT: 1% sucrose preference test.

R-Ket: R-ketamine. S-Ket: S-ketamine. SPT: 1% sucrose preference test.
LMT: locomotion test. TST: tail suspension test. FST: force swimming test.

1) Saline + Saline group
2) Saline + Morphine (5 mg/kg, i.p.) group
3) R-ketamine (10 mg/kg, i.p.) + Morphine (5 mg/kg, i.p.) group

METHODS OF TREATING SUBSTANCE ABUSE

CROSS REFERENCE TO RELATED APPLICATIONS

This application is a U.S. National Phase Application, filed under 35 U.S.C. § 371, of International Application No. PCT/US2019/030644, filed on May 3, 2019, which claims priority to and the benefit of U.S. Provisional Patent Application No. 62/666,813, filed on May 4, 2018, the contents of each of which are incorporated herein by reference in their entireties.

FIELD OF THE DISCLOSURE

The invention relates to the treatment of substance use disorders, and the fields of neurobiology and pharmacotherapy. More specifically, the invention relates to a composition comprising R(−)-ketamine or a pharmaceutically acceptable salt thereof, and to a pharmaceutical composition for treatment of substance use disorders, including R(−)-ketamine or a pharmaceutically acceptable salt thereof, and being substantially free of S(+)-ketamine or a pharmaceutically acceptable salt thereof.

BACKGROUND OF THE INVENTION

In 2016, approximately 20.1 million Americans aged 12 years or older had a substance use disorder related to use of alcohol or illicit drugs. This included 15.1 million individuals with a use disorder related to alcohol, 4.0 million with a substance use disorder related to marijuana, and 2.1 million with a substance use disorder related to opioids. 8.2 million adults and 333,000 adolescents had both a psychiatric disorder and a substance use disorder. 21 million individuals needed treatment for a substance use disorder, and only 3.8 million received any treatment (Substance Abuse and Mental Health Services Administration. (2017) *Key substance use and mental health indicators in the United States: Results from the* 2016 *National Survey on Drug Use and Health* (HHS Publication No. SMA 17-5044, NSDUH Series H-52)). The yearly annual economic impact from the misuse of drugs or alcohol is estimated to be over $400 billion. Even amongst those who receive treatment, relapse rates can be as high as 85% within one year of treatment. There thus exists an unmet and pressing need in the art for novel methods to treat substance use disorders. The invention provides one such method, that of administering to a subject in need thereof a composition comprising R(−)-ketamine.

SUMMARY OF THE INVENTION

The disclosure provides a method of treating a substance use disorder in a subject, comprising administering to the subject a therapeutically effective amount of a composition comprising R(−)-ketamine or a pharmaceutically acceptable salt thereof, wherein the composition is substantially free of S(+)-ketamine or a pharmaceutically acceptable salt thereof.

In some embodiments of the methods of the disclosure, the substance use disorder comprises abuse of alcohol, marijuana, synthetic cannabinoids, opioids, stimulants, barbiturates, benzodiazepines, dextromethorphan (DXM), a sleep medication, khat, synthetic cathinones, cocaine, 3,4-methylenedioxymethamphetamine (MDMA), phencyclidine (PCP), lysergic acid diethylamide (LSD), psilocybin, an inhalant, Rohypnol, gamma-hydroxybutyric acid (GHB), N,N-Dimethyltryptamine (DMT), ayahuasca, mescaline, salvia, or nicotine.

In some embodiments of the methods of the disclosure, the therapeutically effective amount of the composition comprising R(−)-ketamine does not cause anhedonia or negative affect in the subject.

In some embodiments of the methods of the disclosure, the substance use disorder comprises abuse of opioids.

In some embodiments of the methods of the disclosure, the substance use disorder comprises abuse of alcohol.

In some embodiments of the methods of the disclosure, the opioid comprises Heroin, Codeine, Fentanyl, Hydrocodone (Dihydrocodeinone), Hydromorphone, Meperidine, Methadone, Morphine, Oxycodone or Oxymorphone. In some embodiments, the stimulant comprises Amphetamine, Amphetamine sulfate, Methamphetamine, Dextroamphetamine, Levoamphetamine, Lisdexamfetamine, Atomoxetine, Methylphenidate, Dexmethylphenidate, Oxymetazoline, Pseudoephedrine, Phenylephrine or a combination thereof. In some embodiments, the benzodiazepine comprises Aprazolam, Chlorodiazepoxide, Diazepam, Lorazepam or Triazolam. In some embodiments, the barbiturate comprises Phenobarbital, Pentobarbital, Methohexital, Secobarbital, Butabarbital or Butalbital. In some embodiments, the sleep medication comprises Eszopiclone, Zaleplon or Zolpidem.

In some embodiments of the methods of the disclosure, administering the composition reduces a symptom of withdrawal or prevents a relapse of the substance use disorder in the subject.

In some embodiments of the methods of the disclosure, the method further comprises an additional pharmacotherapy for substance abuse. In some embodiments, the additional pharmacotherapy comprises a gradually reducing regimen, a substitution therapy or a medication assisted treatment.

In some embodiments of the methods of the disclosure, administering the composition reduces tolerance to a substance of the substance use disorder in the subject. In some embodiments, administering the composition reduces dependence on a substance of the substance use disorder in the subject. In some embodiments, administering the composition improves adherence to a treatment for the substance use disorder in the subject. In some embodiments, administering the composition reduces a preference for a substance of the substance use disorder or decreases liking for a substance the substance use disorder in the subject. In some embodiments, administering the composition increases abstinence from a substance of the substance use disorder in the subject.

In some embodiments of the methods of the disclosure, the method further comprises a behavioral therapy. In some embodiments, the behavioral therapy comprises counseling, a contingency management system, a mindfulness based therapy, a cognitive-behavioral therapy, a digitally administered behavioral therapy or a virtual reality based behavioral therapy. In some embodiments, the counseling is in person or digitally administered. In some embodiments, the method reduces the amount behavioral therapy required compared behavioral therapy without the administration of the composition.

In some embodiments of the methods of the disclosure, the method further comprises an additional pharmacotherapy for substance abuse. In some embodiments, the additional pharmacotherapy comprises a gradually reducing regimen, a substitution therapy or a medication assisted treatment. In some embodiments, the substance use disorder comprises abuse of an opioid, and the substitution therapy comprises Methadone or Buprenorphine. In some embodiments, the substance abuse disorder comprises abuse of an opioid, and the medication assisted treatment comprises Naltrexone. In some embodiments, the substance use disorder comprises alcohol abuse, and wherein the medication assisted treatment comprises Disulfiram, Acamprosate or Naltrexone.

In some embodiments of the methods of the disclosure, the composition is administered prior to the additional therapy. In some embodiments, the composition is administered at the same time as the additional therapy. In some embodiments, the composition is administered after the additional therapy.

In some embodiments of the methods of the disclosure, the composition is administered every day, every 2 days, every 3 days, every 4 days, every 7 days, every 10 days, every 14 days or every 30 days.

In some embodiments of the methods of the disclosure, the composition further comprises a pharmaceutically acceptable carrier. In some embodiments, the composition comprises about 0.01 mg to about 500 mg of R(−)-ketamine or a pharmaceutically acceptable salt thereof. In some embodiments, the composition comprises about 0.1 mg to about 500 mg of R(−)-ketamine or a pharmaceutically acceptable salt thereof. In some embodiments, the composition comprises about 0.1 mg to about 100 mg of R(−)-ketamine or a pharmaceutically acceptable salt thereof. In some embodiments, the pharmaceutically acceptable salt of R(−)-ketamine is R(−)-ketamine hydrochloride.

In some embodiments of the methods of the disclosure, the composition is formulated for intravenous, intramuscular, sublingual, subcutaneous, transnasal, oral, rectal or transdermal administration.

The disclosure provides a method of treating at least one substance use withdrawal symptom in a subject, comprising administering to the subject a therapeutically effective amount of a composition comprising R(−)-ketamine or a pharmaceutically acceptable salt thereof, wherein the composition is substantially free of S(+)-ketamine or a pharmaceutically acceptable salt thereof.

In some embodiments of the methods of the disclosure, the at least one substance use withdrawal symptom comprises a symptom of withdrawal from alcohol, marijuana, synthetic cannabinoids, opioids, stimulants, barbiturates, benzodiazepines, dextromethorphan (DXM), a sleep medication, khat, synthetic cathinones, cocaine, 3,4-methylenedioxymethamphetamine (MDMA), phencyclidine (PCP), lysergic acid diethylamide (LSD), psilocybin, an inhalant, Rohypnol, gamma-hydroxybutyric acid (GHB), N,N-Dimethyltryptamine (DMT), ayahuasca, mescaline, salvia, or nicotine.

In some embodiments of the methods of the disclosure, the therapeutically effective amount of the composition comprising R(−)-ketamine does not cause anhedonia or negative affect in the subject.

In some embodiments of the methods of the disclosure, the at least one substance use withdrawal symptom comprises a symptom of withdrawal from opioids.
In some embodiments of the methods of the disclosure, the at least one substance use withdrawal symptom comprises a symptom of withdrawal from alcohol.

In some embodiments of the methods of the disclosure, the opioid comprises Heroin, Codeine, Fentanyl, Hydrocodone (Dihydrocodeinone), Hydromorphone, Meperidine, Methadone, Morphine, Oxycodone or Oxymorphone. In some embodiments, the stimulant comprises Amphetamine, Amphetamine sulfate, Methamphetamine, Dextroamphetamine, Levoamphetamine, Lisdexamfetamine, Atomoxetine, Methylphenidate, Dexmethylphenidate, Oxymetazoline, Pseudoephedrine, Phenylephrine or a combination thereof. In some embodiments, the benzodiazepine comprises Aprazolam, Chlorodiazepoxide, Diazepam, Lorazepam or Triazolam. In some embodiments, the barbiturate comprises Phenobarbital, Pentobarbital, Methohexital, Secobarbital, Butabarbital or Butalbital. In some embodiments, the sleep medication comprises Eszopiclone, Zaleplon or Zolpidem.

In some embodiments of the methods of the disclosure, the at least one substance use withdrawal symptom comprises a physical symptom of withdrawal, a psychological symptom of withdrawal or a combination thereof. In some embodiments, the physical symptom of withdrawal comprises tremors, insomnia, disturbed sleep, headache, sweating, nausea, vomiting, muscle pain, muscle stiffness, hypertension, irregular heart rate, elevated heart rate, heart palpitations, dizziness, shakiness, tremors, seizures, dehydration, shallow breathing, fatigue, loss of appetite, clammy skin, loss of color or a combination thereof. In some embodiments, the psychological symptom of withdrawal comprises anxiety, irritability, difficulty concentrating, difficulty thinking clearly, mood swings, nightmares, depression, tension, panic attacks, short term memory loss, restlessness, a feeling of helplessness, stress-sensitivity, a heightened responsivity to substance-related cues, aberrant reward processing, a substance craving or a combination thereof.

In some embodiments of the methods of the disclosure, the method further comprises an additional pharmacotherapy for withdrawal. In some embodiments, the additional pharmacotherapy comprises a gradually reducing regimen, a substitution therapy or a medication assisted treatment.

In some embodiments of the methods of the disclosure, the method further comprises a behavioral therapy. In some embodiments, the behavioral therapy comprises counseling, a contingency management system, a mindfulness based therapy, a cognitive-behavioral therapy, a digitally administered behavioral therapy or a virtual reality based behavioral therapy. In some embodiments, the counseling is in person or digitally administered. In some embodiments, the method reduces the amount behavioral therapy required compared behavioral therapy without the administration of the composition.

In some embodiments of the methods of the disclosure, the method further comprises an additional pharmacotherapy for withdrawal. In some embodiments, the additional pharmacotherapy comprises a gradually reducing regimen, a substitution therapy or a medication assisted treatment. In some embodiments, the withdrawal symptom comprises a symptom of withdrawal from an opioid, and the substitution therapy comprises Methadone or Buprenorphine. In some embodiments, the withdrawal symptom comprises a symptom of withdrawal from an opioid, and the medication assisted treatment comprises Naltrexone. In some embodiments, the withdrawal symptom comprises a symptom of withdrawal from alcohol, and the medication assisted treatment comprises Disulfiram, Acamprosate or Naltrexone. In some embodiments, the composition is administered prior to the onset of the at least one withdrawal symptom in the subject. In some embodiments, the composition is administered at the same time as the onset of the at least one withdrawal symptom in the subject. In some embodiments, the composition is administered after the onset of the at least one withdrawal symptom in the subject.

In some embodiments of the methods of the disclosure, the composition is administered every 24 hours, 2 days, every 3 days, every 4 days, every 7 days, every 10 days, every 14 days or every 30 days.

In some embodiments of the methods of the disclosure, the composition further comprises a pharmaceutically acceptable carrier.

In some embodiments of the methods of the disclosure, the composition comprises about 0.01 mg to about 500 mg of R(−)-ketamine or a pharmaceutically acceptable salt thereof. In some embodiments, the composition comprises about 0.1 mg to about 500 mg of R(−)-ketamine or a pharmaceutically acceptable salt thereof. In some embodiments, the composition comprises about 0.1 mg to about 100 mg of R(−)-ketamine or a pharmaceutically acceptable salt thereof. In some embodiments, the pharmaceutically acceptable salt of R(−)-ketamine is R(−)-ketamine hydrochloride. In some embodiments, composition is formulated for intravenous, intramuscular, sublingual, subcutaneous, transnasal, oral, rectal or transdermal administration.

In some embodiments of the methods of the disclosure, the composition reduces or eliminates the at least one substance use withdrawal symptom in the subject.

The disclosure provides a method of treating psychological symptoms associated with a substance use disorder in a subject, comprising administering to the subject a therapeutically effective amount of a composition comprising R(−)-ketamine or a pharmaceutically acceptable salt thereof, wherein the composition is substantially free of S(+)-ketamine or a pharmaceutically acceptable salt thereof.

In some embodiments of the methods of disclosure, the psychological symptom comprises a psychological symptom of withdrawal from alcohol, marijuana, synthetic cannabinoids, opioids, stimulants, barbiturates, benzodiazepines, dextromethorphan (DXM), a sleep medication, khat, synthetic cathinones, cocaine, 3,4-methylenedioxymethamphetamine (MDMA), phencyclidine (PCP), lysergic acid diethylamide (LSD), psilocybin, an inhalant, Rohypnol, gamma-hydroxybutyric acid (GHB), N,N-Dimethyltryptamine (DMT), ayahuasca, mescaline, salvia, or nicotine.

In some embodiments of the methods of the disclosure, administering to the subject a therapeutically effective amount of the composition comprising R(−)-ketamine does not cause anhedonia or negative affect in the subject.

In some embodiments of the methods of the disclosure, the psychological symptom comprises a psychological symptom of a mood disorder that is comorbid with the substance use disorder. In some embodiments, the mood disorder comprises major depressive disorder, bipolar disorder, post traumatic stress disorder, obsessive compulsive disorder or dementia.

In some embodiments, the opioid comprises Heroin, Codeine, Fentanyl, Hydrocodone (Dihydrocodeinone), Hydromorphone, Meperidine, Methadone, Morphine, Oxycodone or Oxymorphone. In some embodiments, the stimulant comprises Amphetamine, Amphetamine sulfate, Methamphetamine, Dextroamphetamine, Levoamphetamine, Lisdexamfetamine, Atomoxetine, Methylphenidate, Dexmethylphenidate, Oxymetazoline, Pseudoephedrine, Phenylephrine or a combination thereof. In some embodiments, the benzodiazepine comprises Aprazolam, Chlorodiazepoxide, Diazepam, Lorazepam or Triazolam. In some embodiments, the barbiturate comprises Phenobarbital, Pentobarbital, Methohexital, Secobarbital, Butabarbital or Butalbital.

In some embodiments, the sleep medication comprises Eszopiclone, Zaleplon or Zolpidem.

In some embodiments of the methods of the disclosure, the psychological symptom comprises anxiety, irritability, difficulty concentrating, difficulty thinking clearly, mood swings, nightmares, depression, tension, panic attacks, short term memory loss, restlessness, a feeling of helplessness, stress-sensitivity, a heightened responsivity to substance-related cues, aberrant reward processing, a substance craving or a combination thereof.

In some embodiments of the methods of the disclosure, the method further comprises an additional pharmacotherapy. In some embodiments, the additional pharmacotherapy comprises a gradually reducing regimen, a substitution therapy or a medication assisted treatment.

In some embodiments of the methods of the disclosure, the method further comprises a behavioral therapy. In some embodiments, the behavioral therapy comprises counseling, a contingency management system, a mindfulness based therapy, a cognitive-behavioral therapy, a digitally administered behavioral therapy or a virtual reality based behavioral therapy. In some embodiments, the counseling is in person or digitally administered. In some embodiments, the method reduces the amount behavioral therapy required compared behavioral therapy without the administration of the composition.

In some embodiments of the methods of the disclosure, the composition is administered prior to the onset of the at least one psychological symptom in the subject. In some embodiments, the composition is administered at the same time as the onset of the at least one psychological symptom in the subject. In some embodiments, the composition is administered after the onset of the at least one psychological symptom in the subject.

In some embodiments of the methods of the disclosure, the composition is administered every 24 hours, 2 days, every 3 days, every 4 days, every 7 days, every 10 days, every 14 days or every 30 days.

In some embodiments of the methods of the disclosure, the composition further comprises a pharmaceutically acceptable carrier. In some embodiments, the composition comprises about 0.01 mg to about 500 mg of R(−)-ketamine or a pharmaceutically acceptable salt thereof. In some embodiments, the composition comprises about 0.1 mg to about 500 mg of R(−)-ketamine or a pharmaceutically acceptable salt thereof. In some embodiments, the composition comprises about 0.1 mg to about 100 mg of R(−)-ketamine or a pharmaceutically acceptable salt thereof. In some embodiments, the pharmaceutically acceptable salt of R(−)-ketamine is R(−)-ketamine hydrochloride. In some embodiments, the composition is formulated for intravenous, intramuscular, sublingual, subcutaneous, transnasal, oral, rectal or transdermal administration.

In some embodiments of the methods of the disclosure, the composition reduces or eliminates the at least one psychological symptom in the subject.

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the disclosure have been illustrated and described, various other changes and modifications can be made without departing from the spirit and scope of the disclosure. The scope of the appended claims includes all such changes and modifications that are within the scope of this disclosure.

BRIEF DESCRIPTION OF THE DRAWINGS

In FIG. 2A, DEX means dexamethasone, LMT means a locomotion test, TST means a tail suspension test, FST means a forced swimming test, and SPT means a 1% sucrose preference test (Example 1).

In FIG. 2B, R-Ket and S-Ket represent DEX-treated mouse groups injected with R(−)-ketamine and S(+)-ketamine, respectively, Saline represents a DEX-treated mouse group injected with saline, and Cont represents a control mouse group injected with saline. The ordinate axis of FIG. 2B indicates locomotions (count/60 min) (Example 1).

In FIG. 2C, R-Ket and S-Ket represent DEX-treated mouse groups injected with R(−)-ketamine and S(+)-ketamine, respectively, Saline represents a DEX-treated mouse group injected with saline, and Cont represents a control mouse group injected with saline. The ordinate axis of FIG. 2C indicates immobility times (sec) in the TST (Example 1).

In FIG. 2D, R-Ket and S-Ket represent DEX-treated mouse groups injected with R(−)-ketamine and S(+)-ketamine, respectively, Saline represents a DEX-treated mouse group injected with saline, and Cont represents a control mouse group injected with saline. The ordinate axis of FIG. 2D indicates immobility times (sec) in the FST (Example 1).

In FIG. 2E, R-Ket and S-Ket represent DEX-treated mouse groups injected with R(−)-ketamine and S(+)-ketamine, respectively. Saline represents a DEX-treated mouse group injected with saline, and Cont represents a control mouse group injected with saline. The ordinate axis of FIG. 2E indicates sucrose preferences (%) in the SPT (Example 1).

In FIG. 2F, R-Ket and S-Ket represent DEX-treated mouse groups injected with R(−)-ketamine and S(+)-ketamine, respectively. Saline represents a DEX-treated mouse group injected with saline, and Cont represents a control mouse group injected with saline. The ordinate axis of FIG. 2F indicates immobility times (sec) in the TST (Example 1).

In FIG. 2G, R-Ket and S-Ket represent DEX-treated mouse groups injected with R(−)-ketamine and S(+)-ketamine, respectively. Saline represents a DEX-treated mouse group injected with saline, and Cont represents a control mouse group injected with saline. The ordinate axis of FIG. 2G indicates immobility times (sec) in the PST (Example 1).

In FIG. 3A, R-Ket and S-Ket represent social defeat stress mouse groups injected with R(−)-ketamine and S(+)-ketamine, respectively. Saline represents a social defeat stress mouse group injected with saline. In FIG. 3A, LMT means a locomotion test, TST means a tail suspension test, PST means a forced swimming test, and SPT means a 1%/o sucrose preference test (Example 2).

In FIG. 3B, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3B indicates sucrose preferences (%) in the SPT (Example 2).

In FIG. 3C, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3C indicates locomotions (count/60 min) in the LMT (Example 2).

In FIG. 3D, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3D indicates immobility times (sec) in the TST (Example 2).

In FIG. 3E, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3E indicates immobility times (sec) in the PST (Example 2).

In FIG. 3F, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3F indicates sucrose preferences (%) in the SPT (Example 2).

In FIG. 3G, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3G indicates immobility times (sec) in the TST (Example 2).

In FIG. 3H, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. The ordinate axis of FIG. 3H indicates immobility times (sec) in the PST (Example 2).

In FIG. 3I, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline. In addition, mPFC means the medial prefrontal cortex (Example 2).

In FIG. 3J, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline (Example 2).

In FIG. 3J, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline (Example 2).

In FIG. 3J, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline (Example 2).

In FIG. 3J, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline (Example 2).

In FIG. 3J, R-Ket and S-Ket represent social defeat stress mouse groups injected with R(−)-ketamine and S(+)-ketamine, respectively. Saline represents a social defeat stress mouse group injected with saline, and Control represents a control mouse group injected with saline (Example 2).

In FIG. 4, R-Ket, S-Ket, and Saline represent groups injected with R(−)-ketamine, S(+)-ketamine, and saline, respectively. The ordinate axis of FIG. 4 indicates locomotion (count/10 min) (Example 3).

In FIG. 5A, R-Ket and Saline represent groups injected with R(−)-ketamine and saline, respectively. PP69, PP73, PP77, and PP81 mean that stimuli at 69, 73, 77, and 81 dB for more than 20 milliseconds were presented 100 milliseconds before a 110-dB pulse, respectively. Data analysis was performed by Wilks Lambda, which is multivariate analysis of variance (Example 3).

In FIG. 5B, S-Ket and Saline represent groups injected with S(+)-ketamine and saline, respectively. PP69, PP73, PP77, and PP81 mean that stimuli at 69, 73, 77, and 81 dB for more than 20 milliseconds were presented 100 milliseconds before a 110-dB pulse, respectively. Data analysis was performed by Wilks Lambda, which is multivariate analysis of variance (Example 3).

In FIG. 6A, R-Ket, S-Ket, and RS-Ket mean groups injected with R(−)-ketamine, S(+)-ketamine, and RS(+/−)-ketamine, respectively. In each of the groups, the injection was performed three times, i.e., on day 4, day 6, and day 8. Saline means a group injected with saline. In the group, the injection was performed three times, i.e., on day 5, day 7, and day 9 (Example 3).

In FIG. 6B, R-Ketamine and Saline represent groups injected with R(−)-ketamine and saline, respectively. The ordinate axis of FIG. 6B indicates conditioned place preference test scores (CPP scores) (Example 3).

In FIG. 6C, S-Ketamine and Saline represent groups injected with S(+)-ketamine and saline, respectively. The ordinate axis of FIG. 6C indicates conditioned place preference test scores (CPP scores. (Example 3).

In FIG. 6D, RS-Ketamine and Saline represent groups injected with RS(+/−)-ketamine and saline, respectively. The ordinate axis of FIG. 6D indicates conditioned place preference test scores (CPP scores) (Example 3).

FIG. 7A is a schematic of the experimental methods for the conditioned place preference test. FIG. 7B is a plot showing conditioned place preference of mice for drug-paired places. On the X-axis, saline+saline, saline+morphine or R(−)-ketamine+morphine experimental conditions is indicated. The Y-axis shows time in seconds.

DETAILED DESCRIPTION

Figure 1:
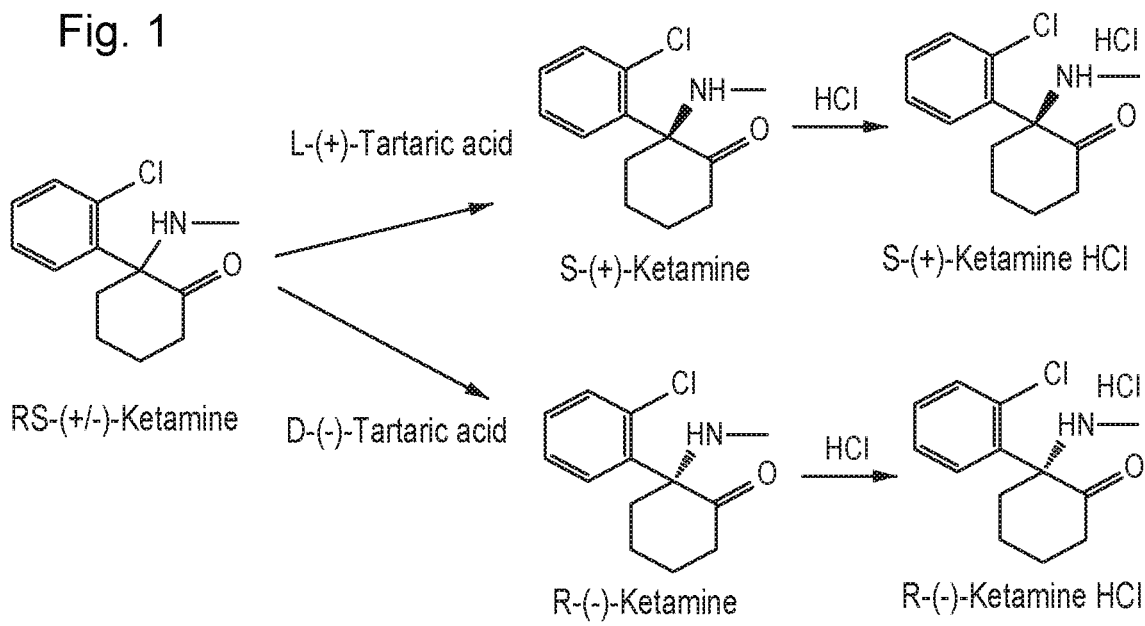
FIG. 1 is a diagram illustrating the preparation of R(−)- and S(+)-ketamine hydrochloride (Ketamine HCl) from RS(+/−)-ketamine using D(−)- and L(+)-tartaric acid (Tartaric acid), respectively.

Racemic ketamine has been shown to have potential in helping mitigate withdrawal symptoms in patients that arise after chronic opioid use (Jovaisa et al., 2006), and data from animal models have suggested that racemic ketamine might help dampen the addiction-related phenomena of drug tolerance and dependence for both opiates and ethanol (Herman et al., 1995; Khanna et al., 1993; Trujillo, 1995). However, racemic ketamine also has a number of associated problems that make it a troubling choice for administration to patients. For example, racemic ketamine is known to produce a host of effects that negatively impact patient safety. Racemic ketamine induces psychotomimetic effects, sedative and motor-impairing effects and cognitive impairment. Racemic ketamine is also itself known to be potentially addictive, making it a troubling choice for the treatment of substance use disorders (Cooper et al., 2017; Ke et al., 2018; Liu et al., 2016). In addition, racemic ketamine administration is associated with damage to the central nervous system, especially after chronic use (Wang et al., 2013). Therefore, safer alternatives to racemic ketamine are needed.

Both the S(+)-ketamine and R(−)-ketamine isomers of racemic ketamine have been tested for a variety of applications such as anesthesia and treatment of psychiatric disorders. Historically, the focus has been on S(+)-ketamine, as S(+)-ketamine has approximately 4-fold greater affinity for the NMDA receptor than R-isomer, and it is thought that racemic ketamine's ability to act as an NMDAR antagonist mediates its effects. For example, recent imaging studies in nonhuman primates suggested that (S)-ketamine, but not (R)-ketamine, increases dopamine release in the striatum, and that this release is associated with psychotomimetic effects (Hashimoto et al., 2017). In addition, S(+)-ketamine has an approximately 3- to 4-fold greater anesthetic effect as compared to R-isomer (Non Patent Literature 12). Further, S(+)-ketamine, but not R(−)-ketamine, was recently approved by the U.S. FDA as a treatment for depression.

One alternative to S(+)-ketamine or racemic ketamine is is R(−)-ketamine. The inventors have found, for the first time, that R(−)-ketamine possess properties that indicate that R(−)-ketamine functions as a superior and unexpectedly effective drug for the treatment of substance abuse disorders. The inventors have found that R(−)-ketamine can dampen withdrawal symptoms, reduce drug tolerance, and reduce drug liking. These are all factors known to contribute to the cycle of drug addiction. In addition, the inventors have found that R(−)-ketamine, unlike S(+)-ketamine, does not possess a property counter-indicated in drug abuse treatment: the production of negative mood, or anhedonia or negative affect. Further, R(−)-ketamine produces less in the way of subjective side-effects than S(+)-ketamine (Persson et al., 2002). R(−)-ketamine has also been shown to be more potent and longer-lasting than that of (S)-ketamine (Fukumoto et al., 2017; Zhang et al., 2014), and R(−)-ketamine provides an improved tolerability and safety profile (Yang et al., 2015).

Accordingly, the present invention relates to a method of treating a substance use disorder in a subject, comprising administering to the subject a therapeutically effective amount of a composition comprising R(−)-ketamine or a pharmaceutically acceptable salt thereof, wherein the composition is substantially free of S(+)-ketamine or a pharmaceutically acceptable salt thereof. The method treats a symptom of a substance use disorder, such as a withdrawal symptom, a symptom associated with susceptibility to developing a substance use disorder, a symptom associated with using a substance of a disorder. Further, the method prevents or reduces a relapse to substance use in a subject with a substance use disorder, reduces tolerance, reduces dependence or reduces preference or liking for a substance used in a substance use disorder in a subject, and improves adherence to a treatment for or increases abstinence from a substance of a substance use disorder. In some embodiments, the method can treat symptoms such as symptoms of withdrawal or psychiatric symptoms associated with the substance use disorder, reduce tolerance and/or liking, increase abstince and/or adherence to treatment, or a combination thereof.

The invention relates to an agent for the treatment of a substance use disorder, the agent consisting of R(−)-ketamine or a pharmaceutically acceptable salt thereof.

The present invention also relates to a pharmaceutical composition for the treatment of a substance use disorder, including R(−)-ketamine or a pharmaceutically acceptable salt thereof in an effective amount for reducing a symptom of a substance use disorder, and being substantially free of S(+)-ketamine or a pharmaceutically acceptable salt thereof. R(−)-ketamine or a pharmaceutically acceptable salt thereof has rapid and long-lasting effects in treating psychological symptoms associated with substance use disorders such as depression, and less side effects than the racemic mixture or S(+)-ketamine, and hence is effective for the treatment of substance use disorders. Further, R(−)-ketamine can dampen withdrawal symptoms, lessen drug tolerance and reduce drug-liking or craving, all of which are factors known to contribute to the cycle of drug addiction. R(−)-ketamine is also superior to racemic or S(+)-ketamine, in that it does not possess a property counter-indicated in substance use disorder treatment, the production of negative mood or the inability or reduced ability to feel pleasure (anhedonia or negative affect). Accordingly, the composition comprising R(−)-ketamine or a pharmaceutically acceptable salt thereof, and the pharmaceutical composition including R(−)-ketamine or a pharmaceutically acceptable salt thereof, and being substantially free of S(+)-ketamine or a pharmaceutically acceptable salt thereof are useful as novel pharmaceuticals in the field of treatment of substance use disorders.

Substances of Substance Use Disorders

The abuse of drugs is linked to their ability to produce specific subjective effects in humans (e.g., euphoria). There are many substances which can lead to a substance use disorder in a subject. As used herein, the term "drug" means a substance which may cause addiction or dependence upon continuous use. Both legal and illegal (illicit) substances can lead to substance use disorders. Included within this term are drugs such as alcohol, marijuana, synthetic cannabinoids, opioids, stimulants, barbiturates, benzodiazepines, dextromethorphan (DXM), sleep medications, khat, synthetic cathinones, cocaine, 3,4-methylenedioxymethamphetamine (MDMA), phencyclidine (PCP), lysergic acid diethylamide (LSD), psilocybin, inhalants, Rohypnol, gamma-hydroxybutyric acid (GHB), N,N-Dimethyltryptamine (DMT), ayahuasca, mescaline, salvia and nicotine. However, any substance which may cause addiction or dependence is envisaged as being within the scope of the invention.

Most substances fall within three major categories: stimulants, depressants and hallucinogens or dissociative substances. In some embodiments, in particular, but not limited to, those embodiments wherein the substance is a complex botanical product such as marijuana, the substance may have more than one active ingredient and fall into more than one of the three categories. In some embodiments, the substance may have a single active ingredient with multiple effects, and thus be classified in more than one of the three categories. In some embodiments, the substance may be classified in a single category as a stimulant, depressant, or a hallucinogenic or dissociative substance.

Depressants are substances which slow down the central nervous system, and make the subject feel relaxed, less tense, and less aware of surrounding events. Many depressants work by increasing the activity of the gamma-aminobutyric acid (GABA) neurotransmitter signaling system. Depressants such as prescription opioids and heroin can also produce effects that are similar to (but more pronounced than) those produced by the endogenous neurotransmitters endorphin and enkephalin. Examples of depressants include, but are not limited to, alcohol, heroin, sleeping pills, barbiturates, benzodiazepines and opioids.

Conversely, stimulants act to make the subject feel more alert and increase the subject's physical energy. Some stimulants can also lead to feelings of happiness, sociability, improved attention and decreased appetite or a combination thereof. Some stimulants are used in the treatment of psychiatric disorders. For example, methylphenidate is used to treat Attention Deficit Hyperactivity Disorder. Many stimulants work, at least in part, by increasing the levels of the dopamine signaling in the central nervous system. For example, cocaine use increases the amount of available dopamine in the brain, which leads to mood elevation and feelings of euphoria. Cocaine also produces changes in the norepinephrine and glutamate systems. Exemplary stimulants include, but are not limited to, cocaine and amphetamines.

Hallucinogenic or dissociative substances alter the perception, thoughts and/or feelings of a subject. Hallucinogens cause hallucinations, which are sensations or images that seem to be real to the individual, even though they are not. Some hallucinogens function by temporarily disrupting chemical communication between the brain and spinal cord.

Some hallucinogens interfere with serotonin signaling, which is known to regulate mood, sensory perception, sleep, hunger, body temperature, sexual behavior and muscle control. Some hallucinogens interfere with glutamate signaling, which regulates pain perception, responses to the environment, emotions, learning and memory. Exemplary, but non-limiting hallucinogens comprise Ayahuasca, N,N-Dimethyltryptamine (DMT), lysergic acid diethylamide (LSD), peyote, psilocybin and dextromethorphan (DXM).

There are many mechanisms by which substances can alter the mental state of a subject. Frequently, substances act to alter neuronal function and mental state by altering one or more neurotransmitter systems in the body. Some substances mimic natural neurotransmitters and engage with the cognate receptors for those neurotransmitters in the central nervous system of the subject. For example, opioid drugs such as heroin mimic natural opioids and bind to opioid receptors. However, heroin stimulates the activity of p-opioid receptors more strongly than natural opioids. Marijuana mimics cannabinoid neurotransmitters. Nicotine attaches to receptors for acetylcholine, a naturally occurring cholinergic neurotransmitter. Alternatively, or in addition, substances can alter neurotransmission by interacting with and altering the function of molecules or proteins other than receptors that are involved in neurotransmission. Non-limiting examples comprise proteins involved in receptor recycling to the cell surface, neurotransmitter reuptake, or protein transport at the synapse. Further, substances can increase or decrease the level of receptors at the synapse, bind to proteins that affect the levels of neurotransmitters at the synapse such as transporters, or modulate neuronal response to naturally occurring neurotransmitters, as well as other mechanisms.

Substances of the disclosure can be naturally occurring, for example purified from a plant, animal or fungal source (marijuana, tobacco, e.g.), can be synthetic (synthetic cathinones, LSD, e.g.), or a combination thereof. A substance of the disclosure can be a synthetic version of substance originally purified from a natural source. A list of exemplary, but non-limiting substances of the disclosure is set forth in Table 1. All substances, and all biological mechanisms, capable of inducing a substance use disorder in a subject are envisaged as within the scope of the present invention.

TABLE 1

List of Substances that can lead to substance use disorders

| Name | Brand Name ® | Additional Names/Information |
|---|---|---|
| Depressants | | |
| alcohol | | Ethanol |
| phenobarbital | Luminal | (barbiturate) |
| pentobarbital | Nembutal | (barbiturate) |
| methohexital | Brevital, Brietal | (barbiturate) |
| butabarbital | Butisol | (barbiturate) |
| butalbital | Fioricet (with acetaminophen and caffeine) | (barbiturate) |
| alprazolam | Xanax, Alprazolam Intensol | (benzodiazepine) |
| chlorodiazepoxide | Librium | (benzodiazepine) |
| diazepam | Valium, Diastat, Diazepam Intensol | (benzodiazepine) |
| lorazepam | Ativan, Lorazepam Intensol | (benzodiazepine) |
| triazolam | Halcion | (benzodiazepine) |
| Rohypnol | Flunitrazepam, Rohypnol | (benzodiazepine) |
| eszopiclone | Lunesta | (sleep medication) |
| zaleplon | Sonata | (sleep medication) |
| zolpidem | Ambien, Edluar, Intermezzo, Zolpimist | (sleep medication) |
| GHB, Gamma-hydroxybutyrate | Xyrem | γ-Hydroxybutyric acid, 4-hydroxybutanoic acid; sodium oxybate |
| Hallucinogens and Dissociatives | | |
| ayahusca | | *Psychotria viridis* |
| DMT | | N,N-Dimethyltryptamine |
| LSD | | D-lysergic acid diethylamide |
| mescaline | | (3,4,5-trimethoxyphenethylamine; Peyote - Cactaceae family |
| psilocybin | | psilocybin mushrooms |
| salvia | | *Salvia divinorum* |
| PCP | | Phencyclidine; 1-(1-Phenylcyclohexyl)piperidine |
| DXM | Wal-Tussin Cough, Creomulsion, Vicks DayQuil Cough, Cough DM ER, Tussin Cough, Cough Relief, Robitussin ER, Delsym, Scot-Tussin Diabetes CF | Dextromethorphan |
| Kratom | | *Mitragyna speciosa* |
| Stimulants | | |
| cocaine | | from *Erythroxylon coca* |
| Amphetamine | Adderall, Benzedrine, Evekeo | Amphetamine sulfate |
| Methamphetamine | Desozyn | |
| Dextroamphetamine | ProCentra, Dexedrine Spansule, Zenzedi, Adderall, Benzedrine, Evekeo | |

TABLE 1-continued

List of Substances that can lead to substance use disorders

| Name | Brand Name ® | Additional Names/Information |
|---|---|---|
| Levoamphetamine | Adderall, Benzedrine, Evekeo | |
| Lisdexamfetamine | Vyvanse | |
| Atomoxetine | Strattera | |
| Methylphenidate | Concerta, Ritalin, Daytrana, Methylin, Metadate, Aptensio, Quillivant | |
| Dexmethylphenidate | Focalin, FocalinXR | |
| Oxymetazoline | Afrin, Duamist, Mucinex, Nasacon, Nasin, Ocuclear, Drixine | |
| Pseudoephedrine | Sudafed, Valu-Tapp, Sinus 12 Hour, Wal-phed, Suphedrin | |
| Phenylephrine | Preparation H, Vazculep | |
| Opioids | | |
| Heroin | | from poppy, *papaver somniferum*; aka diamorphine |
| mitragynine | | from *Mitragyna speciosa* |
| Codeine | | (5α,6α)-7,8-didehydro-4,5-epoxy-3-methoxy-17-methylmorphinan-6-ol |
| Fentanyl | Actiq, Duragesic, Sublimaze, Subsys, Abstral, Ionsys | |
| Hydrocodone, dihydrocodeinone | Vicodin, Norco, Zohydro, Lorcet, Hycet, Zamicet, Xodol | |
| Hydromorphone | Dilaudid, Exalgo ER | |
| Meperidine | Demerol | |
| Methadone | Dolophine, Methadose | |
| Morphine | Duramorph, MS Contin, Infumorph P/F, Arymo, Astramorph-PF | |
| Oxycodone | Oxycontin, Roxicodone, Percodan, Percocet | |
| Oxymorphone | Opana | |
| Inhalants | | |
| aerosols | | e.g. spray deodorants, hair spray, insect repellant |
| gases | | e.g. nitrous oxide |
| solvents | | e.g. toluene, gasoline, paint thinner, dry cleaning fluids |
| nitrites | | e.g. isoamyl nitrite, isobutyl nitrite, cyclohexyl nitrite |
| Other/Mixed Classification | | |
| Marijuana | | *Cannabis sativa* |
| synthetic marijuana | | |
| cannabicyclohexanol | | |
| THC | Marinol, Syndros | delta-9-tetrahydrocannabinol; Dronabinol; from *Cannabis sativa* |
| MDMA | | 3,4-methylenedioxy-methamphetamine |
| Loperamide | Immodium | 4-[4-(4-chlorophenyl)-4-hydroxypiperidin-1-yl]-N,N-dimethyl-2,2-diphenylbutanamide |
| Khat | | *Catha edulis* |
| mephedrone | | 4-methyl methcathinone or 4-methyl ephedrone, |
| methylone | | 2-Methylamino-1-(3,4-methylenedioxyphenyl)propan-1-one; MDMC |
| MDPV | | 3,4-methylenedioxypyrovalerone |
| tobacco | | *Nicotiana* |
| Nicotine | Nioctrol, Nicoderm | 3-(1-methyl-2-pyrrolidinyl)pyridine |

Substance Use Disorders

Substance use disorders are characterized by progressively uncontrollable substance use that persists in spite of negative consequences (e.g., social, economic and/or medical consequences). Substance use disorders are marked by a transition from substance use that is well controlled, to a use that is unregulated and destructive. This transition can be abrupt or progressive in nature. Substance use disorders are characterized by addiction, or dependence, upon the substance. When a subject is dependent upon, or addicted to, a substance, this means that there is a physical, physiological or psychological reaction and/or interaction of the substance and the subject, which results in the subject exhibiting or having a forced or compulsive use of the substance without a recognized purpose or need for treating a disease. Rather, the purpose is that of achieving the desired effect, and/or avoiding withdrawal symptoms as defined hereinafter, which occur when the substance is discontinued or the amount used is reduced. Substance use disorders are sometimes referred to as "substance abuse", and the substance or substances to which the subject is addicted or dependent upon are "abused", for example opioid abuse or alcohol abuse.

With dependence upon a substance come a host of symptoms that work to perpetuate that dependence, and complicate curing or otherwise managing problematic substance use. For example, in many cases subjects addicted to a substance develop an increased tolerance to the substance. Tolerance frequently leads to increased substance use to attempt to compensate for the diminished effects of the substance that can result from tolerance. Additional complicating symptoms include withdrawal symptoms that occur when use of the substance is stopped or reduced, cravings, reduced motivation for other reward stimuli, an increased sensitivity to stressful stimuli, a heightened sensitivity or responsivity to substance related cues, impulsivity, an inability to accurately evaluate delayed rewards, and a lack of motivation to change destructive behaviors, such as those caused by substance use.

In some embodiments, the symptoms that work to perpetuate substance use disorder in an individual result from changes in the brain that are caused by repeated substance use. Alternatively, or in addition, symptoms, such as impulsivity and stress sensitivity, may be present in an individual before the development of a substance use disorder, and contribute to the susceptibility of that individual to substance use disorders. Genetic, environmental and psychiatric factors may all also contribute to an individual's vulnerability to developing a substance use disorder.

In some embodiments, substance use disorders are connected to mood disorders, anxiety disorders or obsessive-compulsive disorder. For example, NIDA, the National Institute on Drug Abuse, indicates that subjects diagnosed with mood disorders are twice as likely to abuse substances as subjects without mood disorders. The combination of loss of reward function and recruitment of brain stress systems provides a powerful neurochemical basis for a negative emotional state that is responsible for the negative reinforcement driving, at least in part, the compulsivity of addiction. As use herein, "mood disorders" refer to refer to mental health disorders with a serious change in mood. Exemplary mood disorders include, but are not limited to major depressive disorder, bipolar disorder, dementia, low motivation, anxiety, insomnia, anorexia, obsessive compulsive disorder, post traumatic stress disorder, persistent depressive disorder, cyclothymia and seasonal affective disorder. Symptoms of mood disorders include, but are not limited to, anhedonia or negative affect, mood depression, low motivation, anxiety, insomnia, anorexia, impulsivity and stress sensitivity.

One particularly acute set of substance use disorders are opioid based substance use disorders. There is a devastating opioid use and overdose crisis in the United States. It has been reported that approximately 25.5 million adults suffer pain and opioids that are often prescribed for their treatment can lead to opioid misuse and dependence. It has also been reported that more than 2 million Americans have opioid use disorders (OUDs) and many started their addiction with prescribed opioids. One of the most devastating consequences of opioid misuse is opioid overdose, which can produce respiratory depression and death. Drug overdose is the leading cause of accidental death in the US, with an estimation of 60,000 deaths in 2016; 20,101 overdose deaths related to prescription pain relievers, and 12,990 overdose deaths related to heroin.

Although there are safe and effective pharmacotherapies for opioid use disorders and to prevent/reverse overdose, their use has some limitation or they are largely underutilized. Methadone and buprenorphine are approved by the FDA to treat opioid use disorders (OUDs) but long term efficacy and treatment adherence are sub-optimal. Naltrexone is approved by the FDA to prevent opioid use relapse in people with no physical dependence to opioids but initiation and adherence to treatment are low. Naloxone (Narcan) is approved to reverse opioid overdose but it has a short action, may precipitate opioid withdrawal, and put the person at risk of overdose. Lofexidine is the only drug to be FDA approved for helping mitigate opioid withdrawal symptoms. However, it only treats the physical symptoms and does not address the psychological components of drug withdrawal. Other medications such as gabapentin, pregabalin, buprenorphine, cannabinoids, ketamine, and ultra-low doses of oral naltrexone, as well as rapid opioid withdrawal under anesthesia have been evaluated but the results are inconclusive. There thus exists a need for additional treatments for opioid use disorders. The disclosure provides compositions comprising R(−)-ketamine and methods of treatments that can meet this need.

Neurobiology

Multiple neurotransmitter systems have been implicated in substance use disorders. Exemplary neurotransmitters include, but are not limited to, monoamines (such as dopamine, serotonin and noradrenaline), norepinephrine, endogenous opioids (e.g. endorphin and enkephalin), acetylcholine, endogenous cannabinoids (endocannabinoids, e.g. anandamide), glutamate and Gamma-aminobutyric acid (GABA). In some embodiments, a substance use disorder may affect a single neurotransmitter system. In some embodiments, one or more neurotransmitter systems may be affected by the substance use disorder. For example, alcohol interacts with several neurotransmitter systems in the brain, including the inhibitory neurotransmitter GABA, glutamate, and others, to produce euphoria, impair motor function and reduce anxiety.

In some embodiments, a substance affects dopamine neurotransmitter signaling in the central nervous system of a subject with a substance use disorder. Exemplary dopamine functions comprise processing pleasure and reward, movement, attention and memory. Dopamine is found in the midbrain, the ventral tegmental area (VTA), the cerebral cortex and the hypothalamus. Exemplary substances that affect dopamine transmission include, but are not limited to, cocaine, methamphetamine and amphetamine. Further, virtually all substances of abuse directly or indirectly augment dopamine in the reward pathway. Over activating dopamine signaling through substance use can produce feelings of pleasure and euphoria. However, over activating dopamine signaling can result in substance-induced neuroplasticity by raising the threshold required for dopamine cell activation and dopamine signaling. Long term, this leads to decreases in D2 receptors and dopamine release, ultimately leading to reduced regional activity in areas of the brain such as the cingulate gyrus (involved in inhibitory control and impulsivity) and prefrontal cortex (involved in executive function). Over activating dopamine can also change the saliency of various reward pathways in the brain. This can lead to symptoms such as depression, impulsivity or aberrant reward processing.

In some embodiments, a substance affects serotonin neurotransmitter signaling in the central nervous system of a subject with a substance use disorder. Exemplary serotonin functions comprise the regulation of mood, sleep, sexual desire and appetite. Serotonin is found in the midbrain, the VTA, the cerebral cortex and the hypothalamus. MDMA, LSD and cocaine are non-limiting examples of substances that affect serotonin neurotransmission.

In some embodiments, a substance affects norepinephrine neurotransmitter signaling in the brain of a subject with a substance use disorder. Exemplary norepinephrine functions comprise in sensory processing, movement, sleep, mood, memory and anxiety. Norepinephrine is found in the midbrain, the VTA, the cerebral cortex and the hypothalamus. Cocaine, methamphetamine, and amphetamine are examples of substances that affect norepinephrine neurotransmission.

In some embodiments, a substance affects endogenous opioid (e.g. endorphin and encephalin) neurotransmitter signaling in the central nervous system of a subject with a substance use disorder. Endogenous opioid neurotransmitters are widely distributed in the brain and spinal cord, and bind to a variety of receptors. Exemplary endogenous opioid functions comprise are roles in analgesia and sedation, regulating the rate of bodily functions such as breathing, and regulating mood. Opioids such as heroin, morphine and prescription pain relievers are examples of substances that affect endogenous opioid neurotransmission.

In some embodiments, a substance affects cholinergic neurotransmitter signaling, such as acetylcholine neurotransmission, in the central nervous system of a subject with a substance use disorder. Acetylcholine is found in the hippocampus, cerebral cortex, thalamus, basal ganglia and cerebellum. Exemplary acetylcholine functions comprise movement, and cognition and memory. An exemplary, but non-limiting, substance that affects acetylcholine neurotransmission is nicotine. Nicotine binds to receptors for acetylcholine.

In some embodiments, a substance affects endogenous cannabinoid (e.g. anandamide) neurotransmitter signaling in the central nervous system of a subject with a substance use disorder. Endogenous cannabinoids are found in the cerebral cortex, hippocampus, thalamus and basal ganglia. Exemplary endogenous cannabinoid functions comprise regulating movement, cognition and memory. An exemplary, but non-limiting substance that affects endogenous cannabinoid neurotransmission is marijuana.

In some embodiments, a substance affects glutamate neurotransmitter signaling in the central nervous system of a subject with a substance use disorder. Glutamate is widely distributed in the brain. Exemplary glutamate functions comprise regulating the rate of neuronal activity (increasing the rate), learning, cognition and memory. Ketamine, phencyclidine and alcohol are non-limiting examples of substances that affect glutamate neurotransmission.

In some embodiments, a substance affects gamma aminobutyric acid (GABA) neurotransmitter signaling in the central nervous system of a subject with a substance use disorder. GABA is widely distributed in the brain. Exemplary GABA functions comprise regulating the rate of neuronal activity (decreasing the rate), anxiety, memory and anesthesia. Sedatives, tranquilizers and alcohol are examples of substances that affect GABA neurotransmission.

Changes in the brain that are linked to substance disorders are referred to as adaptation or neuroadaptation, as the nervous system adapts to repeated use of the substance. These changes may comprise changes in the expression or levels of neurotransmitter receptors, changes in the expression or levels of neurotransmitters, changes to neuronal structure, changes in neural connectivity or a combination thereof. Neuroadaptation is linked to the development of tolerance, wherein the reaction of an individual to a substance is reduced with repeated use. One example of this phenomenon is the downregulation of the p-opioid receptor in opioid users. Other receptor-based adaptations comprise changes to glutamate receptors such as the N-methyl-D-aspartate (NMDA) receptor, serotonergic receptors and dopaminergic receptors. Changes in these receptors may be involved in withdrawal symptoms as well as other symptoms associated with substance use disorders. Adaption to substance use is believed to contribute to many of the symptoms that make substance use disorders so difficult to treat. These symptoms include, but are limited to, tolerance, withdrawal, cravings, a heightened sensitivity to substance related cues, stress sensitivity, and low motivation to change destructive behaviors such as substance use, anxiety, irritability, difficulty concentrating, difficulty thinking clearly, mood swings, nightmares, depression, tension, panic attacks, short term memory loss, restlessness, a feeling of helplessness, stress-sensitivity, aberrant reward processing or a combination thereof.

Regions of the central nervous system that can be disrupted with substance use disorders and/or undergo adaptation caused by substance use include, but are not limited to, the midbrain, the ventral tegmental area (VTA), cerebral cortex, prefrontal cortex, hypothalamus, thalamus, hippocampus, basal ganglia, extended amygdala and cerebellum. Functions of the midbrain include, but are not limited to, contributing to motor control, visual and auditory processing, control of sleep/wake cycles, arousal and temperature regulation. Functions of the VTA include, but are not limited to, its role in two major dopamine pathways, the mesolimbic pathway, which connects the VTA to the nucleus accumbens, and the mesocortical pathway, which connects the VTA to the frontal lobes. The cerebral cortex is connected to various subcortical structures, such as the thalamus and basal ganglia. Functions of the cerebral cortex include, but are not limited to, contributing to motor and sensory processing, speech, memory, executive function, personality and social behavior. Functions of the prefrontal cortex, which is a part of the cerebral cortex, include, but are not limited to, contributing to higher cognitive functions such as anticipation, judgement, planning and decision making. Functions of the hypothalamus, include, but are not limited to, contributing to maintaining homeostasis of the autonomic nervous system, motivation and emotion. Functions of the thalamus include, but are not limited to, relaying sensory and motor signals and contributing to the regulation of consciousness, sleep and alertness. Functions of the hippocampus include, but are not limited to, regulating emotions and memory. Functions of the basal ganglia, include, but are not limited to, an involvement motor control, executive functions and behaviors, regulating mood, reward circuitry and learning. Functions of the extended amygdala include, but are not limited to, its role in processing emotions such as fear, stress, anxiety, irritability, anger and pleasure, as well as roles in motivation, arousal and memory. Functions of the cerebellum include, but are not limited to, receiving sensory information from the spinal cord and regulating motor movements, such as those involved in balance and coordination.

Symptoms Associated with Substance Use Disorders

The symptoms of a substance use disorder depend upon the substance used, the duration and amount of use, and the subject. These symptoms can be physical or psychological in nature, or a combination thereof. Physical symptoms of substance use include, but are not limited to, tremors, insomnia, disturbed sleep, headache, sweating, nausea, vomiting, muscle pain, muscle stiffness, hypertension, irregular heart rate, elevated heart rate, heart palpitations, dizziness, shakiness, tremors, seizures, dehydration, shallow breathing, fatigue, loss of appetite, clammy skin, loss of color or a combination thereof. Psychological symptoms of substance use include, but are not limited to, anxiety, irritability, difficulty concentrating, difficulty thinking clearly, mood swings, nightmares, depression, tension, panic attacks, short term memory loss, restlessness, a feeling of helplessness, stress-sensitivity, a heightened responsivity to substance-related cues, aberrant reward processing, craving or a combination thereof.

Figure 8:
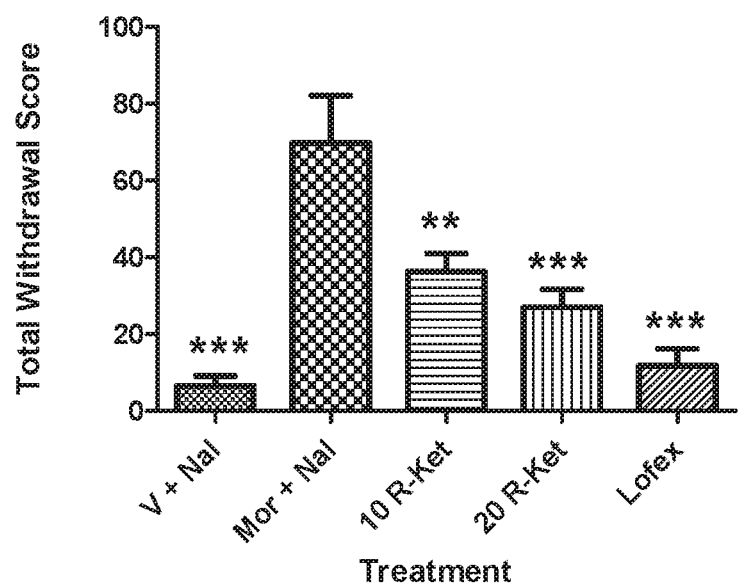
FIG. 8 is a plot showing that R(−)-ketamine attenuates withdrawal signs from naloxone-precipitated withdrawal from subchronic morphine in rats. R(−)-ketamine (10 and 20 mg/kg, administered intraperitoneally (i.p.)) dose-dependently attenuated overall morphine withdrawal scores in rats. Data are mean+/−SEM for 8 rats/group. $F(4,39)=14.2$, $p<0.001$. The approved opioid withdrawal drug lofexidine (0.25 mg/kg, i.p.) was also effective.  $p<0.01$; * $p<0.001$ compared to Morphine+Naloxone (morphine withdrawal without ketamine or lofexidine).

Withdrawal is associated substance use disorders of the disclosure. Withdrawal occurs when a subject accustomed to a relatively stable level of a substance is suddenly deprived of that substance. Withdrawal symptoms may be physical or psychological in nature, or a combination thereof. The specific withdrawal symptoms may depend on the substance being withdrawn from, the amount and duration of substance use, and the individual. Withdrawal symptoms may be immediate or delayed in onset. Physical symptoms of withdrawal include, but are not limited to, tremors, insomnia, disturbed sleep, headache, sweating, nausea, vomiting, muscle pain, muscle stiffness, hypertension, irregular heart rate, elevated heart rate, heart palpitations, dizziness, shakiness, tremors, seizures, dehydration, shallow breathing, fatigue, loss of appetite, clammy skin, loss of color or a combination thereof. Psychological symptoms of withdrawal include, but are not limited to, anxiety, irritability, difficulty concentrating, difficulty thinking clearly, mood swings, nightmares, depression, tension, panic attacks, short term memory loss, restlessness, a feeling of helplessness, stress-sensitivity, a heightened responsivity to substance-related cues, aberrant reward processing, craving (the substance being withdrawn from) or a combination thereof. In some embodiments, administering a therapeutically effective amount of a composition comprising R(−) ketamine of the disclosure reduces or prevents withdrawal symptoms from substances such as alcohol and opioids. For example, administration of R(−)-ketamine to rats reduces opioid withdrawal symptoms (FIG. 8).

Figure 9:
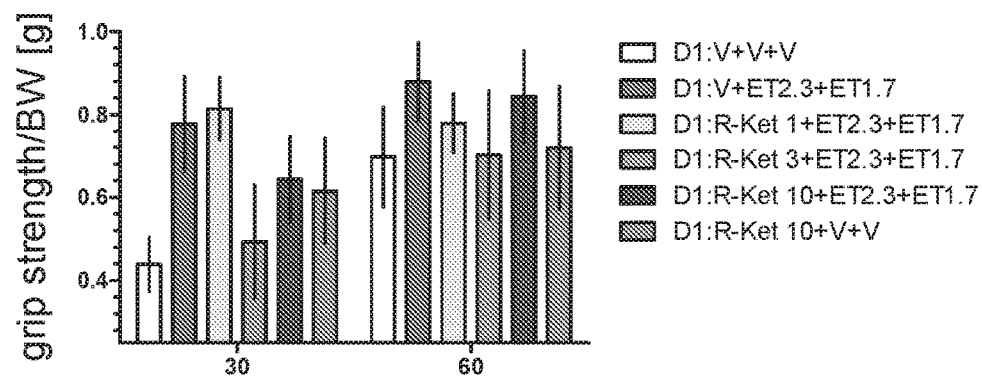
FIG. 9 is a plot showing that R(−)-ketamine significantly attenuates tolerance development to ethanol. The effects of ethanol alone are shown on the measure of grip strength/body weight on day 2 after various treatments on day 1. When high dose ethanol was not given on day 1, grip strength on day two of ethanol treatment was low. Tolerance to this effect on grip strength was demonstrated (compare first and second bars at 30 min post ethanol). When R(−)-ketamine (3 mg/kg) was given with ethanol on day 1, the tolerance was significantly diminished (compare second and fourth bars at 30 minutes). On the X axis, left to right, rats with the following dosing regimens were measured at each of 30 minutes post dosing and 60 minutes post dosing: D1: V+V+V; D1: V+ET2.3+ET1.7; D1: R-KET1+ET2.3+ET1.7; D1: R-KET3+ET2.3+ET1.7; D1: R-KET10+ET2.3+ET1.7; D1: R-KET1+V+V7. V=vehicle alone, ET2.3=2.3 mg/kg ethanol administered intraperitoneally (i.p.), ET1.7=1.7 mg/kg ethanol administered i.p., R-KET1=R(−)-ketamine administered at 1 mg/kg, R-KET3=R(−)-ketamine administered at 3 mg/kg, R-KET10=R(−)-ketamine administered at 10 mg/kg.

Tolerance is associated with substance use disorders of the disclosure. Tolerance occurs when an individual develops a reduced response to a substance with repeated use. The development of tolerance frequently leads to the individual taking increasing amounts of the substance, in an attempt to recreate the effect of the substance before tolerance developed. In some embodiments, administering a therapeutically effective amount of a composition comprising R(−) ketamine of the disclosure can decrease tolerance to substances such as alcohol and opioids. For example, administration of R(−)-ketamine to rats decreased tolerance to alcohol (FIG. 9). By blocking tolerance, R(−)-ketamine compositions and methods of the disclosure reduce the amount of substance consumed. For example, reducing alcohol tolerance by administering R(−)-ketamine would prevent drinkers from increasing the amount of alcohol consumed and thereby decrease the likelihood of developing dependence. In some embodiments, R(−)-ketamine reduces the tolerance development to alcohol thereby reducing the risk of alcohol dependence.

Craving is a symptom associated with substance use disorders of the disclosure. Craving denotes a heightened desire for a substance. Craving is often coupled to a difficulty in experiencing a cue, such as an environmental cue, without incurring a high level of desire for the substance. Craving can also include repeated failures to resist the urge to use the substance, and intolerable mental or physical states in the absence of substance use. In some cases craving may be treated by the administration of an agonist (a substitution therapy). Exemplary but non-limiting examples of this approach comprise the administration of methadone for opioid craving, varenicline for nicotine craving, Dronabinol, nabilone and THC analogs for cannabis craving, and stimulants such as amphetamines for cravings for cocaine.

A heightened responsivity to substance related cues is a symptom associated with substance use disorders of the disclosure. Cue reactivity is a learned response, in which individuals with substance dependence develop physiological and/or subjective responses when presented with substance related stimuli. These stimuli can include, but are not limited to, cigarettes (tobacco), bottles of alcohol (alcohol) or drug paraphernalia. A heightened sensitivity to substance related cues can be a component of craving. Cue reactivity has been linked to increased activity in the amygdala, ventral striatum and prefrontal regions.

Aberrant reward processing is a symptom associated with substance use disorders of the disclosure. Reward salience, sometimes called incentive salience, is a motivation that a subject develops through the association of a stimulus and a reward (e.g., substance use, and a pleasurable feeling). In substance use disorders, normal reward salience is disrupted. The subject has low motivation for non-substance rewards, and a disproportionately high motivation for substance-based rewards. Dopamine signaling is a key component of the reward system, and the aberrant reward processing seen in substance use disorders often involves reduced dopamine signaling.

A feeling of helplessness, or powerlessness, is a symptom associated with substance use disorders of the disclosure. In some embodiments, the feeling of helplessness is learned helplessness. In learned helplessness, the subject with the substance use disorder feels powerless over their use of the substance and ceases try to treat their substance use disorder. In some embodiments, the feeling of helplessness precedes the substance use disorder, and contributes to the vulnerability of the subject in developing a substance use disorder. In some embodiments, the feeling of helplessness both precedes the substance use disorder and is exacerbated by the substance use disorder.

A heightened sensitivity to stress ("stress sensitivity") is a symptom associated with substance use disorders of the disclosure. Stress is a well known risk factor in the development of substance use disorders, and in the relapse of subjects who had previously managed to stop using a substance. Common stressors include early life (childhood) stress, economic stress and chronic or acute adverse life events. Stress is also associated with a variety of psychiatric disorders, such as mood and anxiety disorders, as well as post-traumatic stress disorder. Stress can lead to the release of hormones such as adrenaline, cortisol and norepinephrine, which can directly or indirectly alter neurotransmitter signaling in the central nervous system. For example, stress can reduce the levels of serotonin and dopamine in the brain. In some embodiments, stress sensitivity may precede the development of a substance use disorder and contribute to susceptibility of the individual to developing the substance use disorder. For example, the substance abuse disorder may develop as a coping strategy (e.g., a self-medicating strategy) to treat stress. In some embodiments, stress sensitivity is a symptom caused by the substance use disorder. For example, the substance use disorder may cause more stress, and a heightened sensitivity to stress. In some embodiments, stress sensitivity both precedes the development of the substance use disorder, and is a symptom caused by the substance use disorder.

Anhedonia and negative affect are symptoms associated with substance use disorders of the disclosure. As used herein, anhedonia, a clinical feature of mood disorders such as depression and bipolar disorder, refers to the reduction or loss of the capacity to experience pleasure. Negative affect refers to a preponderance of negative moods and emotions in a subject that are counter to well being. Anhedonia and negative affect are thought to be key factors involved in both relapse and the transition from recreation to excessive substance use. Without wishing to be bound by theory, anhedonia and negative affect are thought to originate in the dopaminergic mesolimbic and mesocortical reward circuit. Surprisingly, the R(−)-ketamine compositions and methods of the disclosure do not induce anhedonia or negative affect. Since subjects experience anhedonia and negative affect both while abusing substances in substance use disorders and while attempting to stop substance abuse, treatments that do not in and of themselves create or exacerbate anhedonia or negative affect are preferred and more effective treatments for substance use disorders.

Figure 6A:
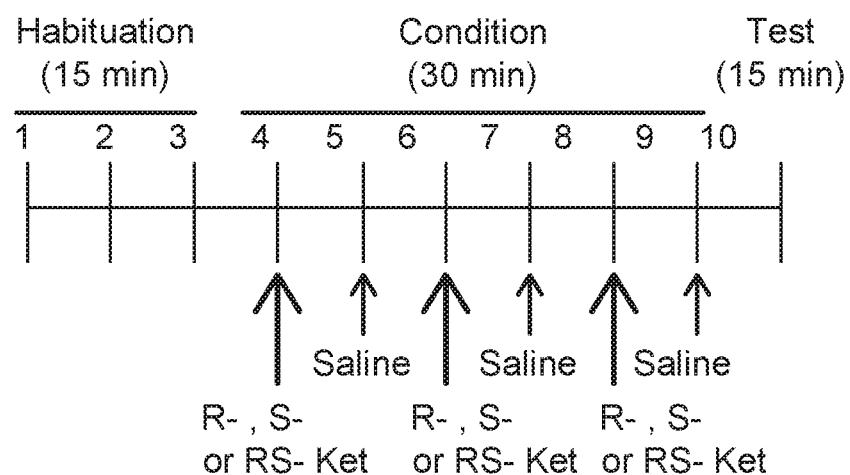
FIG. 6A is a diagram illustrating a test protocol for investigating rewarding effects of R(−)-ketamine, S(+)-ketamine, and RS(+/−)-ketamine on the control mice using a conditioned place preference test. 15-minute habituation was performed for 3 days. Then, 30-minute conditioning was performed on day 4 to day 10, and a behavioral evaluation test was performed on day 11. Saline was injected on day 5, day 7, and day 9.
Figure 6B:
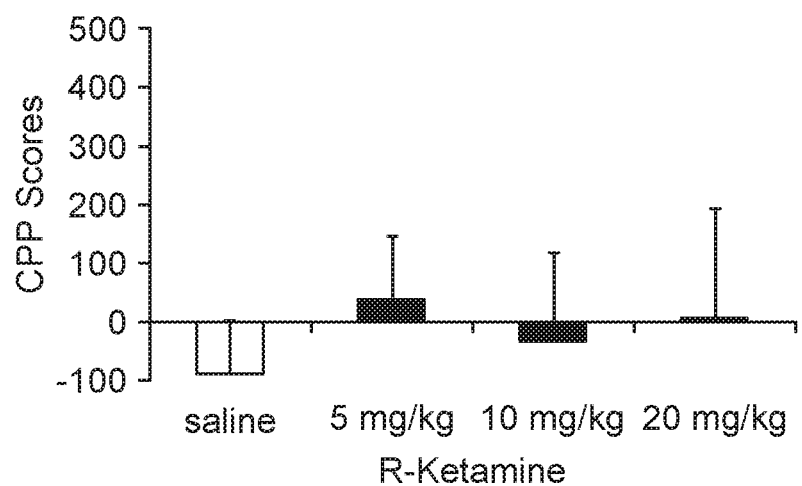
FIG. 6B is a graph showing results of the rewarding effects of R(−)-ketamine on the control mice using the conditioned place preference test.

One model of anhedia and negative affect is an intracranial self-stimulation assay (ICSS) as described herein. ICSS has considerable predictive validity as a measure of the negative affective state, for example as a component of nicotine withdrawal (Muelken, P. et al, A Two-Day Continuous Nicotine Infusion Is Sufficient to Demonstrate Nicotine Withdrawal in Rats as Measured Using Intracranial Self-Stimulation (2015) PLoS ONE 10(12): e0144553). In brief, rats are implanted with electrodes directed at the rewarding brain area, such as the medial forebrain bundle, and are allowed to deliver current to this brain area by depressing a response lever. The effect of changing the current frequency on behavior alone (vehicle) and in the presence of a substance of abuse with and without R(−)-ketamine can then be observed. The ICSS data with R(−)-ketamine, S(+)-ketamine and R-hydroxynorketamine (FIGS. 10-12) demonstrate that R(−)-ketamine is superior as a treatment for substance use disorders compared to other treatments, such as S(+)-ketamine or racemic ketamine comprising S(+)-ketamine, which can produce anhedonic responses and negative affect in subjects. The preclinical data presented here thus predicts a superior profile for R(−)-ketamine over either racemic R,S-ketamine or of S(+)-ketamine in the treatment of substance use disorders. Racemic ketamine produces a host of physiological and behavioral changes that are opposite in direction from those needed for patients undergoing treatment for substance use disorders. These include dissociative reactions and the symptoms of schizophrenia (Krystal et al., 1994). Importantly, racemic ketamine produces a negative impact on mood symptoms (Nugent et al., 2018). In contrast to S(+)-ketamine, that produces psychotic symptoms, R(−)-ketamine engenders a state of relaxation in humans (Vollenweider et al., 1997). Depression and anxiety symptoms in subjects with substance use disorders, especially in subjects undergoing treatment, exacerbate rather than mitigate the probability of relapse to substance use (Hatzigiakoumis et al., 2011; Krupitsky et al., 2016; Nunes et al., 2004). In contrast to racemic ketamine and S(+)-ketamine (FIG. 11), neither R-ketamine (FIG. 10) nor its metabolite (FIG. 12) produce negative mood symptoms. Furthermore, unlike substances of abuse such as morphine (FIG. 7B), racemic ketamine (FIG. 6D) or S(+)-Ketamine (FIG. 6C), R(−)-ketamine (FIG. 6B) does not produce rewarding effects.

Substance use disorders include behaviors that are locked into addictive patterns that are not awareness driven or life-goal-oriented (Bell, 1995). Denial of addiction is another barrier to treatment and recovery (Vayr et al., 2019). Awareness training and mindfulness therapies have been associated with improved outcomes in substance abuse disorder (Perry, 2019). Without wishing to be bound by theory, it is thought that increased awareness and introspection induced by states of relaxation by R(−)- but not by S-(+)-ketamine (Vollenweider et al., 1997) provide an additional mechanism by which R(−)-ketamine adds therapeutic value in substance use disorder treatment. In some embodiments, the R(−)-ketamine compositions and methods of the instant disclosure increase self awareness and introspection, thereby treating substance use disorders.

Mood and anxiety disorders are psychiatric disorders that are frequently comorbid with substance use disorders of the disclosure. Substance use disorders involve dysregulation of motivational circuits such as the dopamine reward circuitry, which are also implicated in mood and anxiety disorders. Substance use disorders also involve three major neurobiological circuits, the basal ganglia, the extended amygdala and the prefrontal cortex, which have also been implicated in mood and anxiety disorders. Mood disorders and anxiety disorders involve changes in a subject's mood. Exemplary mood disorders and anxiety disorders comprise depression, bipolar disorder, anxiety disorder, obsessive compulsive disorder and post-traumatic stress disorder. Signs of depression include, but are not limited to, a lack of interest in activities, changes in sleep pattern, changes in appetite, feelings of guilt, feelings of despair, lack of energy, trouble concentrating, stress, low mood, impaired motivation, cognitive impairment, diminished ability to think, anxiety, insomnia, anhedonia or negative affect, anorexia, fatigue and suicidal thoughts. Signs of anxiety include, but are not limited to, worry, distress, fear and panic attacks. Signs of bipolar disorder include, but are not limited to, drastic changes in mood, behavior and energy, sometimes termed episodes. Episodes can be manic, depressive or mixed. Bipolar disorder is also characterized mood swings. In some embodiments, substance use disorders can be thought of as involving three stages in a recurring cycle: (1) binge/intoxication, (2) withdrawal/negative affect, and (3) preoccupation/anticipation (craving). This cycle can worsen over over time, and involves neuroplastic changes in the brain reward, stress, and executive function systems. Substance use disorders can also be thought of as chronically relapsing disorders, wherein shifts from impulsivity to compulsivity drive substance consumption. Thus substance use disorders comprise symptoms also seen in obsessive-compulsive disorders. Obsessive-compulsive disorder is an anxiety disorder involving obsessions and compulsions.

Mood swings are a symptom associated with substance use disorders of the disclosure, and with bipolar disorder. Mood swings are an abrupt, extreme and apparently unaccountable change in mood. For example, an abrupt switch from feelings of happiness to depression with no or little external basis constitutes a mood swing.

Panic attacks are a symptom associated with substance use disorders of the disclosure. A panic attack is a sudden feeling of intense fear or panic in a situation in which there is no frightening stimulus that could explain the feeling. Panic attacks are symptoms associated both with anxiety disorders and with substance abuse disorders. The use of stimulants such as amphetamines, MDMA, mephedrone, methamphetamine or cocaine is linked to the onset and exacerbation of anxiety and panic attacks. Depressants, such as alcohol, benzodiazepines or barbiturates may be used short term to self-medicate for anxiety and panic attacks. However, withdrawal from depressants frequently leads to anxiety and panic attacks as symptoms.

Substance Use Disorders and Psychiatric Disorders

A symptom of a substance use disorder may also be a symptom of a psychiatric disorder. These symptoms include, but are not limited to, anxiety, irritability, difficulty concentrating, difficulty thinking clearly, mood swings, nightmares, depression, tension, panic attacks, short term memory loss, restlessness, a feeling of helplessness, stress-sensitivity, aberrant reward processing or a combination thereof.

Psychiatric disorders such as depression, bipolar disorder or schizophrenia, anxiety disorder, post-traumatic stress disorder, obsessive-compulsive disorder, anti-social personality disorder and autism spectrum disorder are frequently comorbid with substance use disorders. In some embodiments, the psychiatric disorder causes the substance use disorder. For example, an individual with depression may attempt to self-medicate through use of substances that elevate their mood, such as alcohol or cocaine. In some embodiments, the substance use disorder causes the psychiatric disorder. For example, alcohol use can increase feelings of sadness and/or fatigue associated with depression. In some embodiments, a psychiatric disorder both precedes the substance use disorder, and is altered or exacerbated by the substance use disorder. Substance use disorders and psychiatric disorders can be functionally related through the involvement of the same regions in the brain and the same neurotransmitter signaling systems, for example brain regions and systems that are involved in reward processing, responding to stress or anxiety, or regulating mood. In some embodiments, a substance use disorder produces psychiatric symptoms such as anhedonia and negative affect. Both substance use disorders and psychiatric disorders can be treated using the R(−)-ketamine compositions and methods of the disclosure.

Treatments

In the treatment of psychiatric disorders associated with substance use disorders, such as depression, bipolar disorder, schizophrenia, anxiety disorders, post-traumatic stress disorder and autism spectrum disorder, medication is essential, and an antidepressant (e.g., a tricyclic antidepressant, a selective serotonin reuptake inhibitor, and a serotonin and norepinephrine reuptake inhibitor), an antipsychotic (e.g., a phenothiazine-based compound, a butyrophenone-based compound, a benzamide-based compound, an iminodibenzyl compound, a thiepin-based compound, an indole-based compound, and a serotonin/dopamine receptor antagonist), and an anti-anxiety drug are administered. However, those drugs used actually in a clinical field are effective for some patients and some symptoms, but patients for whom the drugs are ineffective, so-called treatment-resistant patients are also known to exist. Thus, there is a strong demand for development of a novel therapeutic drug both for psychiatric disorders and substance use disorders. It is hard to say that the existing drugs exhibit sufficient therapeutic effects on those psychiatric disorders and or substance use disorders. In reality, there are substantially no effective prevention and treatment methods at present.

One of the major problems in treatment of depression in psychiatric or substance use disorders is that there are limitations on the effects of the antidepressant and effects of its adjuvant therapy. It takes several weeks or more for the current antidepressants to express their drug efficacy. In addition, there exist treatment-resistant patients for whom those antidepressants are ineffective. Therefore, it is also said that only 50% of patients with depression reach remission. In addition, when a dose of the antidepressant is increased for achieving remission, a patient suffers from various side effects accordingly. Further, depression is one of the cause of suicide. Depression in elderly peoples is known to increase the risk if incident dementia, in particular of Alzheimer's disease and vascular dementia (Non Patent Literature 1).

There are currently three main pharmacotherapeutic strategies used to treat substance use disorders: gradually reducing regimens, substitution therapies and medication assisted treatments. A list of therapeutics used in substitution therapies and medication assisted treatments is set forth below in Table 2. These strategies facilitate withdrawal from a substance, treat the symptoms associated with the substance use disorder, and help prevent relapse in subjects with substance use disorders who have stopped taking the substance.

TABLE 2

| Pharmacotherapies | | |
|---|---|---|
| Name | Brand Name ® | Substance use disorder |
| Methadone | (see Table 1) | opioids |
| Buprenorphine | Buprenex, Butrans, Probuphine, Belbuca | opioids |
| Clonidine | Catapres, Kapvay | opioids |
| Lofexidine | BritLofex | opioids |
| Naltrexone | Revia, Vivitrol | opioids, alcohol |
| Barbiturates | (see Table 1) | alcohol |
| Acamprosate | Campral | alcohol |
| Benzodiazepines | (see Table 1) | alcohol |
| Gabapentin | Neurontin, Gralise, Horizant, SmartRx Gaba-V Kit, Neuraptine | alcohol |
| Guanfacine | Intuniv ER | alcohol |
| Disulfiram | Antabuse | alcohol, cocaine |
| Topiramate | Topamax, Qudexy XR, Trokendi XR | alcohol, cocaine |
| amphetamines | (see Table 1) | cocaine |
| Selective Serotonin Reuptake Inhibitors (SSRIs) | | cocaine |
| Tetrahydrocannabinol, Dronabinol | Marinol, Syndros | Marijuana/cannabis |

TABLE 2-continued

Pharmacotherapies

| Name | Brand Name ® | Substance use disorder |
|---|---|---|
| N-acetylcysteine (NAC) | Acetadote, NAC, Cetylev | Marijuana/cannabis |
| Nabilone | Cesamet | Marijuana/cannabis |
| Bupropion | Zyban, Aplenzin, Wellbutrin XL, Wellbutrin SR, Forfivo XL | tobacco, nicotine |
| Nicotine | (see Table 1) | tobacco |
| Varenicline | Chantix | tobacco, nicotine |

The first pharmacotherapeutic strategy is a gradually reducing regimen. In this strategy, the subject is provided with gradually decreasing amounts of the substance to which they are addicted. Tapering, rather than abruptly ceasing, the substance helps reduce the severity of the withdrawal symptoms as substance use is discontinued.

Second, a subject with a substance use disorder can be treated using a substitution therapy. In this case, the subject is given an agent, e.g. an agonist, which has a similar effect on the neural circuitry of the subject as the substance to which the individual is addicted. In some cases, the amount of this agent is then gradually reduced in a way that helps manage or reduce the severity of the withdrawal symptoms as use of the agent is discontinued. Exemplary agents used for this sort of therapy include, but are not limited to benzodiazepines for alcohol withdrawal, which have a similar effect on GABA; nicotine replacement for tobacco; tetrahydrocannabinol (THC) analogs for cannabis; and methadone or buprenorphine for opioid addiction.

In some embodiments of the substitution therapy of the disclosure, withdrawal, either via a gradually reducing regimen or rapid withdrawal, is not achieved. Rather, the symptoms of the substance use disorder, such as craving, are treated by the substitution therapy.

Lastly, an additional strategy for treating substance use disorders is through a medication assisted treatment. With this strategy, the subject is given one or more medications to manage symptoms of the substance use disorder. This strategy can help manage symptoms of withdrawal. For example, withdrawal symptoms such as insomnia or disturbed sleep, digestive symptoms such as nausea and/or vomiting and mood problems such as depression, restlessness or tension can all be treated through use of a medication assisted treatment. Medications used to treat substance use disorder symptoms include, but are not limited to, zolpidem, benzodiazepines and stimulants. Withdrawal from some substances, for example opioids and cannabis, is associated with a noradrenergic surge, which causes symptoms such as hypertension, headache, sweating, irregular heart rate, anxiety, panic attacks and loss of color. Alpha-2 agonists, such as clonidine, lofexidine and guanfacine can all be used to treat these symptoms. Other medications can be used to modulate other neurotransmitters, such as glutamatergic signaling, to treat other symptoms of substance use disorders.

Medication assisted treatments can also be used to treat symptoms, for example psychological symptoms, that contribute to relapse. Medication assisted treatments can target neurotransmitter systems that may be involved in heightened reactivity to substance related cues, stress sensitivity, aberrant reward processing or substance craving. These neurotransmitter systems include the glutamatergic, monoaminergic and opioid systems. For example, Bupropion is a dopamine and norepinephrine reuptake inhibitor that can reduce craving and promote abstinence in nicotine dependence. Topiramate is a partial glutamate antagonist that reduces craving in cocaine and alcohol dependence. Gabapentin increases the concentration of GABA in the brain, and can be used to treat symptoms in alcohol and cannabis users. Memantine, a low-affinity NMDAR antagonist, can reduce cue reactivity. Naltrexone, an opioid receptor antagonist, reduces cravings in in a subject with alcohol and opioid dependence.

Medication assisted treatments, in addition to, or instead of, their effect on neurotransmission, can also act by changing the conditioned responses of a subject to substance, and affect reward processing. For example, naltrexone also blocks the effects of opioids, decoupling the association between craving and its fulfillment. Disulfiram inhibits alcohol metabolism, leading to a buildup of toxic aldehydes with alcohol consumption. Both disulfiram and naltrexone prevent the subject from receiving a pleasurable outcome from substance use, thus changing the reward salience of substance use.

Medication assisted treatments can normalize aberrant reward processing associated with substance use disorders by targeting neurotransmitters signaling systems such as dopamine or serotonin signaling. For example, dopamine signaling is a key component of the reward system, and the aberrant reward processing seen in substance use disorders often involves reduced dopamine signaling. One clinical approach to a medication assisted treatment involves strategies to improve dopamine signaling. Stimulants such as amphetamine and modafinil, Parkinson's medications, and medications that block dopamine metabolism such as nepicistat and disulfiram can be used to increase dopamine levels in the central nervous system of the subject. Alternatively, or in addition, antidepressants such as serotonin reuptake inhibitors (SSRIs) can be used to treat aberrant reward processing by targeting other neurotransmitters, such as serotonin, which are associated with the ability to experience pleasure, and with motivation. Other pharmacotherapeutic approaches modulate glutamate neurotransmission in the amygdala and striatum, which is hyperactivated in individuals with aberrant reward processing. For example, N-acetylcysteine (NAC), which upregulates the cysteine-glutamate exchanger, can be used to treat cannabis dependence.

However, existing pharmacotherapies can themselves be problematic. Some of the medications used to treat substance use disorders can themselves induce symptoms such as agitation. Other medications also cause withdrawal symptoms, or provide only temporary relief, with the symptoms associated with the substance used disorder reoccurring upon stopping the administration of the medication. Gradually reducing regimens, for example, the regimen of gradually reducing the dose of an opioid, require long periods of treatment. Furthermore, this method does not result in the subject fundamentally getting rid of their substance dependence, and the proportion of relapse after treatment is high. In one frequently used substitution therapy, methadone is substituted for another opioid, such as heroin or morphine. However, methadone is an analgesic and may also result in drug dependence. For example, the dependence potential of 100 mg of oral methadone is equivalent to that of 10 mg of injected morphine. In addition, methadone itself has many side effects, such as, pneumocystis, immunologic symptoms, impotency, as well as accumulation of the drug in the body leading to intoxication, and, more seriously, blindness in both eyes. Infants born by mothers addicted to methadone are likely to show withdrawal symptoms. There those exists a need in the art for additional pharmacotherapies to treat substance use disorders, such as the compositions and methods comprising R(−)-ketamine of the disclosure.

Pharmacotherapies of the disclosure may be combined with behavioral therapies. Exemplary, but non-limiting behavioral therapies comprise contingency management systems, counseling, mindfulness based therapies, cognitive behavioral therapy, digitally administered behavioral therapy or virtual reality based behavioral therapy. Counseling may be in person, or digitally administered (for example, web or telephone based counseling). Counseling may be one on one, e.g. with a therapist, with a group, or both. Contingency management is a type of behavioral therapy that uses operant conditioning. Contingency management provides rewards for desired behaviors (e.g., no substance use), and may take disciplinary measures in response to undesirable behaviors (e.g., substance use). Cognitive behavior therapy, originally developed to treat depression, has been expanded to treat symptoms of additional psychiatric and substance use disorders. In cognitive behavioral therapy, the subject works with one or more teachers or therapists to learn how to be aware of their thoughts and actions, and to identify and change mental distortions that contribute to psychiatric or substance use disorders. Mindfulness based therapy is a type of cognitive therapy that incorporates mindfulness practices such as meditation and breathing exercises. In some embodiments, mindfulness based therapy is a group therapy. In some embodiments, the behavioral therapy may be a virtual reality based therapy. Virtual reality based therapy have been used in treating symptoms such as paranoia and anxiety in subjects with psychiatric disorders. Virtual reality based therapies allow subjects to be exposed to, and respond to, stimuli in a controlled, virtual environment.

In some embodiments, administering a therapeutically effective amount of a composition comprising R(−) ketamine of the disclosure can increase adherence to a treatment regimen. For example, administration of R(−)-ketamine to rodents showed that R(−)-ketamine reduced the conditioned place preference response to morphine (FIG. 7). This shows that administering R(−)-ketamine compositions can reduce the preference or liking of a subject for a substance of a substance use disorder. This effect of the R(−)-ketamine compositions of the disclosure, in addition to the ability of R(−)-ketamine compositions to reduce withdrawal symptoms as described herein, can increase the adherence to treatment regimens for substance use disorders, or decrease the addiction potential of a substance. Accordingly, the R(−)-ketamine compositions and methods of the disclosure can increase adherence to a medically (medication) assisted treatment regimens for a substance use disorder, such as medically assisted treatment for opioid addiction. The R(−)-ketamine compositions and methods of the disclosure can also increase the ability of those subjects who have stopped taking a substance of a substance use disorder to remain abstinent.

Any of the pharmacotherapies or behavioral therapies, alone or in combination, is envisaged as being used with the R(−)-ketamine compositions and methods of the disclosure. In recent research, growing evidence suggests that abnormality in glutamatergic transmission, in particular, glutamatergic neurotransmission via an N-methyl-D-aspartate (hereinafter abbreviated as NMDA) receptor is associated with the pathophysiology of mood disorders such as major depressive disorder (hereinafter abbreviated as MDD) and bipolar disorder. The NMDA receptor also plays key roles in neurobiology and treatment of MDD as well (Non Patent Literature 2).

It has been reported that an NMDA receptor antagonist ketamine exhibits rapid and robust antidepressant effects on treatment-resistant patients with MDD and depressive symptoms of treatment-resistant bipolar disorder (Non Patent Literatures 3 to 5). In addition, it has been reported that ketamine is also effective for treatment-resistant obsessive-compulsive disorder and treatment-resistant posttraumatic stress disorder (hereinafter abbreviated as PTSD) (Non Patent Literatures 6 to 8). Ketamine has also been reported to have an effect of inhibiting suicide ideation (Non Patent Literature 9). Further, ketamine treatment in an adult with autism spectrum has been reported (Non Patent Literature 10). Ketamine, which was a compound developed as an anesthetic in 1962, started to be applied clinically in 1965. However, ketamine is designated as a controlled substance because of its problems of psychotic symptoms such as hallucination and delusion, and drug dependence. At present, ketamine is used as an anesthetic and for treatment of chronic pain in a clinical field.

It has been reported that clinical antidepressant effects of ketamine last for a short period of from 1 to 2 days starting from several hours after its single administration. Meanwhile, it has been reported that the effects may last over 2 weeks or more (Non Patent Literatures 3, 4, and 11). In addition, it has been reported that ketamine has psychotomimetic effects as side effects, and antidepressant effects of ketamine were not present until after the side effects had disappeared (Non Patent Literatures 3 and 4).

Ketamine (sometimes referred to as RS(+/−)-ketamine) is a racemic mixture containing equal amounts of R(−)-ketamine and S(+)-ketamine. R(−)-ketamine and S(+)-ketamine are also called R-isomer and S-isomer of ketamine, respectively. S(+)-ketamine has approximately 4-fold greater affinity for the NMDA receptor than R-isomer (Non Patent Literature 12). Further, S(+)-ketamine has an approximately 3- to 4-fold anesthetic effect as compared to R-isomer, and has greater psychotomimetic side effects than R-isomer (Non Patent Literature 12). As described above, the potency of psychotomimetic effects of ketamine is correlated with the potency of blockade of the NMDA receptor (Non Patent Literature 12). A positron emission tomography (PET) study in healthy volunteers demonstrated that psychotomimetic doses of S(+)-ketamine (i.e., intravenous infusion of 15 mg for 5 min, then infusion of the dose (0.014 to 0.02 mg/kg/min for 53 min) increased cerebral metabolic rates of glucose (hereinafter abbreviated as CMRglu) markedly in the frontal cortex and thalamus (Non Patent Literature 13). In contrast, equimolar doses of R(−)-ketamine tended to decrease CMRglu across brain regions, and did not produce psychotic symptoms, but a state of relaxation and a feeling of well being (Non Patent Literature 13).

As described above, it is generally understood that both analgesic effects and psychotomimetic effects of ketamine are mediated primarily via the blockade of the NMDA receptor. The S-isomer of ketamine has high affinity for the NMDA receptor. Thus, it is considered that those effects of ketamine are caused primarily by the S-isomer.

At present, ketamine is one of the drugs that have attracted attention for treatment of treatment-resistant patients with MDD, depressive symptoms of treatment-resistant bipolar disorder, treatment-resistant obsessive-compulsive disorder, treatment resistant PTSD (Non Patent Literatures 5 to 12), and symptoms of substance use disorders. A previous case report showed that antidepressant effects of S(+)-ketamine (0.25 mg/kg, i.v.) in treatment-resistant patients with MDD were weaker than those of RS(+/−)-ketamine (0.5 mg/kg, i.v.) (Non Patent Literature 14). Further, an open label study (Non Patent Literature 15) and a case report (Non Patent Literature 16) showed that effective oral doses of RS(+/−)-ketamine and S(+)-ketamine in patients with depression were 0.5 mg/kg and 1.25 mg/kg, respectively. In addition, intranasal administration of ketamine showed antidepressant effect in treatment-resistant patients with MDD (Patent Literature 1 and Non Patent Literature 17), and S(+)-ketamine was recently approved by the FDA for the same indications.

It has been reported that the NMDA receptor antagonist ketamine exhibits rapid antidepressant effects in treatment-resistant patients with depression. The glutamatergic neurotransmission via the NMDA receptor is considered to be involved in depression, ketamine includes optical isomers, i.e., S-isomer and R-isomer, and S-isomer has higher affinity for the NMDA receptor than R-isomer. Thus, the S-isomer or a racemic mixture has been used for research on treatment of depression with ketamine, and S(+)-ketamine has recently been approved for the treatment of depression by the FDA. However, ketamine has problems of side effects including psychotic symptoms such as hallucination and delusion, and dependence, and is designated as a controlled substance. Accordingly, it is difficult to practically use ketamine in a clinical field.

An object of the present disclosure is to provide a novel compound, R(−)-ketamine, having rapid and long-lasting effects on substance abuse disorders. Further, R(−)-ketamine, unlike the S(+)-ketamine isomer, importantly is less likely than S(+)-ketamine to produce negative symptoms associated with substance use disorders such as anhedonia or negative affect. R(−)-ketamine also has a lower potential for addiction than S(+)-ketamine. Negative affective symptoms such as anhedonia, negative affect or dissociative effects, and other adverse events limit the use of racemic and S(+)-ketamine, as when a subject is in substance withdrawal, further dissociative symptoms or anxiety can worsen withdrawal and decrease the likelihood of successful treatment. The substance abuse disorders may be comorbid with psychiatric disorders exhibiting depressive symptoms, such as depression, bipolar disorder, obsessive-compulsive disorder, PTSD and autism spectrum disorder, which can also be treated with the R(−)-ketamine of the disclosure.

R(−)-ketamine or a pharmaceutically acceptable salt thereof may be used in the treatment of a substance use disorder. The administration of R(−)-ketamine or a pharmaceutically acceptable salt thereof to a subject with a substance use disorder can reduce or eliminate a sign or a symptom of the disorder. For example, the administration of R(−)-ketamine or a pharmaceutically acceptable salt thereof to a subject with a substance use disorder can reduce or eliminate a broad array of anxiety and mood symptoms as described herein. Further, R(−)-ketamine, unlike S(+)-ketamine, does not exacerbate anhedonia or negative affect induced by substance use disorders when administered to the subject. R(−)-ketamine or a pharmaceutically acceptable salt thereof may be used for treatment and/or prevention of depressive symptoms such as a lack of interest in activities, changes in sleep pattern, changes in appetite, feelings of guilt, feelings of despair, lack of energy, trouble concentrating, stress, low mood or mood depression, impaired motivation, cognitive impairment, diminished ability to think, anxiety, insomnia, anhedonia and negative affect, anorexia, fatigue and suicidal thoughts that are associated with substance use disorders.

In some embodiments, administration of R(−)-ketamine or a pharmaceutically acceptable salt thereof to an individual with a substance use disorder can affect dopamine neurotransmission, for example in the nucleus accumbens. Administration of R(−)-ketamine can reduce symptoms such as substance craving, improve motivation (for example, to stop substance abuse behaviors), treat withdrawal symptoms and normalize aberrant reward processing. Administration of R(−)-ketamine can effect impulsivity and behavioral reactivity, including cue reactivity that leads to substance use. Administration of R(−)-ketamine can reduce compulsions, including compulsions to substance use, and reduce overvalued ideation. Administration of R(−)-ketamine can restore glutamate homeostasis in the prefrontal regions of the brain following substance use mediated changes, reverses synaptic pruning between the prefrontal and mesolimbic regions, and sustain attenuations in resting-state hyperconnectivity in the default mode network (DMN), which are linked to obsessive-compulsive disorder.

Further, administration of R(−)-ketamine to a subject with depression associated with a substance use disorder can treat depression in the subject. In the present disclosure, through the use of a new animal model of depression, it was demonstrated that R(−)-ketamine had rapid and long-lasting antidepressant effects. The animal model was prepared by the inventors of the present application based on their finding that depression-like behavior was found in mice exposed neonatally to DEX at a juvenile stage and an adult stage (Non Patent Literature 18; see Example 1). The animal model exhibits depression-like behavior even at a juvenile stage, and hence is useful as an animal model of depression in children as well as depression in adults.

In the present disclosure, it was also revealed that R(−)-ketamine had antidepressant effects in a social defeat stress model as well. The social defeat stress model is a typical animal model of depression, stress and anxiety, which is used throughout the world (Non Patent Literature 19).

R(−)-ketamine exhibited rapid and long-lasting antidepressant effects on depression-like behaviors of the juvenile mice after the neonatal DEX exposure and the social defeat stress mouse model through its single administration (see Example 1 and Example 2). Meanwhile, in locomotion-enhancing effects, disruption of prepulse inhibition, and a dependence test using a conditioned place preference test, which are evaluation systems for side effects, significant changes were found in S(+)-ketamine, whereas such side effects were not found in R(−)-ketamine (see Examples 4, 5, and 6). In addition, in the conditioned place preference test, RS(+/−)-ketamine increased a conditioned place preference (CPP) score, indicating drug dependence of RS(+/−)-ketamine. Further, R(−)-ketamine has low affinity for the NMDA receptor as compared to S(+)-ketamine, and thus is considered to have less side effects such as psychotomimetic effects. Accordingly, R(−)-ketamine can serve as a promising and safe antidepressant as compared to S(+)-ketamine and RS(+/−)-ketamine.

R(−)-ketamine or a pharmacologically acceptable salt thereof may be used as an antidepressant, specifically, as an agent to be used for treatment and/or prevention of depressive symptoms associated with substance use disorders, such as mood depression, lowering of motivation, anxiety, the accompanying insomnia and anorexia, and suicidal ideation.

The agents and pharmaceuticals composition according to the present disclosure are applicable to substance use disorders exhibiting depressive symptoms, for example, depression such as MDD or pediatric depression, and bipolar disorder involving a repeat of depressive symptoms and manic symptoms as their opposite symptoms, and are more preferably applicable to depression in children and depression in adults. In addition, it has been reported that ketamine is also effective for treatment-resistant obsessive-compulsive disorder and treatment-resistant PTSD (Non Patent Literatures 6, 7, and 8). Thus, the agents and pharmaceutical compositions according to the present disclosure are applicable to obsessive-compulsive disorder and PTSD associated with substance use disorders. Obsessive-compulsive disorder, which is one type of anxiety disorder and is a disease with pathological conditions characterized by obsessions and compulsions, is considered to be associated with depression. Patients with obsessive-compulsive disorder have depression as well and exhibit depressive symptoms in addition to obsessions and compulsions in extremely many cases. Patients with PTSD exhibit depressive symptoms in many cases. In actuality, an antidepressant such as an SSRI is used as a therapeutic drug for PTSD, but its therapeutic effects are weak. The scope of the present disclosure encompasses pharmaceutical compositions for prevention and/or treatment of obsessive-compulsive disorder and PTSD, containing R(−)-ketamine or a pharmaceutically acceptable salt thereof in an effective amount for reducing symptoms of obsessive-compulsive disorder and PTSD, and being substantially free of S(+)-ketamine or a pharmaceutically acceptable salt thereof. In addition, ketamine treatment in an adult with autism spectrum has been reported (Non Patent Literature 10). Thus, the agents and pharmaceuticals compositions according to the present disclosure are preferably applicable to autism spectrum disorder. Furthermore, Depression in elderly peoples is known to increase the risk if incident dementia, in particular of Alzheimer's disease and vascular dementia (Non Patent Literature 1). Therefore, the agents and pharmaceuticals composition according to the present disclosure are a potential preventive or therapeutic drug for dementia including Alzheimers disease and vascular dementia.

Administration

The agents and pharmaceutical compositions according to the present disclosure may be administered orally or parenterally. In the oral administration, a known dosage form for administration, including a tablet, a capsule, a coated tablet, a troche, or a liquid such as a solution or a suspension, may be used. In addition, examples of the parenteral administration may include: intravenous, intramuscular, or subcutaneous administration by injection; transmucosal administration such as transnasal or oral administration using a spray, an aerosol, or the like; rectal administration using a suppository or the like; and transdermal or sublingual administration using a patch, a liniment, a gel, or the like. Preferred examples thereof may include oral administration, transnasal administration, sublingual and intravenous administration.

R(−)-Ketamine

The inventors have focused their attention on R(−)-ketamine, which has not been used for research on the treatment of substance use disorders using ketamine heretofore. The inventors have found, that in a mouse model of morphine addiction, R(−)-ketamine was able to significantly attenuate the addictive properties of morphine when co-administered to the mice. Furthermore, the inventors have found that R(−)-ketamine administered to rats was able to significantly ameliorate the symptoms of precipitated withdrawal from morphine. Furthermore, R(−)-ketamine was able to mitigate the effects of alcohol tolerance in rats. Surprisingly, R(−)-ketamine and its metabolite R-hydroxynorketamine, unlike S(+)-ketamine, also showed no anhedonic or negative affective side effects in rats. The present disclosure has been accomplished based on those findings, which indicate that R(−)-ketamine offers a superior treatment for substance use disorders such as opioid and alcohol use disorders when compared to S(+)-ketamine and racemic ketamine.

In addition, in research using a mouse model of depression, the inventors have found that R(−)-ketamine exhibits more potent antidepressant effects on the depression-like symptoms of the mouse model at a juvenile stage than S(+)-ketamine, and the effects last for a longer period. The inventors also found in social defeat stress model mice that R(−)-ketamine showed more potent and long lasting antidepressant effect compared to S(+)-ketamine. Furthermore, administration of S(+)-ketamine induced some side effects such as a hyperlocomotion, prepulse inhibition deficit, and drug dependence, while administration of R(−)-ketamine did not. Since R-isomer of ketamine has low affinity for an NMDA receptor as compared to its S-isomer, the R-isomer is considered to have less psychotomimetic effects as side effects and to hardly produce drug dependence. The present disclosure has been accomplished based on those findings.

R(−)-ketamine or a pharmaceutically acceptable salt thereof has rapid and long-lasting antidepressant effects and less side effects, and hence is effective for prevention and/or treatment of substance use disorders. In some embodiments, these substance use disorders are associated with psychiatric disorders and/or with depressive symptoms. Accordingly, the agent consisting of R(−)-ketamine or a pharmaceutically acceptable salt thereof, and the pharmaceutical composition including R(−)-ketamine or a pharmaceutically acceptable salt thereof, and being substantially free of S(+)-ketamine or a pharmaceutically acceptable salt thereof are useful as novel pharmaceuticals in the field of prevention and/or treatment of substance use disorders.

The phrase "substantially free of S(+)-ketamine or a pharmaceutically acceptable salt thereof" means that: S(+)-ketamine or a pharmaceutically acceptable salt thereof is not contained at all; or S(+)-ketamine or a pharmaceutically acceptable salt thereof may be contained in such an amount that its effects and side effects are not exhibited, or may be contained as such an impurity as to be mixed inevitably during the manufacture of the agent and the pharmaceutical composition. In some embodiments, R(−)-ketamine or a pharmaceutically acceptable salt thereof is substantially free of S(+)-ketamine when the R(−)-ketamine or a pharmaceutically acceptable salt thereof contains less than about 5% S(+)-ketamine or a pharmaceutically acceptable salt thereof, less than about 4% S(+)-ketamine or a pharmaceutically acceptable salt thereof, less than about 3% S(+)-ketamine or a pharmaceutically acceptable salt thereof, less than about 2% S(+)-ketamine or a pharmaceutically acceptable salt thereof, less than about 1% S(+)-ketamine or a pharmaceutically acceptable salt thereof, less than about 0.9% S(+)-ketamine or a pharmaceutically acceptable salt thereof, less than about 0.8% S(+)-ketamine or a pharmaceutically acceptable salt thereof, less than about 0.7% S(+)-ketamine or a pharmaceutically acceptable salt thereof, less than about 0.6% S(+)-ketamine or a pharmaceutically acceptable salt thereof, less than about 0.5% S(+)-ketamine or a pharmaceutically acceptable salt thereof, less than about 0.4% S(+)-ketamine or a pharmaceutically acceptable salt thereof, less than about 0.3% S(+)-ketamine or a pharmaceutically acceptable salt thereof, less than about 0.2% S(+)-ketamine or a pharmaceutically acceptable salt thereof, less than about 0.1% S(+)-ketamine or a pharmaceutically acceptable salt thereof, less than about 0.005% S(+)-ketamine or a pharmaceutically acceptable salt thereof or less than about 0.001% S(+)-ketamine or a pharmaceutically acceptable salt thereof.

R(−)-ketamine may be used in both the forms of a free base and a pharmaceutically acceptable salt thereof. The pharmaceutically acceptable salt is preferably a pharmaceutically acceptable acid addition salt, more preferably a hydrochloride. The chemical structural formula of R(−)-ketamine hydrochloride is represented by the following formula (I).

[Chem.I]

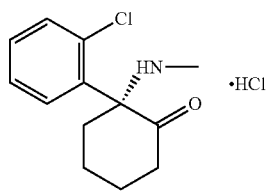

(I)

R(−)-ketamine or a pharmaceutically acceptable salt thereof may be subjected to modification, for example, substitution of a chlorine molecule as a substituent by another halogen molecule and/or substitution of a methyl group as a substituent by another alkyl group, to thereby manufacture a derivative. Exemplary halogens include fluorine, chlorine, bromine, iodine, astatine and tennessine. As a result, a compound having more preferred effects may be obtained. Further, when the compound according to the present invention is labeled with an isotope such as a stable isotope $^3C$ or $^2H$ (D), the compound can be measured for its in vivo kinetics and quantitatively measured for its affinity for the NMDA receptor in the brain, for example.

The pharmaceutical composition according to the present invention may contain, in addition to R(−)-ketamine or a pharmaceutically acceptable salt thereof, other ingredients having drug efficacy that are effective for substance abuse symptoms, the ingredients being other than S(+)-ketamine. In addition, the pharmaceutical composition according to the present invention may appropriately contain, in addition to those ingredients having drug efficacy, an appropriate pharmaceutically acceptable carrier well known to those of ordinary skill in the art, depending on an administration form and the like. Examples of the pharmaceutically acceptable carrier may include an antioxidant, a stabilizer, a preservative, a taste-masking agent, a colorant, a solubilizer, a solubilizing agent, a surfactant, an emulsifier, an antifoaming agent, a viscosity adjustor, a gelling agent, an absorption accelerator, a dispersant, an excipient, and a pH adjustor.

When the agent and pharmaceutical composition according to the present invention are each prepared as a formulation for injection, it is preferred that the formulation be in the form of a solution or a suspension. When the agent and pharmaceutical composition are each prepared as a formulation for transmucosal administration such as transnasal or oral administration, it is preferred that the formulation be in the form of a powder, a drop, or an aerosol. In addition, when the agent and pharmaceutical composition are each prepared as a formulation for rectal administration, it is preferred that the formulation be in the form of a semi-solid formulation such as a cream or a suppository. When the agent and pharmaceutical composition are each prepared as a formulation for sublingual administration, the formulation may be in the form of a fast dissolving strip or tablet. Each of those formulations may be prepared by any one of the methods known to those skilled in the art of pharmacy as disclosed in, for example, Remington's Pharmaceutical Sciences (Mack Publishing Company, Easton, Pa., 1970). In the formulation for injection, for example, a plasma-derived protein such as albumin, an amino acid such as glycine, and a sugar such as mannitol may each be added as a carrier, and a buffer, a solubilizing aid, an isotonic agent, and the like may also be added. In addition, when the formulation is used as a water-soluble formulation or a lyophilized formulation, it is preferred to add a surfactant such as Tween™ 80 or Tween™ 20 in order to prevent aggregation. Further, a dosage form for parenteral administration other than the formulation for injection may contain distilled water or saline, polyalkylene glycol such as polyethylene glycol, a plant-derived oil, hydrogenated naphthalene, and the like. For example, a formulation for rectal administration such as a suppository contains general excipients such as polyalkylene glycol, petrolatum, and cacao oil and fat. A vaginal formulation may contain an absorption accelerator such as a bile salt, an ethylenediamine salt, and a citric acid salt. A formulation for inhalation may be solid, and may contain an excipient such as lactose. Further, a transnasal drop may be a water or oil solution.

Dosages

The accurate dosage and dosing regimen of each of the agent and pharmaceutical composition according to the present invention may be adjusted depending on required amounts, treatment methods, diseases, degrees of necessity, or the like for individual treatment targets. The dosage may be specifically determined depending on an age, a body weight, a general health condition, a sex, a meal, an administration time, an administration method, an elimination rate, a combination of drugs, a medical condition of a patient, and the like, and may be determined in consideration of other factors. When the pharmaceutical composition according to the present invention is administered to individuals with substance use disorders exhibiting symptoms such as anxiety, irritability, difficulty concentrating, difficulty thinking clearly, mood swings, nightmares, depression, tension, panic attacks, short term memory loss, restlessness, a feeling of helplessness, stress-sensitivity, a heightened responsivity to substance-related cues, aberrant reward processing or substance craving, it is preferred that an active ingredient contained in the pharmaceutical composition be contained in an effective amount for reducing symptoms of the substance use disorder. R(−)-ketamine or a pharmaceutically acceptable salt thereof can be safely used because of having less side effects found in S(+)-ketamine and RS(+/−)-ketamine. Its dosage per day varies depending on the condition and body weight of a patient, the kind of a compound, an administration route, and the like. In some embodiments, in terms of the amount of an active ingredient, the dosage in the case of parenteral administration is from about 0.01 to 1000 mg/person/day, preferably from 0.1 to 500 mg/person/day, and the dosage in the case of oral administration be from about 0.01 to 500 mg/person/day, preferably from 0.1 to 100 mg/person/day. In some embodiments, in terms of the amount of an active ingredient, the dosage in the case of parenteral administration is from about 0.01 to 1,000 mg/person/2 days, preferably from 0.1 to 500 mg/person/2 days, and the dosage in the case of oral administration be from about 0.01 to 500 mg/person/2 days, preferably from 0.1 to 100 mg/person/2 days. In some embodiments, in terms of the amount of an active ingredient, the dosage in the case of parenteral administration is from about 0.01 to 1,000 mg/person/3 days, preferably from 0.1 to 500 mg/person/3 days, and the dosage in the case of oral administration be from about 0.01 to 500 mg/person/3 days, preferably from 0.1 to 100 mg/person/3 days. In some embodiments, in terms of the amount of an active ingredient, the dosage in the case of parenteral administration is from about 0.01 to 1,000 mg/person/week, preferably from 0.1 to 500 mg/person/week, and the dosage in the case of oral administration be from about 0.01 to 500 mg/person/week, preferably from 0.1 to 100 mg/person/week. In some embodiments, the composition is administered every 24 hours, 2 days, every 3 days, every 4 days, every 7 days, every 10 days, every 14 days or every 30 days. In some embodiments, in terms of the amount of an active ingredient, the dosage in the case of parenteral administration is from about 0.01 to 100 mg/kg/person/day. In some embodiments, the dosage in the case of parenteral administration is from about 0.1 to 50 mg/kg/person/day. In some embodiments, the dosage in the case of oral administration be from about 0.01 to 100 mg/kg/person/day. In some embodiments, the dosage in the case of oral administration be from about 0.01 to 50 mg/kg/person/day.

In some embodiments, the methods comprise administering a "therapeutically effective amount" of a composition comprising R(−)-ketamine or a pharmaceutically acceptable salt thereof, wherein the composition is substantially free of S(+)-ketamine or a pharmaceutically acceptable salt thereof. As used herein, a therapeutically effective amount refers to an amount of the R(−)-ketamine compositions described herein which is sufficient to treat or prevent at least one symptom or aspect of the substance use disorders as described herein. For example, a therapeutically effective amount of the R(−)-ketamine compositions described herein can prevent or reduce a relapse to substance use in an subject with a substance use disorder, reduce tolerance, reduce dependence or reduces preference or liking for a substance, improve adherence to a treatment, or increase abstinence from a substance. As a further example, a therapeutically effective amount of the R(−)-ketamine compositions described herein can treat symptoms such as symptoms of withdrawal or psychiatric symptoms associated with the substance use disorder.

In some embodiments, including those embodiments wherein the composition is administered to treat a withdrawal symptom in a subject, the prior to the onset of the at least one withdrawal symptom in the subject. In some embodiments, the composition is administered at the same time as the onset of the at least one withdrawal symptom in the subject. In some embodiments, the composition is administered after the onset of the at least one withdrawal symptom in the subject.

In some embodiments, including those embodiments wherein the composition is administered with an additional pharmacotherapy, behavioral therapy, or combination thereof, the composition is administered prior to the additional therapy. In some embodiments, the composition is administered at the same time as the additional therapy. In some embodiments, the composition is administered after the additional therapy.

CITATION LIST

Patent Literature

[PTL 1] International Patent Publication No. WO 2007/111880 A2
[PTL 2] U.S. Pat. No. 6,040,479 (A)

Non Patent Literature

[NPL 1] Diniz B D, Butters M A, Albert S M, Dew M A and Reynolds C F (2013) Latelife depression and risk of vascular dementia and Alzheimer's disease: systematic review and meta-analysis of community-based cohm1 studies. B. J. Psychiatry 202: 329-335.
[NPL 2] Hashimoto K (2009) Emerging role of glutamate in the pathophysiology Of major depressive disorder. Brain Res. Rev. 61:105-23.
[NPL 3] Berman R M, Cappiello A, Anand A, Oren D A, Heninger G R, Charney D S, Krystal J H (2000) Antidepressant effects of ketamine in depressed patients. Biol. Psychiatry 47:351-4.
[NPL 4] Zarate C A, Jr, Singh J B, Carlson P J, Brutsche N E, Ameli R, Luckenbaugh D A, Charney D S, Manji H K (2006) A randomized trial of an N-methyl-D-aspartate antagonist in treatment-resistant major depression. Arch. Gen. Psychiatry 63:856-64.
[NPL 5] Diazgranados N. Ibrahim L, Brutsche N E, Newberg A, Kronstein P, Khalife S, Kammerer W A, Quezado Z, Luckenbaugh D A, Salvadore G, Machado-Vieira R, Manji H K, Zarate C A Jr. (2010) A randomized add-on trial of an Nmethyl-D-aspartate antagonist in treatment-resistant bipolar depression. Arch. Gen. Psychiatry 67:793-802.
[NPL 6]Bloch M H, Wasylink S, Landeros-Weisenberger A, Panza K E, Billingslea E, Leckman J F, Krystal J H, Bhagwagar Z, Sanacora G, Pittenger C (2012) Effects of ketamine in treatment-refractory obsessive-compulsive disorder. Biol. Psychiatry 72(11):964-970.
[NPL 7] Rodriguez C I, Kegeles L S, LevinsonA, Feng T, Marcus S M, Vermes D, Flood P, Simpson H B (2013) Randomized Controlled Crossover Trial of Ketamine in Obsessive-Compulsive Disorder: Proof-of-Concept. Neuropsychopharmacology 38:2475-83.
[NPL 8] Feder A, Parides M K, Murrough J W, Perez A M, Morgan J E, Saxena S, Kirkwood K, Aan Het Rot M, Lapidus K A, Wan L B, losifescu D, Charney D S (2014) Efficacy of intravenous ketamine for treatment of chronic posttraumatic stress disorder: a randomized clinical trial. JAMA Psychiatry 71:681-688. [NPL 9] DiazGranados N, Ibrahim L A, Brutsche N E, Ameli R, Henter I D, Luckenbaugh D A, Machado-Vieira R, Zarate C A Jr (2010) Rapid resolution of suicidal ideation after a single infusion of an N-methyl-D-aspartate antagonist in patients with treatment-resistant major depressive disorder. J Clin. Psychiatry 71(12):1605-11.
[NPL 10] Wink L Kl, O'Melia A M, Shaffer R C, Pedapati E, Friedmann K, Schaefer T, Erickson C A (2014) Intranasal ketamine treatment in an adult with autism spectrum disorder. J Clin. Psychiatry 75(8):835-6. doi: 10.4088/JCP.13cr08917.

[NPL 11] Krystal J H, Sanacora G, Duman R S (2013) Rapid-acting glutamatergic antidepressants: the path to ketamine and beyond. Biol. Psychiatry 73:1133-41.

[NPL 12] Domino E F (2010) Taming the ketamine tiger. 1965. Anesthesiology 113:678-86.

[NPL 13] Vollenweider F X, Leenders K L, OEye I, Hell D, Angst J (1997) Differential psychopathology and patterns of cerebral glucose utilization produced by (S)- and (R)-ketamine in healthy volunteers using positron emission tomography (PET). Eur. Neuropsychopharmacol. 7: 25-38.

[NPL 14] Paul R, SchaaffN, Padberg F, Moeller H J, Frodl T (2009) Comparison of racemic ketamine and S-ketamine in treatment-resistant major depression: report from two cases. World J. Biol. Psychiatry 10: 241-244.

[NPL 15] Paslakis G, Gilles M, Meyer-Lindenberg A, Deuschle M (2010) Oral administration of the NMDA receptor antagonist S-ketamine as add-on therapy of depression: a case series. Pharmacopsychiatry 43: 33-35.

[NPL 16] Irwin S A, Iglewicz A, Nelesen R A, Lo J Y, CaIT CH, Romero S D, Lloyd L S (2013) Daily oral ketamine for the treatment of depression and anxiety in patients receiving hospice care: A 28-day open-label proof-of-concept trial. J. Palliat. Med. 16: 958-965.

[NPL 17] Lapidus K A, Levitch C F, Perez A M, Brallier J W, Parides M K, Soleimani L, Feder A, Iosifescu D V, Charney D S, Murrough J W (2014) A randomized controlled trial of intranasal ketamine in major depressive disorder. Biol. Psychiatry 2014 Apr. 3. pii: S0006-3223 (14)00227-3.doi: 10.1016/j.biopsych.2014.03.026. [Epub ahead of print]

[NPL 18] Li S X, Fujita Y, Zhang J C, Ren Q. Ishima T, Wu J, Hashimoto K (2014) Role of the NMDA receptor in cognitive deficits, anxiety and depressive-like behavior in juvenile and adult mice after neonatal dexamethasone exposure. Neurobiol. Dis. 62: 124-134.

[NPL 19] Golden S A, Covington H E, III, Berton O, Russo S J (2011) A standardized protocol for repeated social defeat stress in mice. Nat. Protoc. 6: 1183-1191.

Carlezon W A, Wise R A (1996) Microinjections of phencyclidine (PCP) and related drugs into nucleus accumbens shell potentiate medial forebrain bundle brain stimulation reward. *Psychopharmacology (Berl)* 128:413-420.

Carlezon W A, Jr. and Chartoff E H (2007) Intracranial self-stimulation (ICSS) in rodents to study the neurobiology of motivation. Nat Protoc 2:2987-2995.

Deneau G A, Seevers M H. Pharmacological aspects of drug dependence. Adv Pharmacol. 1964; 3:267-83.

Erami, E., Azhdari-Zarmehri, H., Rahmani, A., Ghasemi-Dashkhasan, E., Semnanian, S., & Haghparast, A. (2012). Blockade of orexin receptor 1 attenuates the development of morphine tolerance and physical dependence in rats. Pharmacology Biochemistry and Behavior, 103(2), 212-219.

Cooper M D, Rosenblat J D, Cha D S, Lee Y, Kakar R, McIntyre R S. Strategies to mitigate dissociative and psychotomimetic effects of ketamine in the treatment of major depressive episodes: a narrative review. World J Biol Psychiatry. 2017 September; 18(6):410-423.

Fidecka S. Interactions of ketamine, naloxone and morphine in the rat. Pol J Pharmacol Pharm. 1987 January-February; 39(1):33-40.

Fukumoto K, Toki H, Iijima M, Hashihayata T, Yamaguchi J I, Hashimoto K, Chaki S. Antidepressant Potential of (R)-Ketamine in Rodent Models: Comparison with (S)-Ketamine. J Pharmacol Exp Ther. 2017 April; 361(1):9-16.

Gastambide F, Mitchell S N, Robbins T W, Tricklebank M D, Gilmour G. (2013) Temporally distinct cognitive effects following acute administration of ketamine and phencyclidine in the rat. EurNeuropsychopharmacol. 23(11): 1414-1422.

Ginski M J, Witkin J M. Sensitive and rapid behavioral differentiation of N-methyl-D-aspartate receptor antagonists. Psychopharmacology (Berl). 1994 May; 114(4): 573-82.

Hashimoto K, Kakiuchi T, Ohba H, Nishiyama S, Tsukada H. Reduction of dopamine D23 receptor binding in the striatum after a single administration of esketamine, but not R-ketamine: a PET study in conscious monkeys. Eur Arch Psychiatry Clin Neurosci. 2017 March; 267(2):173-176.

Herman B H, Vocci F, Bridge P. The effects of NMDA receptor antagonists and nitric oxide synthase inhibitors on opioid tolerance and withdrawal. Medication development issues for opiate addiction. Neuropsychopharmacology. 1995 December; 13(4):269-93.

Hillhouse T M, Porter J H. (2013) Ketamine, but not MK-801, produces antidepressant-like effects in rats responding on a differential-reinforcement-of-low-rate operant schedule. Behav Pharmacol. 25(1): 80-91.

Hillhouse T M, Porter J H, Negus S S. Dissociable effects of the noncompetitive NMDA receptor antagonists ketamine and MK-801 on intracranial self-stimulation in rats. Psychopharmacology (Berl). 2014 July; 231(13):2705-16.

Higgins G A, Nguyen P, Sellers E M. The NMDA antagonist dizocilpine (MK801) attenuates motivational as well as somatic aspects of naloxone precipitated opioid withdrawal. Life Sci. 1992; 50(21):PL167-72.

Higgins G A, Sellers E M. Antagonist-precipitated opioid withdrawal in rats: evidence for dissociations between physical and motivational signs. Pharmacol Biochem Behav. 1994 May; 48(1):1-8

Huhn A S, Meyer R E, Harris J D, Ayaz H, Deneke E, Stankoski D M, Bunce S C. Evidence of anhedonia and differential reward processing in prefrontal cortex among post-withdrawal patients with prescription opiate dependence Brain Res Bull. 2016 May; 123:102-9.

Ji D, Sui Z Y, Ma Y Y, Luo F, Cui C L, Han J S. NMDA receptor in nucleus accumbens is implicated in morphine withdrawal in rats. Neurochem Res. 2004 November; 29(11):2113-20.

Jovaisa T, Laurinenas G, Vosylius S, Sipylaite J, Badaras R, Ivaskevicius J. Effects of ketamine on precipitated opiate withdrawal. Medicina (Kaunas). 2006; 42(8):625-34.

Ke X, Ding Y, Xu K, He H, Wang D, Deng X, Zhang X, Zhou Y, Zhou C, Liu Y, Ning Y, Fan N. The profile of cognitive impairments in chronic ketamine users. Psychiatry Res. 2018 August; 266:124-131.

Khanna J M, Shah G, Weiner J, Wu P H, Kalant H. Effect of NMDA receptor antagonists on rapid tolerance to ethanol. Eur J Pharmacol. 1993 Jan. 5; 230(1):23-31.

Kolesnikov Y, Jain S, Wilson R, Pasternak G W. Blockade of morphine-induced hindlimb myoclonic seizures in mice by ketamine. Pharmacol Biochem Behav. 1997 March; 56(3):423-5.

Koob G F. Neural mechanisms of drug reinforcement. Ann N Y Acad Sci. 1992 Jun. 28; 654:171-91.

Koyuncuoglu H, Gungor M, Sagduyu H, Aricioglu F. Suppression by ketamine and dextromethorphan of precipitated abstinence syndrome in rats. Pharmacol Biochem Behav. 1990 April; 35(4):829-32

Langdon K J, Dove K, Ramsey S. Comorbidity of opioid-related and anxiety-related symptoms and disorders. Cur Opin Psychol. 2019 Jan. 4; 30:17-23.

Li F, Fang Q, Liu Y, Zhao M, Li D, Wang J, Lu L. Cannabinoid CB(1) receptor antagonist rimonabant attenuates reinstatement of ketamine conditioned place preference in rats. Eur J Pharmacol. 2008 Jul. 28; 589(1-3):122-6

Liu Y, Lin D, Wu B, Zhou W. Ketamine abuse potential and use disorder. Brain Res Bull. 2016 September; 126(Pt 1):68-7.

Miller N S, Dackis C A, Gold M S. The relationship of addiction, tolerance, and dependence to alcohol and drugs: a neurochemical approach. J Subst Abuse Treat. 1987; 4(3-4):197-207.

Napier T C, Herrold A A, de Wit H. Using conditioned place preference to identify relapse prevention medications. Neurosci Biobehav Rev. 2013 November; 37(9 Pt A):2081-6.

Negus S S, Miller L L. Intracranial self-stimulation to evaluate abuse potential of drugs. Pharmacol Rev. 2014 July; 66(3):869-91.

Nikiforuk A, Popik P. (2014) The effects of acute and repeated administration of ketamine on attentional performance in the five-choice serial reaction time task in rats. Eur Neuropsychopharmacol. 24(8): 1381-1393.

Paxinos G, Watson C (2007) The rat brain in stereotaxic coordinates (Academic Press, Burlington).

Persson J, Hasselstrom J, Wiklund B, Heller A, Svensson J O, Gustafsson L L. The analgesic effect of racemic ketamine in patients with chronic ischemic pain due to lower extremity arteriosclerosis obliterans. Acta Anaesthesiol Scand. 1998 August; 42(7):750-8.

Persson J, Hasselstrom J, Maurset A, Oye I, Svensson J O, Almqvist O, Scheinin H, Gustafsson L L, Almqvist O. Pharmacokinetics and non-analgesic effects of S- and R-ketamines in healthy volunteers with normal and reduced metabolic capacity. Eur J Clin Pharmacol. 2002 February; 57(12):869-75.

Rowland L M. Subanesthetic ketamine: how it alters physiology and behavior in humans. Aviat Space Environ Med. 2005 July; 76(7 Suppl):C52-8.

Shearman, G. T., Lal, H., & Ursillo, R. C. (1980). Effectiveness of lofexidine in blocking morphine-withdrawal signs in the rat. Pharmacology Biochemistry and Behavior, 12(4), 573-575.

Streel E, Dan B, Antoniali V, Clement B, Campanella S, Hanak C, Vanderlinden P, Pelc I, Verbanck P. Effects of anaesthetic agents in interference of naloxone-induced opiate-withdrawal are dose-dependent in opiate-dependent rats. Life Sci. 2005 June 24; 77(6):650-5.

Suzuki T, Kato H, Aoki T, Tsuda M, Narita M, Misawa M. Effects of the non-competitive NMDA receptor antagonist ketamine on morphine-induced place preference in mice. Life Sci. 2000 Jun. 16; 67(4):383-9.

Trujillo K A. Effects of noncompetitive N-methyl-D-aspartate receptor antagonists on opiate tolerance and physical dependence. Neuropsychopharmacology. 1995 December; 13(4):301-7.

Tzschentke T M. Measuring reward with the conditioned place preference (CPP) paradigm: update of the last decade. Addict Biol. 2007 September; 12(3-4):227-462.

Wang C, Zheng D, Xu J, Lam W, Yew D T. Brain damages in ketamine addicts as revealed by magnetic resonance imaging. Front Neuroanat. 2013 Jul. 17; 7:23.

White P F, SchOttler J, Shafer A, Stanski D R, Horai Y, Trevor A J. Comparative pharmacology of the ketamine isomers. Studies in volunteers. Br J Anaesth. 1985 February; 57(2):197-203.

Yang C, Shirayama Y, Zhang J C, Ren Q, Yao W, Ma M, Dong C, Hashimoto K. R-ketamine: a rapid-onset and sustained antidepressant without psychotomimetic side effects. Transl Psychiatry. 2015 Sep. 1; 5:e632.

Zhang J C, Li S X, Hashimoto K. R (−)-ketamine shows greater potency and longer lasting antidepressant effects than S (+)-ketamine. Pharmacol Biochem Behav. 2014 January; 116:137-41.

Koob G F. Neurobiological substrates for the dark side of compulsivity in addiction. Neuropharmacology. 2009; 56 Suppl 1:18-31

Koob G F, Volkow N D. Neurobiology of addiction: a neurocircuitry analysis. Lancet Psychiatry. 2016 August; 3(8):760-73.

Hatzigiakoumis D S, Martinotti G, Giannantonio M, Janiri L. Anhedonia and substance dependnece: Cilinical correleates and treatment options. Frontiers in Psychiatry. 2011; 2:1-11.

Krupitsky E, Zvartau E, Blokhina E, Verbitskaya E, Wahlgren V, Tsoy-Podosenin M, Bushara N, Burakov A, Masalov D, Romanova T, Tyurina A, Palatkin V, Yaroslavtseva T, Pecoraro A, Woody G. Anhedonia, depression, anxiety, and craving in opiate dependent patients stabilized on oral naltrexone or an extended release naltrexone implant. Am J Drug Alcohol Abuse. 2016 September; 42(5):614-620.

Krystal J H, Karper L P, Seibyl J P, Freeman G K, Delaney R, Bremner J D, Heninger G R, Bowers M B Jr, Charney D S. Subanesthetic effects of the noncompetitive NMDA antagonist, ketamine, in humans. Psychotomimetic, perceptual, cognitive, and neuroendocrine responses. Arch Gen Psychiatry. 1994 March; 51(3):199-214.

Bell D S. The motivation of addiction. Acta Neurochir (Wien). 1995; 132(4):185-91.

Perry M B. Perceptions of Mindfulness: A Qualitative Analysis of Group Work in Addiction Recovery. R I Med J (2013). 2019 Mar. 1; 102(2):28-31.

Vayr F, Herin F, Jullian B, Soulat J M, Franchitto N. Barriers to seeking help for physicians with substance use disorder: A review. Drug Alcohol Depend. 2019 Apr. 18; 199:116-121.

Vollenweider F X, Leenders K L, Oye I, Hell D, Angst J. Differential psychopathology and patterns of cerebral glucose utilisation produced by (S)- and (R)-ketamine in healthy volunteers using positron emission tomography (PET). Eur Neuropsychopharmacol. 1997 February; 7(1): 25-38.

EXAMPLES

The present invention is hereinafter described in more detail by way of Examples. However, the present invention is by no means limited to Examples below. Further, various modifications are possible without departing from the technical concept of the present invention.

Example 1: Neonatal Dexamethasone Exposure Model

A new animal model of depression (Non Patent Literature 18) was used to investigate antidepressant effects of R(−)- and S(+)-ketamine on the depression-like behavior of the animal model. All tests were performed under the approval of the Animal Care and Use Committee of Chiba University.

1. Materials and Methods

R(−)- and S(+)-ketamine hydrochloride were prepared from RS(+/−)-ketamine (Ketalar™, ketamine hydrochloride, Daiichi Sankyo Co., Ltd., Tokyo, Japan) using D(−)- and L(+)-tartaric acid, respectively, by the method disclosed in the previous report (Patent Literature 2) (FIG. 1). The purity of each of those isomers was confirmed by high performance liquid chromatography (CHIRALPAK™ IA, column size: 250×4.6 mm, mobile phase; n hexane/dichloromethane/diethylamine (75/25/0.1), retention time for S(+)-ketamine=6.99 min, retention time for R(−)-ketamine=10.56 min, Daicel Corporation, Tokyo, Japan).

A new animal model of depression was prepared by exposing mice neonatally to dexamethasone (hereinafter abbreviated as DEX). Through the neonatal DEX exposure, depression-like behavior was observed in each of juvenile mice and adult mice. Thus, the mouse model was shown to be able to serve as a novel animal model of depression. The mouse model was prepared and reported only recently by the inventors of the present application and their collaborators (Non Patent Literature 18). Specifically, the juvenile mice exposed neonatally to DEX and the adult mice exposed neonatally to DEX showed a significant decrease in novel object search time in a novel object recognition test as compared to control mice, which indicated a reduction in social learning property in the model mice. In addition, in a social memory test, the mice exposed neonatally to DEX showed a significant decrease in stimulation target follow-up time, which indicated a reduction in social recognition ability. In an open field test, a time spent in the center of a field significantly decreased, which indicated a reduction in spontaneous activity. In a light-dark box test, a time spent in a white box significantly decreased, which indicated that anxiety-like behavior was caused. In each of a tail suspension test (TST) and a forced swimming test (FST), an increase in immobility time was found, which indicated that depression-like behavior was shown. Meanwhile, in a locomotion test (LMT), there was no difference in locomotion between the mice exposed to DEX and the control mice. Further, alterations were found in levels of amino acids (glutamate, glutamine, glycine, D-serine, and L-serine) in mouse brains after the neonatal DEX exposure (Non Patent Literature 18). Those amino acids are known to be associated with NMDA receptor mediated neurotransmission. Thus, it is conceivable that alterations in glutamatergic transmission via the NMDA receptor after the neonatal DEX exposure may be involved in the depression-like behavior in the juvenile mice and the adult mice (Non Patent Literature 18).

Figure 2A:
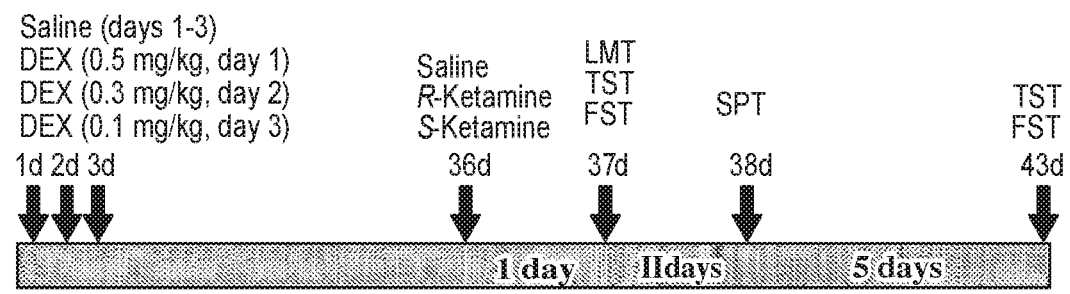
FIG. 2A is a diagram illustrating a test protocol for investigating antidepressant effects of R(−)- and S(+)-ketamine. Tests were performed using mice treated neonatally with dexamethasone (hereinafter referred to as DEX-treated mice) as a new animal model of depression.

The preparation of the animal model of depression and the administration of the agent were specifically performed as described below (FIG. 2A). Male and female ICR mice (9-week-old, Japan SLC, Inc., Hamamatsu, Japan) were used. The mice were given free access to water and feed. A breeding procedure consisted of housing three to four females with one male, for 14 days. On the final day of this period, the females were placed in isolation and checked daily around the expected delivery day. The day of birth was defined as day 0. The mice were injected intraperitoneally with DEX (Wako Pure Chemical Industries, Ltd., Tokyo, Japan) dissolved in saline on day 1, day 2, and day 3 at doses of 0.5 mg/kg body weight, 0.3 mg/kg body weight, and 0.1 mg/kg body weight, respectively. In addition, normal controls were injected with equal volumes (10 ml/kg) of saline. R(−)- or S(+)-ketamine at a dose of 10 mg/kg body weight or vehicle (saline 10 ml/kg) was injected intraperitoneally into male juvenile mice on day 36 after the birth.

The antidepressant effects of the agent were investigated for juvenile mice by behavioral tests such as the TST, the PST, the LMT, and a 1% sucrose preference test (SPT) (FIG. 2A). The TST and the PST were performed twice, i.e., the day (27 hours and 29 hours, respectively) and 7 days after the injection of ketamine, and the LMT and the SPT were performed on the day and 2 days after the injection of ketamine. The TST was performed as described below. First, the mice were taken out from cages, and then a small piece of an adhesive tape was bonded onto a portion approximately 2 cm away from the tip of the tail of the mice. A small hole was opened in the small piece, and the mice were each fixed upside down on a hook through the small hole. The immobility time of each mouse was recorded for 10 minutes. Mice were considered immobile only when they hung passively and completely motionless. The immobility time increases in a depressive state. The PST was performed as described below. First, the mice were placed individually in a cylinder (diameter: 23 cm; height: 31 cm) containing 15 cm of water, maintained at 22 to 24 deg C. The mice were tested in an automated forced-swimming apparatus using SCANET MV-40 (MELQUEST Co., Ltd., Toyama, Japan). The immobility time was calculated as a value obtained by subtracting active time from total time, using the analysis software of the apparatus. Cumulative immobility time was recorded over 6 minutes during a test period. The LMT was performed as described below. First, the mice were placed in experimental cages (length×width×height: 560×560×330 mm). The locomotor activity of the mice was counted with SCANET MV-40, and the cumulative exercise of the mice was recorded for 60 minutes. The cages were cleaned between testing session. The immobility time increases in a depressive state. The SPT was performed by preparing general drinking water and a 1% sucrose solution so that the mice had free access thereto, and measuring the ratio of the amount of the sucrose solution consumed. The consumption of the sucrose solution, which is a reward response, reduces in a depressive state.

Statistical analysis was performed by one-way analysis of variance (one-way ANOVA), followed by a least significant difference test (LSD test). Data are presented as the mean plus minus standard error of the mean (n=8 to 12 mice/group). *$p<0.05$,  $p<0.01$, and *$p<0.001$ indicate significant differences as compared to a DEX-treated mouse group injected with saline, and #$p<0.05$ and ##$p<0.01$ indicate significant differences as compared to a DEX-treated mouse group injected with S(+)-ketamine.

2. Results

Figure 2B:
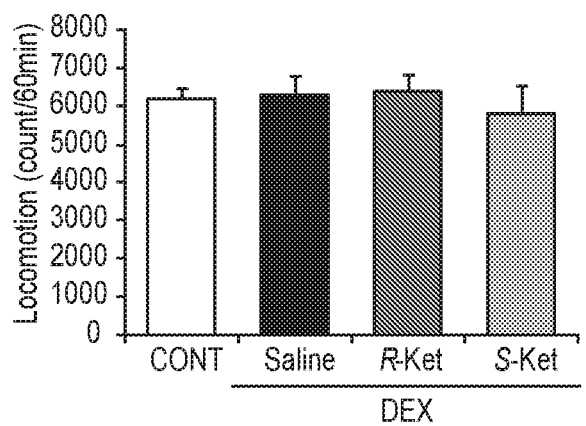
FIG. 2B is a graph showing results of the antidepressant effects of R(−)- and S(+)-ketamine in the DEX-treated mice investigated by the LMT the day after the injection of ketamine.

Significant increases in immobility time in the TST and the FST and a reduction in sucrose consumption preference in the SPT were found in the mice exposed neonatally to DEX as compared to the control mice. On the other hand, in the LMT, there was no difference in locomotion between the DEX-treated mice and the control mice. In the LMT performed on the day after the injection of both the isomers of ketamine, there was no difference in locomotion among the control mice, the DEX-treated mice injected with saline, and the DEX-treated mice injected with R(−)- or S(+)-ketamine (FIG. 2B).

Figure 2C:
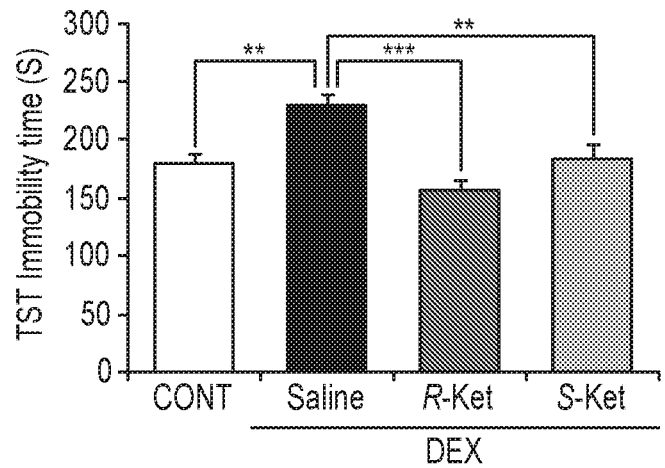
FIG. 2C is a graph showing results of the antidepressant effects of R(−)- and S(+)-ketamine in the DEX-treated mice investigated by the TST the day (27 hours) after the injection of ketamine.
Figure 2D:
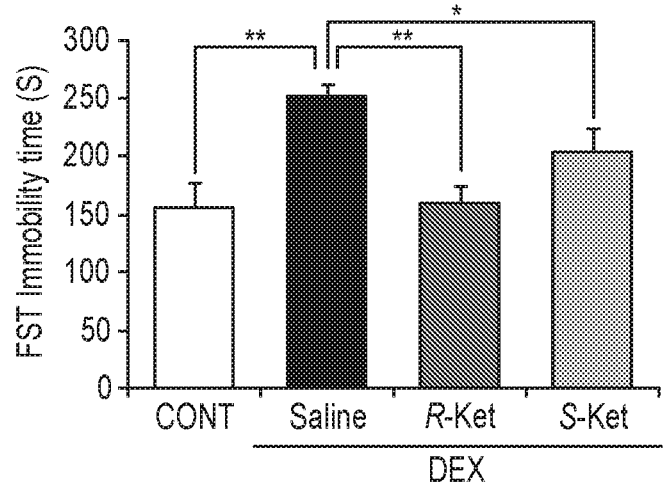
FIG. 2D is a graph showing results of the antidepressant effects of R(−)- and S(+)-ketamine in the DEX-treated mice investigated by the FST the day (29 hours) after the injection of ketamine.

In the TST and FST performed on the day after the injection of both the isomers of ketamine, significant increases in immobility time were found in the DEX-treated mice injected with saline as compared to the control mice. Each of both the isomers of ketamine markedly reduced the immobility time increased in the DEX-treated mice 27 hours or 29 hours after its injection (FIGS. 2C and 2D). R(−)-ketamine exhibited slightly high antidepressant effects as compared to those of S(+)-ketamine, although no significant difference was found there between.

Figure 2E:
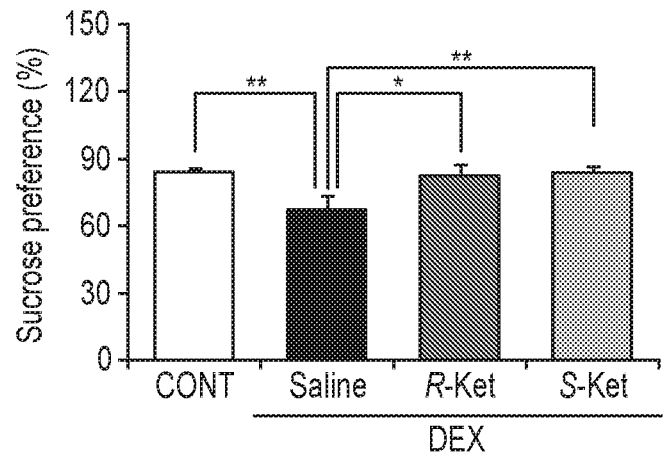
FIG. 2E is a graph showing results of the antidepressant effects of R(−)- and S(+)-ketamine in the DEX-treated mice investigated by the SPT 2 days after the injection of ketamine.

In the SPT performed on 2 days after the injection of both the isomers of ketamine, a reduction in sucrose consumption preference was found in the DEX-treated mice injected with saline as compared to the control mice. Both the isomers of ketamine significantly restored the sucrose consumption preference reduced in the DEX-treated mice 48 hours after their injection (FIG. 2E).

Figure 2F:
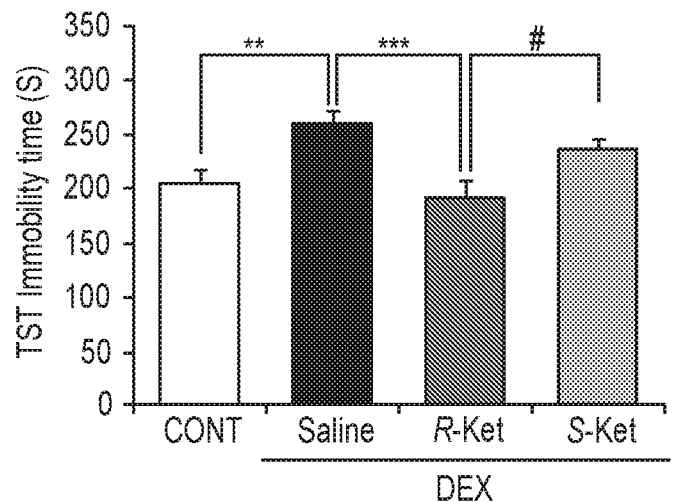
FIG. 2F is a graph showing results of the antidepressant effects of R(−)- and S(+)-ketamine in the DEX-treated mice investigated by the TST 7 days after the injection of ketamine.
Figure 2G:
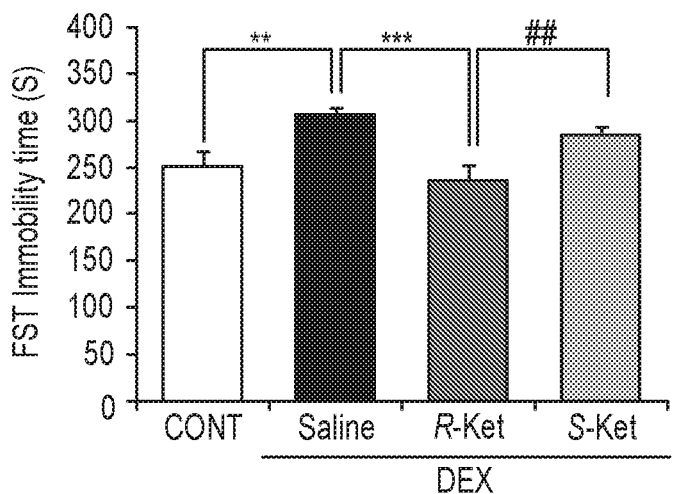
FIG. 2G is a graph showing results of the antidepressant effects of R(−)- and S(+)-ketamine in the DEX-treated mice investigated by the PST 7 days after the injection of ketamine.

In the TST and FST performed on 7 days after the injection of both the isomers of ketamine, significant increases in immobility time were found in the DEX-treated mice injected with saline as compared to the control mice. In addition, R(−)-ketamine significantly reduced the immobility time increased in the DEX-treated mice, whereas S(+)-ketamine did not reduce the immobility time increased in the DEX-treated mice. The differences between R(−)-ketamine and S(+)-ketamine were found to be statistically significant (FIGS. 2F and 2G).

The above-mentioned results revealed that R(−)- and S(+)-ketamine at a dose of 10 mg/kg exhibited antidepressant effects in the juvenile mice after the neonatal DEX exposure (days 1 to 3). In the TST and the FST, the antidepressant effects of both the isomers of ketamine were found 27 to 29 hours after their single injection. It is noteworthy that in the TST and the FST, the antidepressant effects of R(−)-ketamine were able to be detected even 7 days after its single injection, whereas the antidepressant effects of S(+)-ketamine were not able to be detected 7 days after its single injection. The results show that R(−)-ketamine has more long-lasting antidepressant effects than S(+)-isomer. Both the isomers of ketamine are known to exhibit a rapid in vivo clearance. Despite the fact that R(−)-ketamine is considered to be eliminated from the body by 7 days after its single injection, the antidepressant effects were found. This indicates that the differences in antidepressant effects 7 days after the injection of both the isomers of ketamine do not result from differences in pharmacokinetics.

Example 2: Social Defeat Stress Model

A social defeat stress model of depression (Non Patent Literature 19) was used to investigate antidepressant effects of R(−)- and S(+)-ketamine on the depression-like behavior of the animal model. All tests were performed under the approval of the Animal Care and Use Committee of Chiba University.

1. Materials and Methods

R(−)- and S(+)-ketamine hydrochloride were prepared from RS(+/−)-ketamine (Ketalar™, ketamine hydrochloride, Daiichi Sankyo Co., Ltd., Tokyo, Japan) using 0(−)- and L(+)-tartaric acid, respectively, by the method disclosed in the previous report (Patent Literature 2) (FIG. 1). The purity of each of those isomers was confirmed by high-performance liquid chromatography (CHIRALPAKTMIA, column size: 250×4.6 mm, mobile phase; n-hexane/dichloromethane/diethylamine (75/25/0.1), retention time for S(+)-ketamine=6.99 min, retention time for R(−)-ketamine=10.56 min, Daicel Corporation, Tokyo, Japan).

A social defeat stress model of depression was prepared by bringing C57/B6 male mice into contact with ICR male mice (large aggressive mice) for 10 consecutive days to apply a stress called a "social defeat stress" in accordance with the previous report (Non Patent Literature 19). Depression-like behavior was observed in the mice that had received the social defeat stress. Specifically, an increase in immobility time was found in each of a tail suspension test (TST) and a forced swimming test (FST). In addition, in a 1% sucrose preference test, the ratio of sucrose water drunk significantly reduced, suggesting that depression-like behavior (e.g. anhedonia or negative affect) was shown. On the other hand, in a locomotion test (LMT), there was no difference in locomotion between social defeat stress mice and control mice.

Figure 3A:
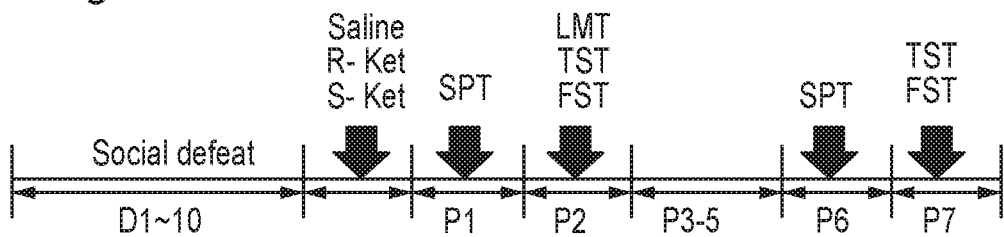
FIG. 3A is a diagram illustrating a test protocol for investigating antidepressant effects of R(−)- and S(+)-ketamine in social defeat stress mice. The social defeat stress mice were prepared by bringing C57/B6 male mice into contact with ICR male mice for 10 consecutive days (D1 to 10). After that, any one of R(−)-ketamine and S(+)-ketamine was injected and various tests were performed on day 1, day 2, day 6, and day 7 (P1, P2, P6, and P7) after the injection.

The preparation of the animal model of depression and the administration of the agent were specifically performed as described below (FIG. 3A). Male C57/B6 mice (7-week-old, Japan SLC, Inc., Hamamatsu, Japan) and ICR mice (9-week-old, Japan SLC, Inc., Hamamatsu, Japan) were used. The mice were given free access to water and feed. A social defeat stress was applied by housing one C57/B6 mouse with one ICR mouse for 10 days. On day 11, a social interaction test was performed to select mice exhibiting depressive symptoms, which were used for the subsequent behavioral evaluation. Control mice were injected with vehicle (saline 10 ml/kg) and the mice exhibiting depressive symptoms were injected intraperitoneally with R(−)- or S(+)-ketamine at a dose of 10 mg/kg body weight, or vehicle (saline 10 ml/kg).

The antidepressant effects of the agent were investigated by behavioral tests such as the TST, the PST, the LMT, and a 1% sucrose preference test (SPT) (FIG. 3A). The 1% sucrose preference test (SPT) was performed on 1 day and 6 days after the injection of ketamine. Each of the TST and the PST was performed on 2 days and 7 days after the injection of ketamine. The TST was performed as described below. First, the mice were taken out from cages, and then a small piece of an adhesive tape was bonded onto a portion approximately 2 cm away from the tip of the tail of the mice. A small hole was opened in the small piece, and the mice were each fixed upside down on a hook through the small hole. The immobility time of each mouse was recorded for 10 minutes. Mice were considered immobile only when they hung passively and completely motionless. The immobility time increases in a depressive state. The PST was performed as described below. First, the mice were placed individually in a cylinder (diameter: 23 cm; height: 31 cm) containing 15 cm of water, maintained at 22 to 24 deg C. The mice were tested in an automated forced-swimming apparatus using SCANET MV-40 (MELQUEST Co., Ltd., Toyama, Japan). The immobility time was calculated as a value obtained by subtracting active time from total time, using the analysis software of the apparatus. Cumulative immobility time was recorded over 6 minutes during a test period. The LMT was performed as described below. First, the mice were placed in experimental cages (length×width×height: 560×560×330 mm). The locomotor activity of the mice was counted with SCANET MV-40, and the cumulative exercise of the mice was recorded for 60 minutes. The cages were cleaned between testing session. The immobility time increases in a depressive state. The SPT was performed by preparing general drinking water and a 1% sucrose solution so that the mice had free access thereto, and measuring the ratio of the amount of the sucrose solution consumed. The consumption of the sucrose solution, which is a reward response, reduces in a depressive state. The mice were decapitated 5 days after the injection of ketamine, and the brain was quickly dissected out and subjected to Golgi staining. A spine density was quantitatively evaluated by observation with a KEYENCE microscope (BZ-9000, Osaka, Japan).

The statistical analysis of the results of the social defeat stress model was performed by one-way analysis of variance (one-way ANOVA), followed by a least significant difference test (LSD test). Data are presented as the mean plus minus standard error of the mean (n=8 to 11 mice/group). *p<0.05, p<0.01, and *p<0.001 indicate significant differences as compared to a social defeat stress mouse group injected with saline, and #p<0.05 indicates a significant difference as compared to a social defeat stress mouse group injected with S(+)-ketamine.

2. Results

Significant increases in immobility time in the TST and the FST and a significant reduction in sucrose consumption preference in the SPT were found in the social defeat stress mice as compared to the control mice. On the other hand, in the LMT, there was no difference in locomotion between the social defeat stress mice and the control mice.

Figure 3B:
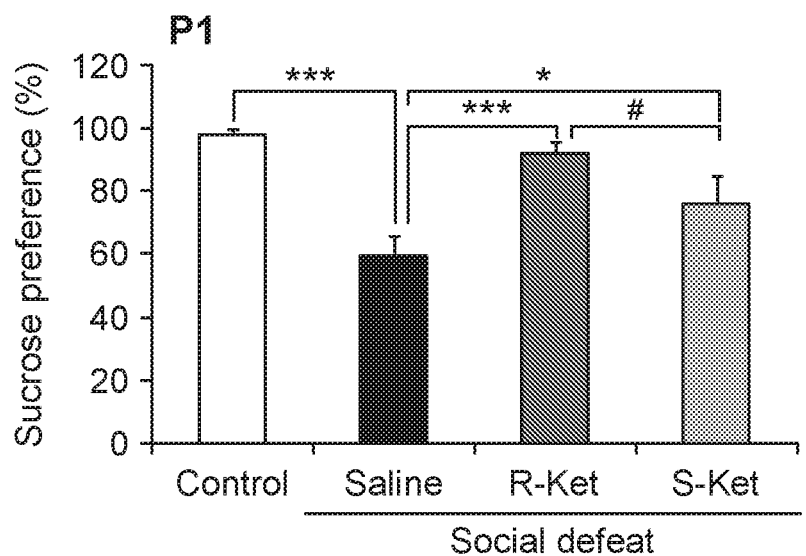
FIG. 3B is a graph showing results of the antidepressant effects of R(−)- and S(+)-ketamine in the social defeat stress mice investigated by the SPT 1 day (P1) after the injection of ketamine.

In the SPT performed on 1 day after the injection of both the isomers of ketamine, in the social defeat stress mice, the sucrose consumption preference significantly decreased as compared to the control group, and depressive symptoms were exhibited. In the social defeat stress mouse group injected with R(−)- or S(+)-ketamine, the sucrose consumption preference significantly increased as compared to the social defeat stress mouse group injected with saline, and depressive symptoms were alleviated. In addition, the antidepressant effects of R(−)-ketamine were more potent than those of S(+)-ketamine (FIG. 3B).

Figure 3C:
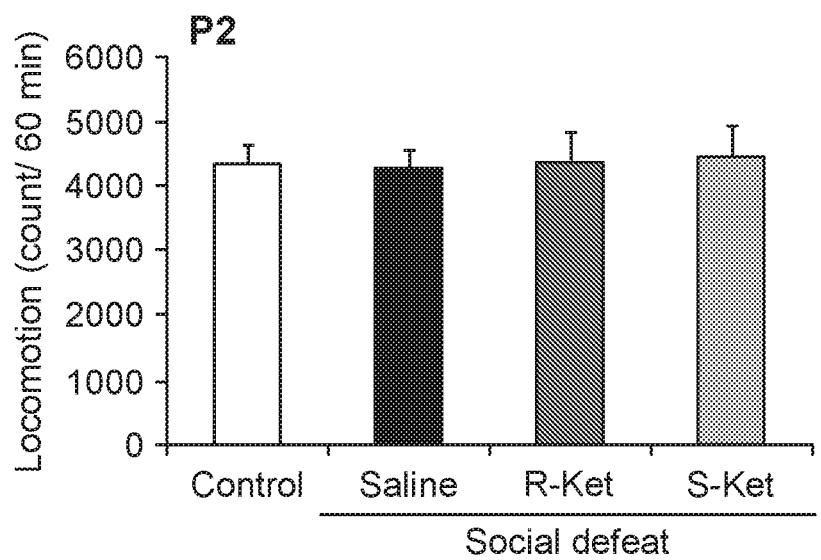
FIG. 3C is a graph showing results of the antidepressant effects of R(−)- and S(+)-ketamine in the social defeat stress mice investigated by the LMT 2 days (P2) after the injection of ketamine.

In the LMT performed on 2 days after the injection of both the isomers of ketamine, there was no difference in locomotion among the normal mice, the social defeat stress mice injected with saline, and the social defeat stress mice injected with R(−)- or S(+)-ketamine (FIG. 3C).

Figure 3D:
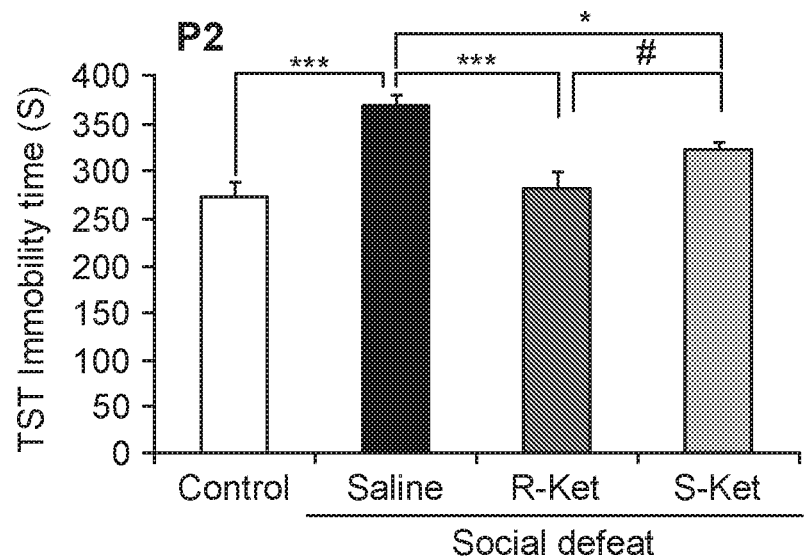
FIG. 3D is a graph showing results of the antidepressant effects of R(−)- and S(+)-ketamine in the social defeat stress mice investigated by the TST 2 days (P2) after the injection of ketamine.
Figure 3E:
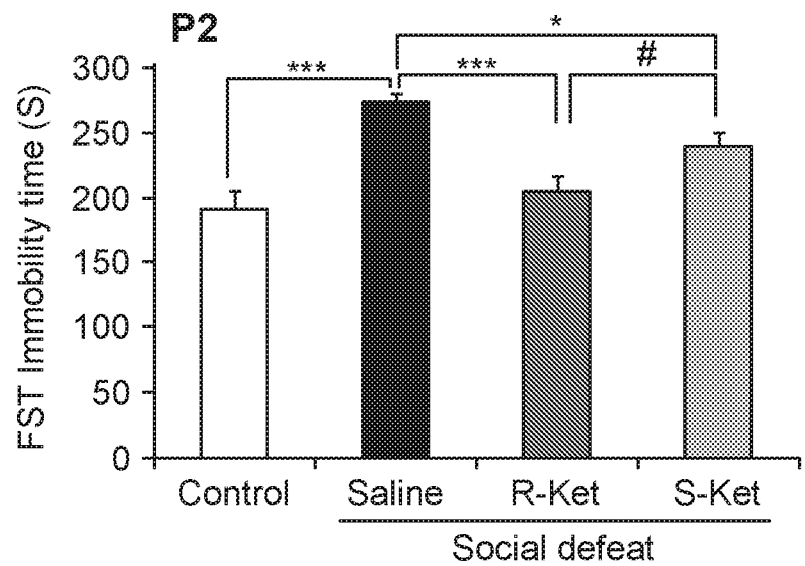
FIG. 3E is a graph showing results of the antidepressant effects of R(−)- and S(+)-ketamine in the social defeat stress mice investigated by the PST 2 days (P2) after the injection of ketamine.

In the TST and FST performed on 2 days after the injection of both the isomers of ketamine, significant increases in immobility time were found in the social defeat stress mice injected with saline as compared to the control mice. Each of both the isomers of ketamine markedly reduced the immobility time increased in the social defeat stress mice 2 days after its injection (FIGS. 3D and 3E). R(−)-ketamine exhibited significant high antidepressant effects as compared to those of S(+)-ketamine (FIGS. 3D and 3E).

Figure 3F:
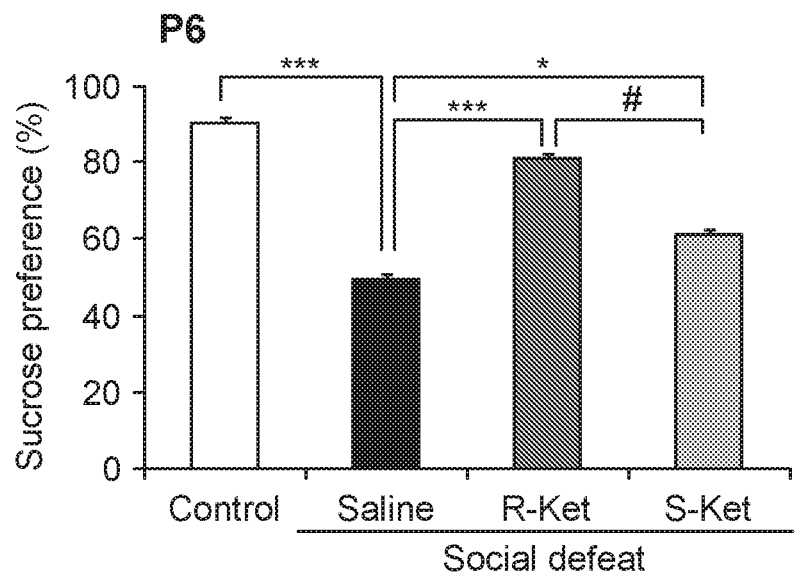
FIG. 3F is a graph showing results of the antidepressant effects of R(−)- and S(+)-ketamine in the social defeat stress mice investigated by the SPT 6 days (P6) after the injection of ketamine.

In the SPT performed on 6 days after the injection of both the isomers of ketamine, a reduction in sucrose consumption preference was found in the social defeat stress mice injected with saline as compared to the control mice. Both the isomers of ketamine significantly restored the sucrose consumption preference reduced in the social defeat stress mice 6 days after their injection. The difference between R(−)-ketamine and S(+)-ketamine was found to be statistically significant (FIG. 3F).

Figure 3G:
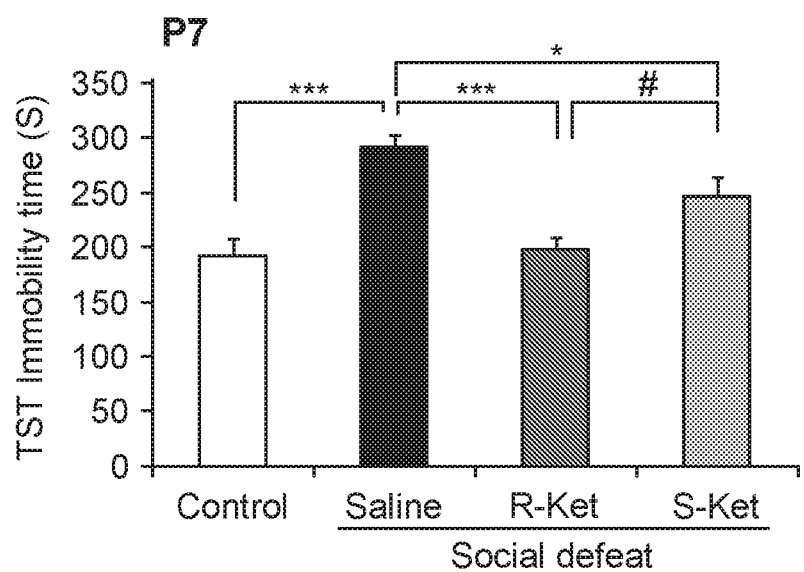
FIG. 3G is a graph showing results of the antidepressant effects of R(−)- and S(+)-ketamine in the social defeat stress mice investigated by the TST 7 days (P7) after the injection of ketamine.
Figure 3H:
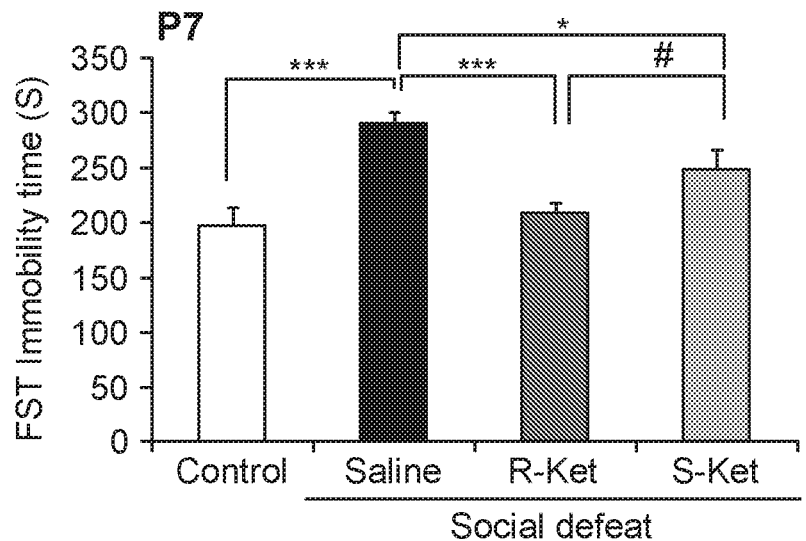
FIG. 3H is a graph showing results of the antidepressant effects of R(−)- and S(+)-ketamine in the social defeat stress mice investigated by the PST 7 days (P7) after the injection of ketamine.

In the TST and FST performed on 7 days after the injection of both the isomers of ketamine, significant increases in immobility time were found in the social defeat stress mice injected with saline as compared to the control mice. Each of both the isomers of ketamine significantly reduced the immobility time increased in the social defeat stress mice 7 days after its injection (FIGS. 3G and 3H). R(−)-ketamine exhibited significantly high antidepressant effects as compared to S(+)-ketamine (FIGS. 3G and 3H).

Figure 3I:
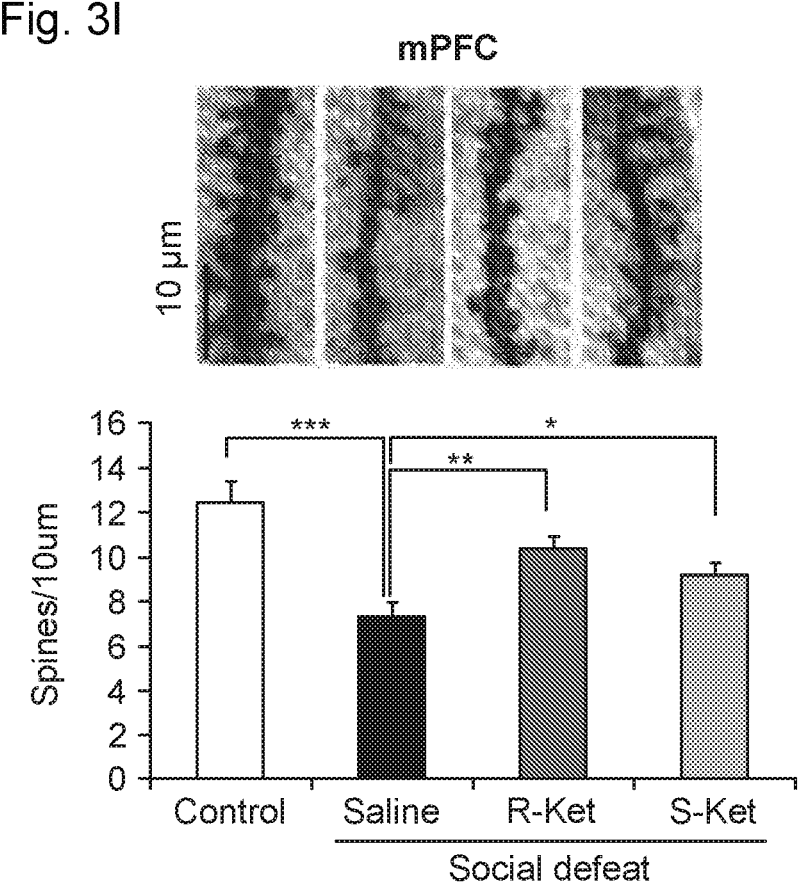
FIG. 3I is a graph showing results of effects of R(−)- and S(+)-ketamine on the spine density of the frontal cortex in the social defeat stress mice investigated 8 days after the injection of ketamine.
Figure 3J:
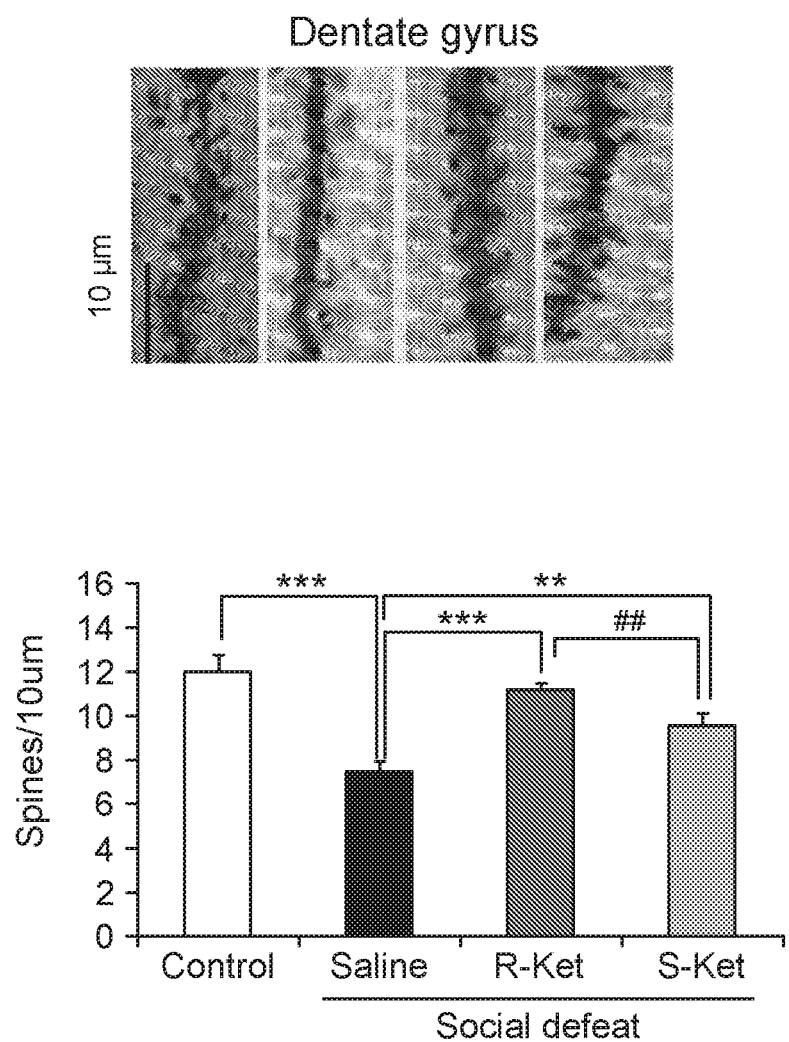
FIG. 3J is a graph showing results of effects of R(−)- and S(+)-ketamine on the spine density of the hippocampal dentate gyrus in the social defeat stress mice investigated 8 days after the injection of ketamine.
Figure 3K:
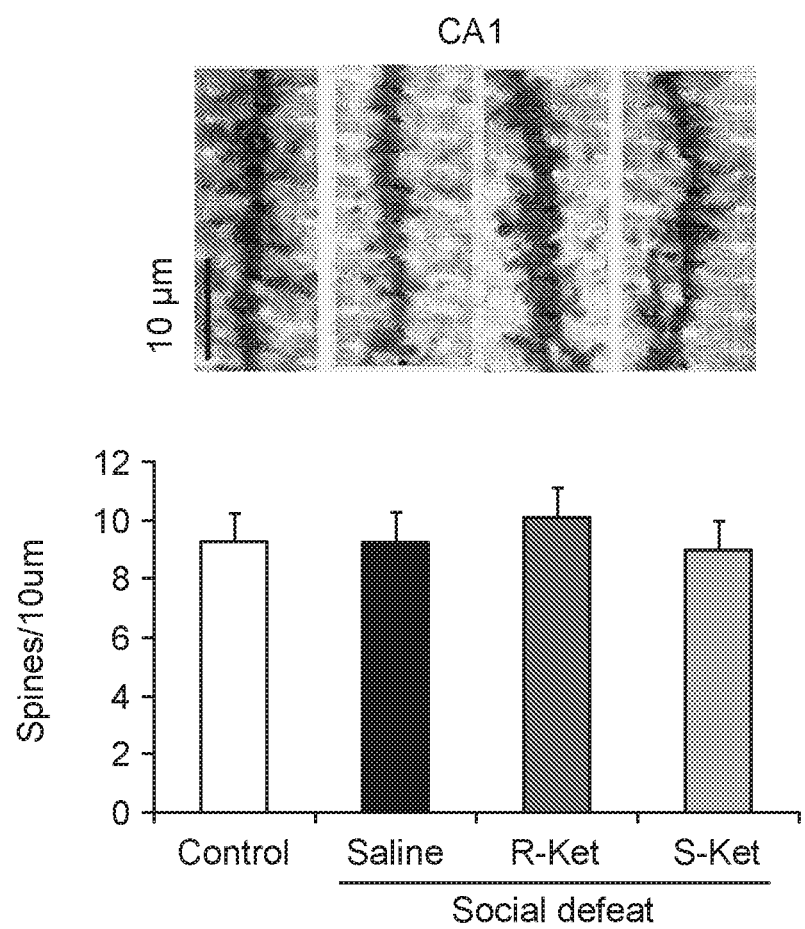
FIG. 3K is a graph showing results of effects of R(−)- and S(+)-ketamine on the spine density of the hippocampus CA1 region in the social defeat stress mice investigated 8 days after the injection of ketamine.
Figure 3L:
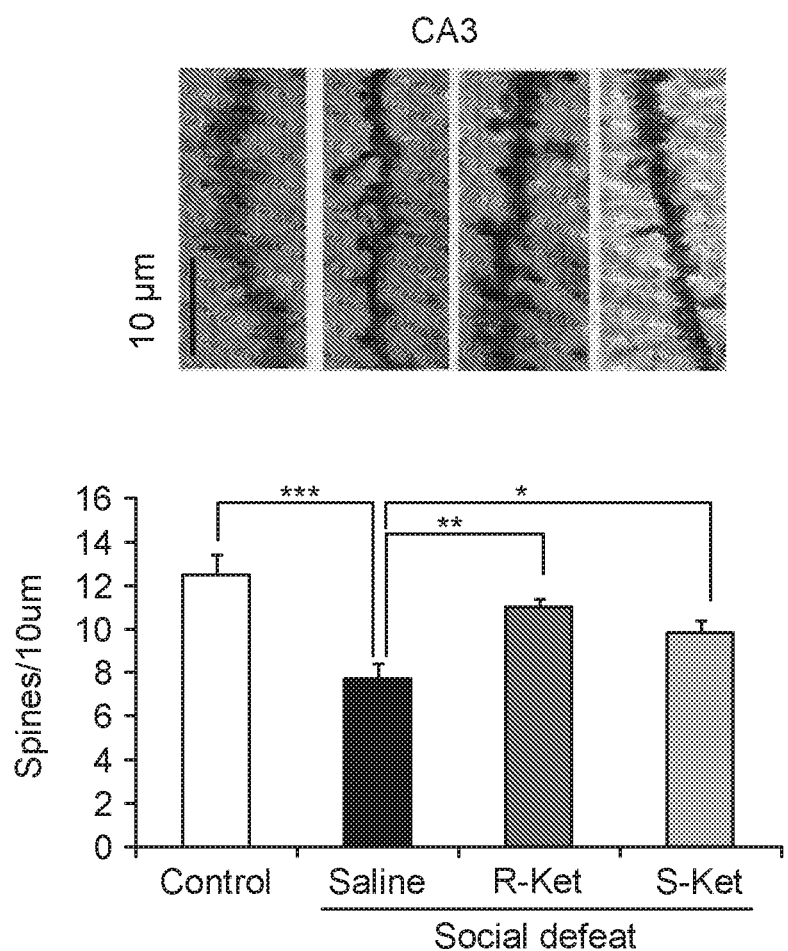
FIG. 3L is a graph showing results of effects of R(−)- and S(+)-ketamine on the spine density of the hippocampus CA3 region in the social defeat stress mice investigated 8 days after the injection of ketamine.
Figure 3M:
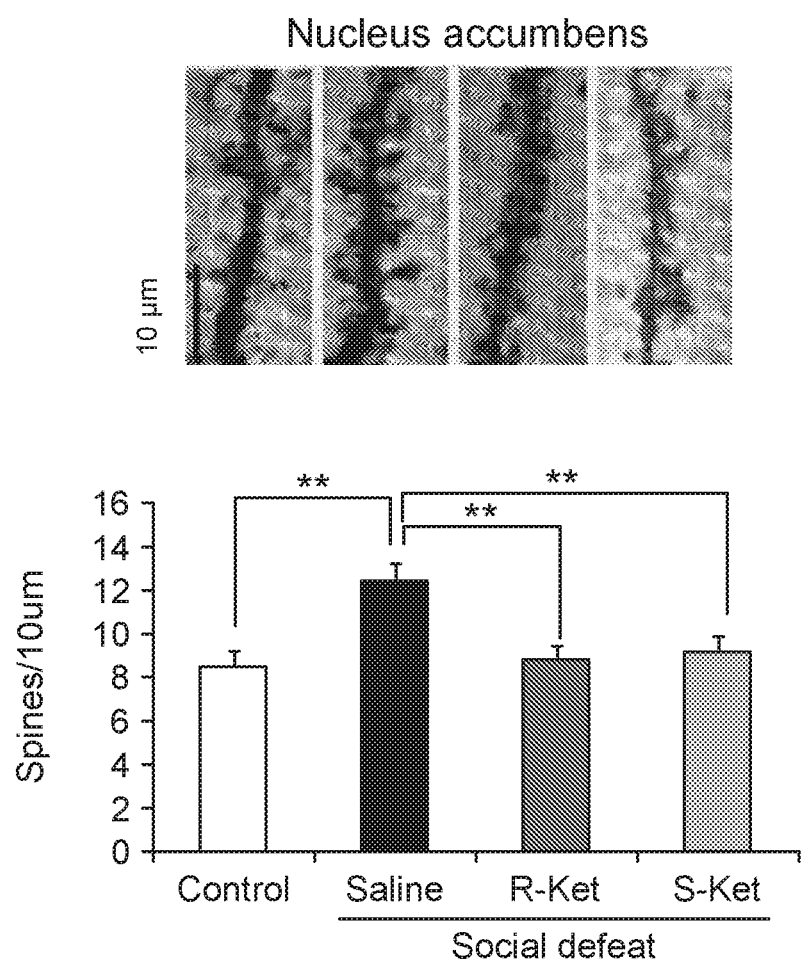
FIG. 3M is a graph showing results of effects of R(−)- and S(+)-ketamine on the spine density of the nucleus accumbens in the social defeat stress mice investigated 8 days after the injection of ketamine.
Figure 3N:
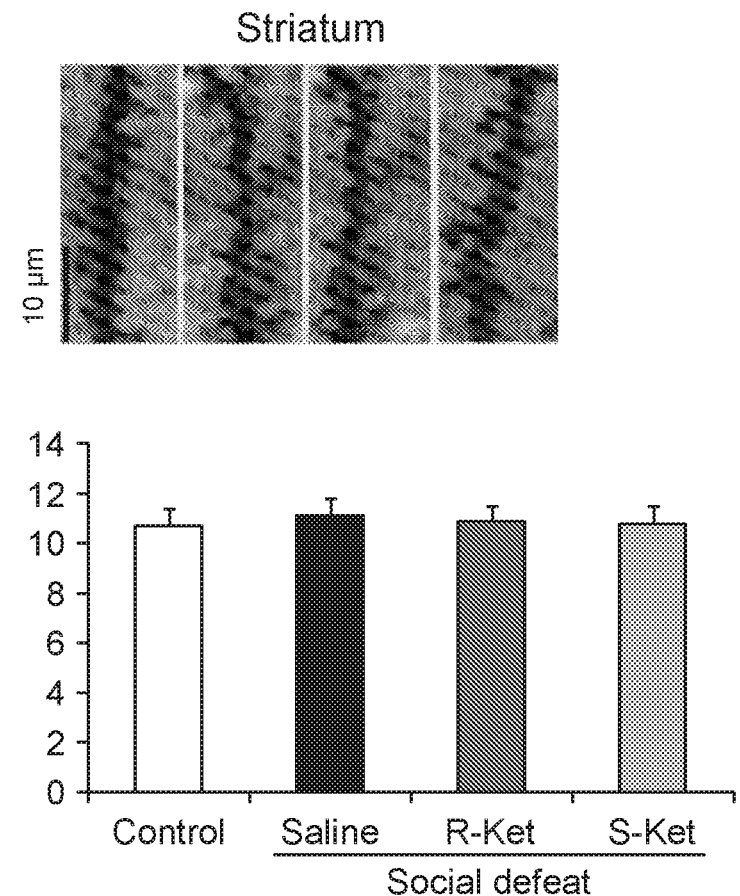
FIG. 3N is a graph showing results of effects of R(−)- and S(+)-ketamine on the spine density of the striatum in the social defeat stress mice investigated 8 days after the injection of ketamine.

In the Golgi staining performed 8 days after the injection of both the isomers of ketamine, a significant decrease in spine density was found in the frontal cortex and hippocampal dentate gyrus of the social defeat stress mice injected with saline as compared to the control mice. Each of both the isomers of ketamine significantly improved the decreased density of spine in the social defeat stress mice 8 days after its injection (FIGS. 3I and 3J). In the hippocampal dentate gyrus, R(−)-ketamine showed more significant improvement in the restoration of spine density as compared to S(+)-ketamine (FIG. 3J). In the hippocampus CA1 region and striatum, no apparent change in spine density was observed (FIGS. 3K and 3N), while in hippocampus CA3 region, a decrease in spine density by social defeat stress was observed, which was significantly improved by R(−)-ketamine and S(+)-ketamine (FIG. 3L). In the nucleus accumbens, a significant increase in spine density was observed by social defeat stress, which was significantly improved by R(−)-ketamine and S(+)-ketamine (FIG. 3M).

The above-mentioned results revealed that R(−)- and S(+)-ketamine at a dose of 10 mg/kg exhibited antidepressant effects in the social defeat stress mice. It is noteworthy that in the SPT, the TST, and the PST, the antidepressant effects of R(−)-ketamine were significantly potent as compared to the effects of S(+)-ketamine. The results show that R(−)-ketamine has more long-lasting antidepressant effects than S(+)-isomer. Both the isomers of ketamine are known to exhibit a rapid in vivo clearance. Despite the fact that R(−)-ketamine is considered to be eliminated from the body by 7 days after its single injection, the antidepressant effects were found. This indicates that the differences in antidepressant effects 7 days after the injection of both the isomers of ketamine do not result from differences in pharmacokinetics.

Example 3: Additional Effects of R(−)-Ketamine Administration

Control C57/B6 mice was used to investigate side effects of R(−)- and S(+)-ketamine. All tests were performed under the approval of the Animal Care and Use Committee of Chiba University.

1. Materials and Methods

The preparation of R(−)- and S(+)-ketamine hydrochloride and the confirmation of their purities were performed by the methods described in Example 2.

The administration of an agent was performed by the same methods as the methods described in Example 2.

The side effects of R(−)- and S(+)-ketamine were investigated by a locomotion enhancing effect, disruption of prepulse inhibition, and a dependence test using a conditioned place preference test, which were systems for evaluating side effects.

An effect of ketamine on the locomotion of mice was tested using SCANET MV-40 (MELQUEST Co., Ltd., Toyama, Japan). Specifically, the locomotion was measured for a total of 180 minutes, i.e., 60 minutes before injection to 120 minutes after injection, and calculated as a locomotion per 10 minutes. The statistical analysis of the results of the locomotion was performed by repeated one-way analysis of variance (repeated one-way ANOV A), followed by a least significant difference test (LSD test). Data are presented as the mean plus minus standard error of the mean (n=7 or 8 mice/group). p<0.01 and *p<0.001 indicate significant differences as compared to a group injected with saline.

The prepulse inhibition test was performed using a startle response system (SR-LAB, SanDiego Instruments, San Diego, Calif., United States). The analysis of the results of prepulse inhibition was performed by multivariate analysis of variance (MANOVA), followed by a least significant difference test (LSD test). Data are presented as the mean plus minus standard error of the mean (n=10 to 12 mice/group). *p<0.05 and p<0.01 indicate significant differences as compared to a group injected with saline.

The place preference test was performed using a conditioned place preference test apparatus (BrainScienceIdea Co., Ltd., Osaka, Japan). The analysis of the results of the place preference test was performed by one-way analysis of variance (one-way ANOVA), followed by a least significant difference test (LSD test). Data are presented as the mean plus minus standard error of the mean (n=9 or 10 mice/group). *p<0.05 and **p<0.01 indicate significant differences as compared to a group injected with saline.

2. Results

Figure 4:
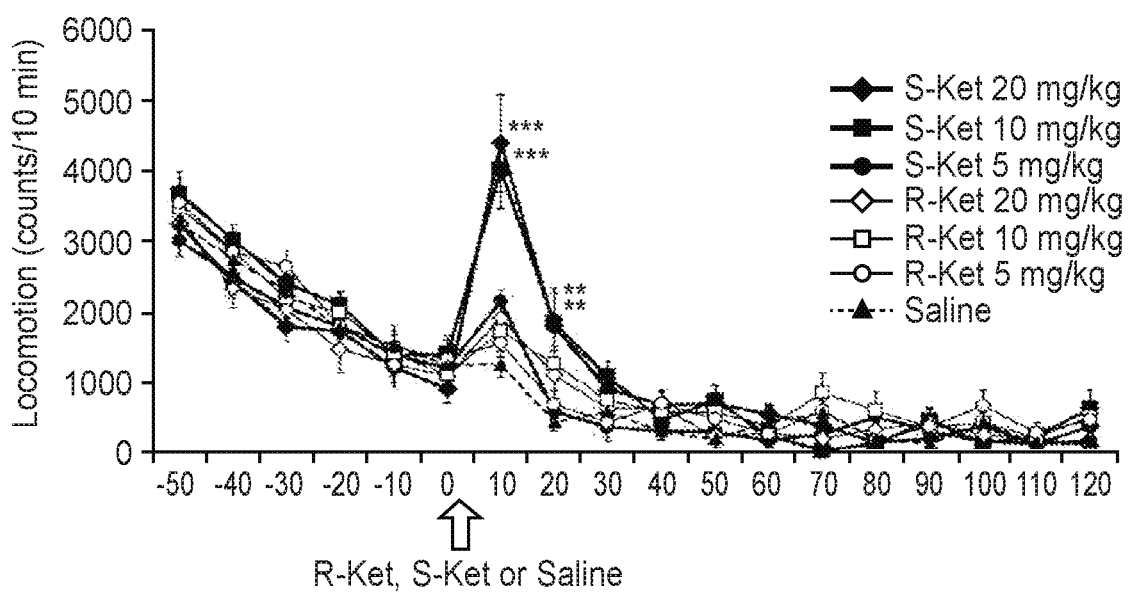
FIG. 4 is a graph showing time-dependent changes in locomotion of control mice after the injection of R(−)- and S(+)-ketamine.

In the measurement of the locomotion after the injection of both the isomers of ketamine, a significant increase in locomotion was found 10 minutes and 20 minutes after the injection in the mice injected with S(+)-ketamine (10 mg/kg or 20 mg/kg) as compared to the control mice injected with saline. The locomotion was transiently enhanced by S(+)-ketamine (10 mg/kg or 20 mg/kg), but returned to a normal value 30 minutes after the injection. On the other hand, the injection of R(−)-ketamine (5, 10, or 20 mg/kg) did not affect the locomotion (FIG. 4).

Figure 5A:
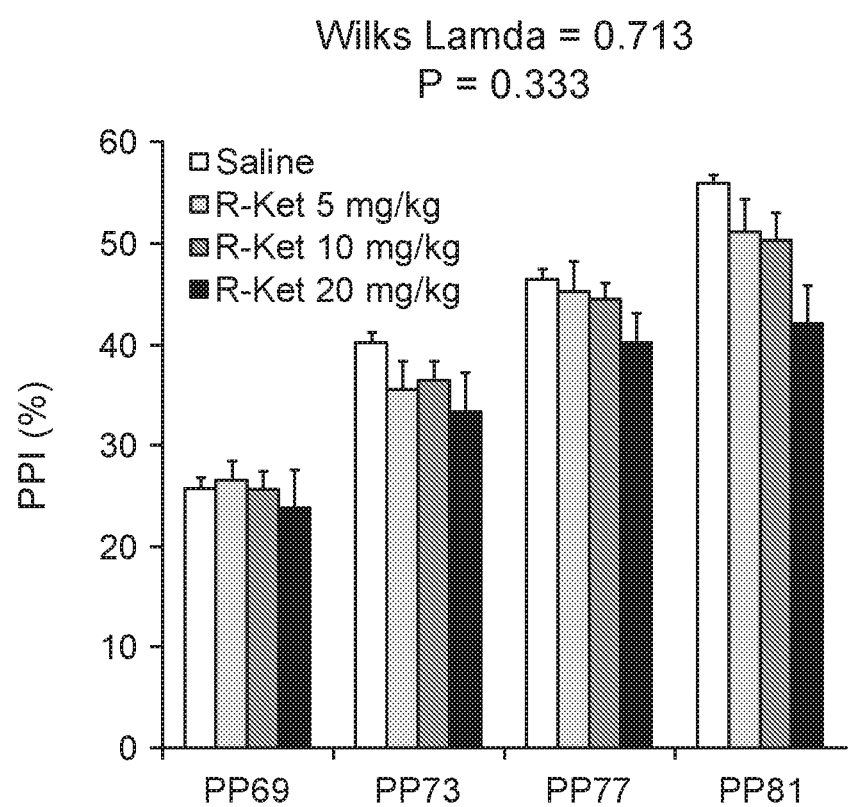
FIG. 5A is a graph showing changes in prepulse inhibition after the injection of R(−)-ketamine in control mice.
Figure 5B:
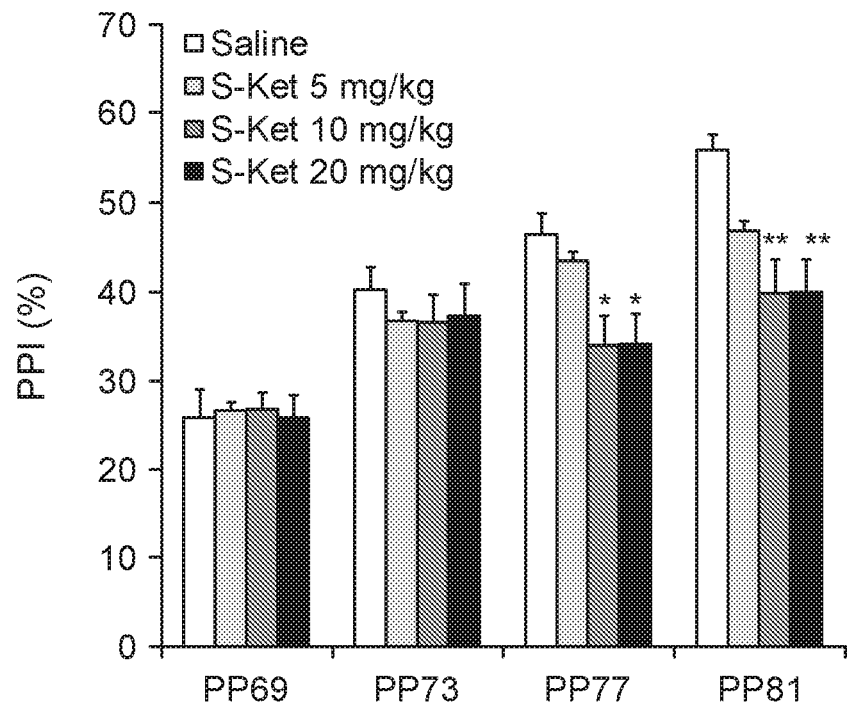
FIG. 5B is a graph showing changes in prepulse inhibition after the injection of S(+)-ketamine in the control mice.

In the prepulse inhibition test after the injection of both the isomers of ketamine, the injection of S(+)-ketamine (5, 10 mg/kg, or 20 mg/kg) disrupted prepulse inhibition in a dose-dependent manner (FIG. 5B). On the other hand, the injection of R(−)-ketamine (5, 10, or 20 mg/kg) did not disrupt prepulse inhibition (FIG. 5A).

Figure 6C:
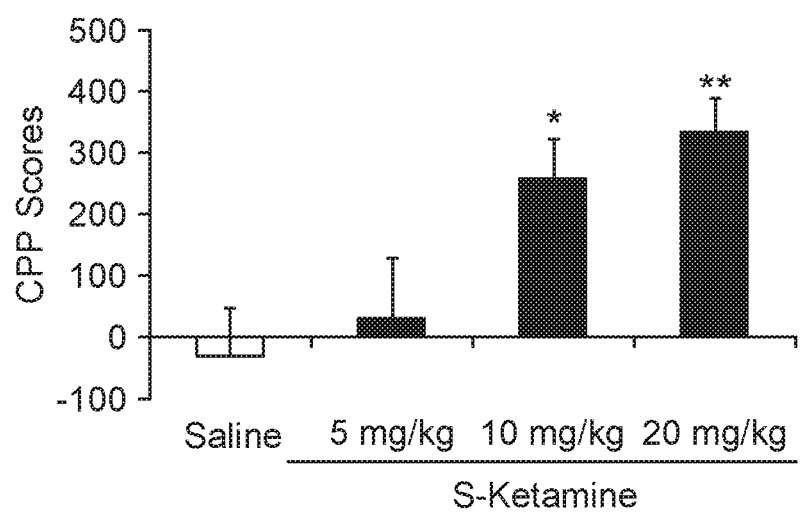
FIG. 6C is a graph showing results of the rewarding effects of S(+)-ketamine on the control mice using the conditioned place preference test.
Figure 6D:
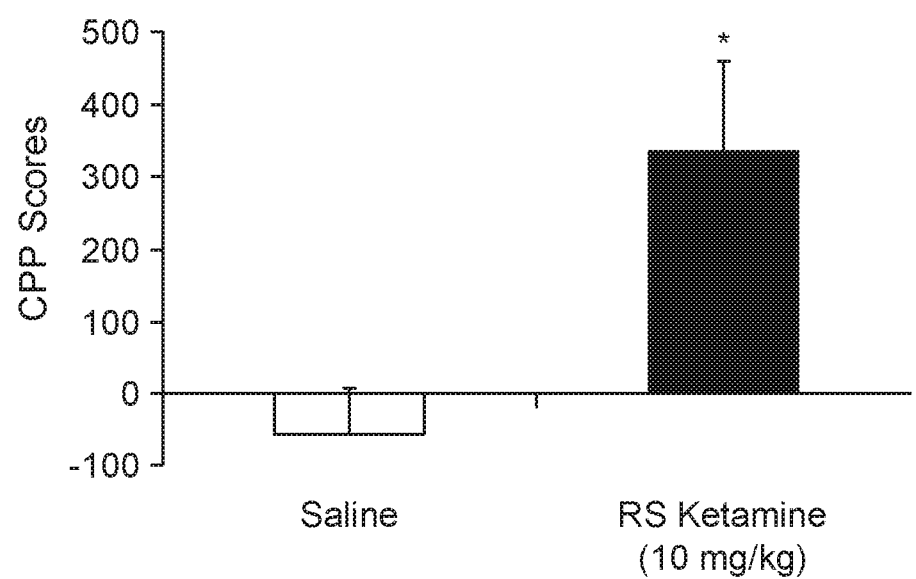
FIG. 6D is a graph showing results of the rewarding effects of RS(+/−)-ketamine on the control mice using the place preference test.

In the conditioned place preference test after the injection of both the isomers and racemic mixture of ketamine, the injection of S(+)-ketamine (5, 10 mg/kg, or 20 mg/kg) increased the CPP score in a dose-dependent manner, indicating drug abuse potential (FIG. 6C). On the other hand, the injection of R(−)-ketamine (5, 0, or 20 mg/kg) did not increase the CPP score (FIG. 6B), indicating no drug abuse potential. In addition, the injection of RS(+/−)-ketamine (10 mg/kg) significantly increased the CPP score, indicating drug abuse potential (FIG. 6D).

As described above, from the viewpoint of side effects, the injection of S(+)-ketamine was found to exhibit a locomotion-enhancing effect, disrupt prepulse inhibition, and produce drug dependence. In addition, it was suggested that the injection of RS(+/−)-ketamine also produced drug dependence. On the other hand, R(−)-ketamine does not exhibit a locomotion-enhancing effect, disrupt prepulse inhibition, and produce drug dependence, for example, and hence is an agent having high safety as compared to RS(+/−)-ketamine and S(+)-ketamine that are clinically used at present.

Example 4: R(−)-Ketamine Attenuates Morphine Induced Conditioned Place Preference The abuse of drugs is linked to their ability to produce specific subjective effects in humans (e.g., euphoria). Abuse liability of morphine in rats in a model predictive of abuse in humans (Napier et al., 2014; Tzschentke, 2007). Rodents, like humans, show a preference for the place where morphine is administered (Suzuki et al., 2000) and this conditioned-place preference has been used to predict the abuse liability of drugs; drugs that produce a preference to the place associated with a drug are drugs that are abused by humans. Morphine induces conditioned place-preference (CPP) in rats. In the presence of @-ketamine, this conditioned place preference was diminished (p=0.06). Since ketamine itself can produce CPP (Li et al., 2008; Suzuki et al., 2000), the finding that R-ketamine blocked the CPP induced by morphine was unexpected.

A conditioned place preference study was conducted in mice to determine the effects of R(−)-ketamine on attenuating the rewarding effects of morphine.

Figure 7A:
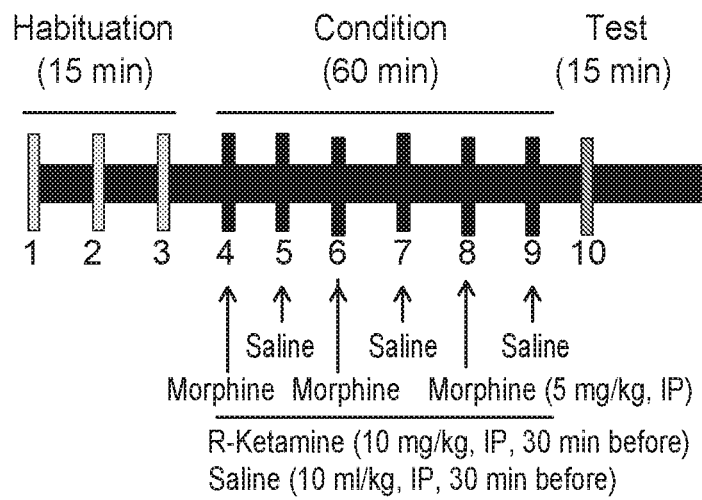
FIG. 7A-B show that R(−)-ketamine co-dosed with morphine produced a trend towards attenuating the conditioned place preference induced by morphine (p=0.06).

The methods for conditioned place preference and evaluation of R-ketamine were conducted using the general methods of Suzuki et al. (2000). The general design was to dose mice with either saline+saline, saline+morphine, or R-ketamine+morphine and evaluate their preference for the morphine-associated place. Morphine was given at 5 mg/kg, i.p. and R-ketamine was dosed at 10 mg/kg, i.p. The training and testing scheme is shown in FIG. 7A.

Male ddY mice (20-23 g) were obtained from Tokyo Experimental Animals Inc. (Tokyo, Japan). The ddY mice were bred in a closed colony. The mice were housed at a temperature of 22 f 1° C. with a 12-h light-dark cycle (light on 8:30 a.m. to 8:30 p.m.). Food and water were available ad libitum.

Place conditioning was conducted as described previously, using a minor modification of a biased procedure according to Suzuki et al. (2000). The apparatus consisted of a shuttlebox (15×30×15 cm: w×l×h) made of an acryl-resin board. The box was divided into two compartments of equal size by means of a sliding partition. One compartment was white with a textured floor; the other was black with a smooth floor. For conditioning mice were immediately conditioned to the white compartment following drug injection and to the black compartment following vehicle injection.

Conditioning sessions were conducted once daily for 6 consecutive days. Mice were injected with morphine (5 mg/kg)+vehicle or R(−)-ketamine (10 mg/kg)+morphine (5 mg/kg) and placed into one compartment of the chamber. On the next day mice were injected with saline and placed into the other compartment. From day 3, this cycle (session) for the conditioning was repeated two more times. Each session was 60 min in duration. On day 7 tests were performed as follows: the partition separating the two compartments was raised to 7 cm above the floor, and a neutral platform was inserted along the seam separating the compartments. Preference for a particular place was assessed in the drug-free state after placing the animals on the neutral platform and allowing them free access to both compartments. The time spent in each compartment during a 900-sec session was then measured automatically in a blinded fashion by two infrared beam sensors (KN-80, Natsume Seisakusyo, Tokyo, Japan) on the covers (3 cm from the center and the side) of the white and black compartments. The position of the mouse was defined by the position of its whole body. All sessions were conducted under conditions of dim illumination and masking white noise.

Conditioning scores represent the time spent in the drug-paired place minus the time spent in the vehicle-paired place, and are expressed as the mean±S.E.M. Behavioral data were evaluated statistically with a one-way analysis of variance (ANOVA) followed by Dunnett's test to determine whether individual doses produced significant conditioning.

Figure 7B:
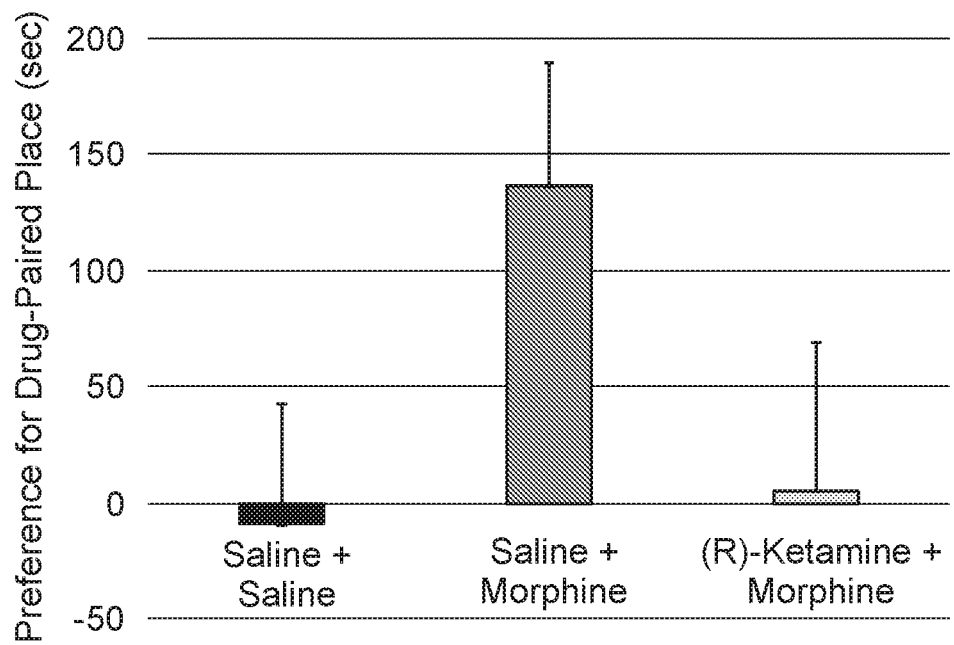

Given the assumption that R-ketamine would not block the rewarding effects of morphine, the data in FIG. 7B showed a trend toward significant attenuation F(2,29)=2.2, p=0.064. This effect suggests that R(−)-ketamine attenuates the reinforcing or rewarding effects produced by morphine that are associated with its abuse.

The abuse of drugs is linked to their ability to produce specific subjective effects in humans (e.g., euphoria). Conditioned place preference models in rodents that show the abuse liability of morphine are predictive of abuse in humans (Napier et al., 2014; Tzschentke, 2007). Rodents, like humans, show a preference for the place where morphine is administered (Suzuki et al., 2000) and this conditioned-place preference has been used to predict the abuse liability of drugs: drugs that produce a preference to the place associated with a drug are drugs that are abused by humans. FIG. 7B shows morphine-induced conditioned place-preference (CPP) in rats. In the presence of R-ketamine, this conditioned place preference was diminished (p=0.06). Since ketamine itself can produce CPP (Li et al., 2008; Suzuki et al., 2000), the finding that R-ketamine blocked the CPP induced by morphine was unexpected.

Example 5: R(−)-Ketamine Attenuates Withdrawal Signs from Naloxone-Precipitated Withdrawal from Subchronic Morphine One consequence of taking drugs of abuse is the development of drug dependence that is expressed upon drug withdrawal. Opioids such as morphine elicit a physical dependence upon repeated usage which may manifest as an aversive withdrawal state upon cessation of use. Avoidance of this withdrawal state is regarded as a significant driver of continued usage. Opioid dependence can be induced in rats through twice daily administration of morphine. After 9-12 days of treatment, withdrawal can be triggered by an acute injection of the opioid receptor antagonist naloxone (Erami et al, 2012). Over the next 30 min, a cluster of behaviors expressed by the animal, including elevated startle/hyperreactivity, ptosis (eye closure), hypolocomotion, chewing, and tremors/twitches are expressed, which translate into some of the clinical signs of opioid withdrawal in humans (see Higgins and Sellers, 2004). The rats may also demonstrate a hypolocomotive state which may also reflect the dysphoric nature of a withdrawal state. The purpose of this study is to investigate the effect of R-ketamine against the somatic signs of a naloxone precipitated opioid withdrawal. The alpha-2A adrenoceptor agonist Lofexidine (Lucemyra®: FDA approved medication for treatment of opioid withdrawal), will be included as a positive control.

A study was conducted to determine whether R(−)-ketamine would attenuate the withdrawal signs from naloxone-precipitated withdrawal from subchronic morphine in rats.

General methods were according to those of Higgins et al. (1993), where rats were made physically-dependent upon morphine by daily administration. The ability of R(−)-ketamine to attenuate withdrawal signs induced by naloxone was assayed. The 10 and 20 mg/kg doses of R(−)-ketamine are based on published dose ranges for ketamine (see Gastambide et al, 2013: Hillhouse and Porter, 2013; Nikiforuk & Popik, 2014).

Forty (40) male Wistar rats served as test subjects in this study. Animals were pair housed with unrestricted access to rodent chow and water (SOP ROD.03.01, SOP ROD.04.01, SOP ROD.18). They were maintained on a 12 h/12 h light/dark cycle. All experimental activity occurring during the animals' light cycle. All animal use procedures were performed in accordance with the principles of the Canadian Council on Animal Care (CCAC).

The effect Of R(−)-Ketamine against somatic withdrawal signs of a naloxone precipitated opioid withdrawal were measured. Naloxone (Narcan, Evzio) is a medication designed to rapidly reverse opioid overdose. Naloxone is an opioid antagonist that binds to opioid receptors, blocking the effects of other opioids such as morphine.

Forty (40) male Wistar rats were assigned to 5 groups of N=8 rats per group. Group A was dosed with saline vehicle (Sal; subcutaneous (SC) route) twice daily (approx. 08:00±1 h and 18:00±1 h) for 12 days. Groups B, C, D, and E were dosed with morphine solution (10 mg/kg; SC route) twice daily (approx. 08:00±1 h and 18:00±1 h) for 12 days. This treatment regimen was designed to induce opioid dependence (Erami et al., 2012). Previous in-house studies have demonstrated that this injection schedule results in morphine plasma levels of ~550 ng/ml (measured 2 h post dose on days 3, 6, 9 and 12). On days 9 and 12, rats were tested for naloxone precipitated withdrawal. According to a cross-over design (see Table 4: Treatment Groups), all rats in each group received either acute saline, or naloxone hydrochloride (1 mg/kg; dose volume 2 ml/kg) injection by the SC route, 5 minutes prior to behavioral testing. Preceding each treatment (10 minutes) rats received either saline (Groups A and B), R(−)-ketamine (Group B and C), or Lofexidine (Group E) on both days. In this way, the effect of R(−)-ketamine was examined against an opioid precipitated withdrawal. Lofexidine doses are based on literature values (e.g. Shearman et al., 1979). Immediately after vehicle or naloxone injection, rats were transferred to activity chambers for 30 minutes where the animals were visually assessed for somatic signs associated with opioid withdrawal (e.g. writhes, chews, ptosis, WDS, shakes, tremor, penile grooming, body weight change; see Higgins and Sellers, 1994). Simultaneously, the activity pattern (distance travelled, rearing) of each rat was automatically recorded.

Locomotor activity. Spontaneous activity in the rats was measured with the automated Med Associates activity test chamber for 30 minutes with 10-minute time bins. The tracking arena was 17"W×17"L×12"H, sensor bars are secured 1" above the floor to track distance travelled, and a second set of sensor bars are placed ~5" above the floor to measure vertical movement and rearing activity. The parameters set on the tracking software were as follows: resolution—50 milliseconds (ms), box size—4 beams, resting delay—500 ms, and ambulatory trigger—2 (SOP ROD.25). Data included total distance traveled, rearing counts and ambulatory counts.

Immediately following behavioral testing on Day 12, a terminal blood sample was collected from N=3 rats from Groups B, C, and D with naloxone treatment (SOP ROD. 14.03). Morphine concentration was measured from all samples (i.e. 9 in total), and R(−)-ketamine was measured from groups C and D (i.e. 6 in total). Blood was collected into EDTA tubes, gently mixed following collection and placed on wet ice. Blood samples were centrifuged (2500 g for 10 min at approximately 4° C.) and plasma was extracted. Samples were stored at −80° C. until shipment.

This data was used to calculate the total withdrawal score shown in FIG. 8.

TABLE 3

Schedule of Events

| Study Day | Key Event | Details |
|---|---|---|
| −7 | Animal arrival | Acclimation to the test facility |
| 1-8 | Morphine dosing | Twice daily morphine/vehicle administration |

TABLE 3-continued

Schedule of Events

| Study Day | Key Event | Details |
|---|---|---|
| 9 | Morphine withdrawal test #1 | Cross-over design<br>Morphine administration at T = −2 hrs<br>Treatment with Vehicle, (R)-ketamine, or Lofexidine at T = −15 min<br>Treatment with saline or Naloxone at T = −5 mins<br>Assessment of somatic signs and activity at T = 0-30 mins<br>Daily observations<br>Morphine administration in PM |
| 10, 11 | Morphine dosing | Twice daily morphine/vehicle administration<br>Daily observations |
| 12 | Morphine withdrawal test #2 | Cross-over design<br>Morphine administration at T = −2 hrs<br>Treatment with vehicle, (R)-ketamine, or Lofexidine at T = −15 min<br>Treatment with saline or Naloxone at T = −5 mins<br>Assessment of somatic signs and activity at T = 0-30 mins<br>Daily observations<br>Terminal Blood Collections |

TABLE 4

Treatment groups

| | Group | | | | |
|---|---|---|---|---|---|
| | A | B | C | D | E |
| Treatment A | Vehicle SC b.i.d. | Morphine 10 mg/kg SC b.i.d. | Morphine 10 mg/kg SC b.i.d. | Morphine 10 mg/kg SC b.i.d | Morphine 10 mg/kg SC b.i.d. |
| Treatment B | Vehicle | Vehicle | (R)-Ketamine 10 mg/kg IP | (R)-Ketamine 20 mg/kg IP | Lofexidine 0.25 mg/kg IP |
| Treatment C | Vehicle/Naloxone 1 mg/kg SC | Vehicle/Naloxone 1 mg/kg SC | Vehicle/Naloxone 1 mg/kg SC | Vehicle/Naloxone 1 mg/kg SC | Vehicle/Naloxone 1 mg/kg SC |

One consequence of substance use disorders is the development of drug dependence that is expressed upon drug withdrawal. Opioids such as morphine elicit a physical dependence upon repeated usage which may manifest as an aversive withdrawal state upon cessation of use. Avoidance of this withdrawal state is regarded as a significant driver of continued usage. Opioid dependence can be induced in rats through twice daily administration of morphine. After 9-12 days of treatment, withdrawal can be triggered by an acute injection of the opioid receptor antagonist naloxone (Erami et al, 2012). Over the next 30 min, a cluster of behaviors is expressed by the animal, including elevated startle/hyperreactivity, ptosis (eye closure), hypolocomotion, chewing, and tremors/twitches are expressed, which translate into some of the clinical signs of opioid withdrawal in humans (see Higgins and Sellers, 2004). The rats may also demonstrate a hypolocomotive state, which may also reflect the dysphoric nature of a withdrawal state. Here, the effects of R-ketamine against the somatic signs of a naloxone precipitated opioid withdrawal were investigated. The alpha-2A adrenoceptor agonist Lofexidine (Lucemyra®: FDA approved medication for treatment of opioid withdrawal), was included as a positive control.

Morphine dependence was created in rats by daily dosing. An opioid receptor antagonist, naloxone was then administered to precipitate withdrawal. Withdrawal signs after naloxone included wet-dog shakes and the like that were not produced in non-morphine dependent rats ($p<0.05$). R-ketamine, given just prior to naloxone, significantly attenuated the naloxone-induced withdrawal signs ($p<0.05$) as did the FDA-approved drug lofexidine ($p<0.05$). R(−)-ketamine, when given just before naloxone, significantly attenuated the withdrawal signs.

Example 6: R(−)-Ketamine Blocks Ethanol Tolerance

Tolerance is a common effect of exposure to drugs of abuse; this diminishment of drug effect after prior drug exposure plays important roles in drug abuse and drug dependence (Miller et al., 1987). Tolerance to the effects of ethanol on day 2 after giving two high dose exposures of ethanol on day 1 was produced in rats. This tolerance to the effect of ethanol on motor-impairment ($p<0.05$) was blocked by R-ketamine ($p<0.05$).

A study in rats was conducted to ascertain whether R(−)-ketamine would block tolerance to effects of ethanol. Rats were given two high doses of ethanol on day 1 (2.3 and 1.7 mg/kg, intraperitoneally, i.p.). Rats were then tested on day 2 for the effects of ethanol of grip strength, and the results are shown in FIG. 9. Rats not given ethanol on day 1 showed a significant impairment in grip strength compared to those that did receive ethanol on day 1 (compare first and second bars at 30 min post dosing in FIG. 9). This demonstrates tolerance to this motor-impairing effect of ethanol. When pretreated with R-ketamine prior to ethanol on day 1, the tolerance was significantly lost (compare red bar vs. green bar@30 min post dosing).

The general methods of dosing and tested of Khanna et al. (1993) were followed. Two large doses of ethanol were given to rats on day 1 (2.3 and then 1.7 g/kg). The ethanol was given alone or in the presence of R-ketamine at various doses in different groups of rats. On day 2, ethanol alone was given (2.3 mg/kg, i.p.) and the rats were tested for grip strength by the methods of Popik et al. (2006).

The degree of myorelaxation was determined next using a grip strength meter (Columbus Instruments, Columbus, Ohio). The forepaws of a rat were placed on the metal mesh attached to the meter, and the body was gently pulled until the rat released the grid. Three measures of grip strength were taken sequentially for each rat, averaged, and corrected for body weight. Finally, rats were placed on a rod rotating at 6 rpm. Those animals that did not fall off the apparatus within 2 min were considered to have normal balance and coordination.

Tolerance, or a reduced reaction to a drug following repeated use, is a common effect of exposure to drugs of abuse. This diminishment of drug effect after prior drug exposure plays an important role in substance used disorders and drug dependence (Miller et al., 1987). Giving two high dose exposures of ethanol on day 1 produced tolerance to the effects of ethanol on day 2 in rats. This tolerance to the effect of ethanol on motor-impairment ($p<0.05$) was blocked by R-ketamine ($p<0.05$).

Example 7: R(−)-Ketamine does not Produce Anhedonia or Negative Affect

Treatment of drug addiction requires initiation of abstinence from the drug of abuse. In withdrawal from drugs of abuse, a host of physiological and behavioral effects arise that are opposite in nature to the effects produced by the drug. Thus, whereas the drug of abuse induces states of well-being and euphoria, abstinence results in anxiety, depression, anhedonia, negative affect, and drug craving (Deneau and Seevers, 1964). A substance abuse treatment that either dampened or did not exacerbate this psychophysiological state, would therefore be of value in substance abuse treatment (Huhn et al., 2016; Koob, 1992; Langdon et al., 2019). In contrast, a drug that increased anxiety, depression, and/or anhedonia or negative affect would be counter indicated (Koob et al., 1992; Langdon et al., 2019).

S(+)-ketamine induced an anhedonic or negative affective state in rats that was dose-dependent. This was modeled in rats by observing their response to the stimulation of reward-detecting nerve cells in brain in a model called intercranial self-administration or ICSS (Negus and Miller, 2014). In contrast, although R(−)-ketamine is more potent in rodents than S-ketamine, these same doses of R(−)-ketamine did not induce and anhedonic state. Likewise, in contrast to the drug of abuse cocaine, R(−)-ketamine did not shift the curve to the left suggesting a lack of abuse liability of R(−)-ketamine.

A study was conducted to assess the comparative effects of R-(−)-ketamine to that of S-ketamine in rats on intracranial self-stimulation. Intercranial self-stimulation (ICSS) is an assay system that detects 1) effects of abused drugs, and 2) side-effects of drugs (Negus and Miller, 2014).

Rats were implanted with electrodes directed at the rewarding brain area, the medial forebrain bundle, and were allowed to deliver current to this brain area by depressing a response lever. The effect of changing the current frequency on behavior alone (vehicle) and in the presence of drug was then observed.

Ten adult male Sprague-Dawley rats (Harlan, Indianapolis, Ind.) were individually housed in a temperature-controlled (20-22° C.) AAALAC-accredited facility in which they had controlled access to food (7012 Teklad LM-485 Mouse/Rat Sterilizable Diet; Harlan, Indianapolis, Ind.) to maintain a weight range of 380-420 g and ad libitum access to water. The rats were maintained on a 12 h/12 h light-dark cycle (0600-1800 lights on) for the duration of the experiment, and they were trained and tested during the light segment of this cycle. Rats (360-420 g at time of surgery) were anesthetized via isoflurane inhalation (~3%) and an electrode was implanted into the medial forebrain bundle according to the following stereotaxic coordinates: anteroposterior, −2.8 mm from bregma; lateral, 1.7 mm from the midline; ventrodorsal, −8.8 mm from skull (Paxinos & Watson, 2007).

Experimental sessions were conducted in commercially obtained operant conditioning chambers (ENV-007CT; Med Associates, Inc., Fairfax, Vt.) equipped with two retractable levers on the front intelligence panel, a stimulus lamp above each lever, and a 5-w house light. Test chambers were enclosed in sound-attenuating cubicles each equipped with a ventilation fan. A counterbalanced tether (Plastics One, Roanoke, Va.) that allowed free movement within the operant chamber connected the implanted electrode to an ICSS stimulator (PHM-152/2; Med Associates, Inc., St. Albans, Vt.). Control of stimuli and recording of data were arranged by computer-controlled software (MedPC IV; Med Associates, Inc., St. Albans, Vt.) interfaced with the operant test chambers.

One week after surgery, the rats began self-stimulation training. Initially, both left and right levers were extended, the house light illuminated, and each press of the right-side lever (i.e., Fixed Ratio 1, "FR1") resulted in the delivery of stimulation (100 µA, 158 Hz). Responses on the left lever were without programmed consequences. During the duration of the delivery of stimulation (500 ms), the house light was extinguished and the cue lights above each lever flashed at 3 Hz. Current intensity was individually adjusted when necessary to maintain stable maximal rates of behavior (>35 responses/min) at the highest frequency. This intensity level was held constant for the remainder of the experiment.

The frequency-rate procedure (modified from Carlezon & Wise, 1996) consisted of multiple response components, each composed of 10, 1-min FR1 reinforcement periods. During each 1-min reinforcement period, a single, scheduled frequency was available for delivery contingent upon FR1 responding on the right lever. Frequencies were progressively decreased in 0.05 log-increments from 158-56 Hz (i.e. 2.2-1.75 log Hz) during each component. Each 1-min reinforcement period was preceded by a 5-sec sample period during which five behaviorally non-contingent stimulations were delivered at the scheduled stimulation frequency. Each 1-min response period was followed by a 5-sec timeout (TO) period during which the house light was extinguished and ICSS was unavailable. Rats were trained daily (Monday through Friday) using the described procedure. Training sessions were conducted in the morning and consisted of three consecutive response components each containing 10 1-min FR1 reinforcement periods (i.e. 30 1-min FR1 response periods). Once stable behavior was established, as demonstrated by ≤10% variation in threshold (i.e. theta 0; T0) and M50 (see Data Analysis below) for three consecutive training days, rats began testing, and baseline stability was monitored throughout the course of the experiment. Threshold (T0) was defined as the theoretical frequency at which the linear portion of the frequency-rate curve intersects with the abscissa (i.e., zero responses). M50 was defined as the estimated frequency that supported half-maximal response rates.

On test days, two ICSS experimental sessions were conducted. During the baseline session, each rat was tested during three consecutive components identical to training days. After completing this baseline determination, rats were returned to their home cages and received intraperitoneal (i.p.) administration of either R(−)-ketamine (ATDP 33,988) (at 3, 10, or 30 mg/kg) or vehicle 2 hours prior to the test session. Rats were returned to operant chambers for the test session that consisted of two consecutive response components (i.e., 20 1-min FR1 response periods). R(−)-ketamine (ATDP 33,988) was administered in ascending dose order.

Subjects were tested up to twice weekly (typically Tuesdays and Fridays), with a minimum of 72 h between test sessions. Frequency-rate training sessions were conducted during the week on non-test days to maintain and monitor stability in frequency-rate responding, to determine testing eligibility, and to ensure drug washout. Rats were required to meet stability criteria (<10% variation in T0 and in M50 from the last baseline test session) in order to be scheduled for testing.

ATDP 33,988 (R(−)-ketamine) was provided by the National Institute on Drug Abuse (NIDA) and solubilized in sterile saline. The vehicle was sterilized by filtration through 0.2 μm filtration disks. All injections were administered i.p. 2 hours prior to the start of the test session at a volume equivalent to 1 ml/kg body weight.

The results shown here are from ten rats. Results from the initial daily response component during baseline sessions were excluded from data analysis as it has been shown that behavior is less stable during each initial daily component relative to subsequent components (Carlezon and Chartoff, 2007). Results obtained at each frequency during each of the two subsequent baseline components were averaged to determine a baseline response rate for each frequency. Maximum control response rate (MCR) was then defined by the maximum individual baseline response rate that occurred across all frequencies during the baseline session for each rat independently. For subsequent data analyses, baseline and test stimulation rates were normalized to each rat's daily baseline MCR to produce percent maximum control rate (% MCR). These values were calculated by dividing the mean number of responses obtained at each frequency by the rat's maximum rate at any frequency determined during the associated (i.e., the same day's) baseline session, and then finally multiplying this quotient by 100 for both baseline and test sessions.

Figure 10:
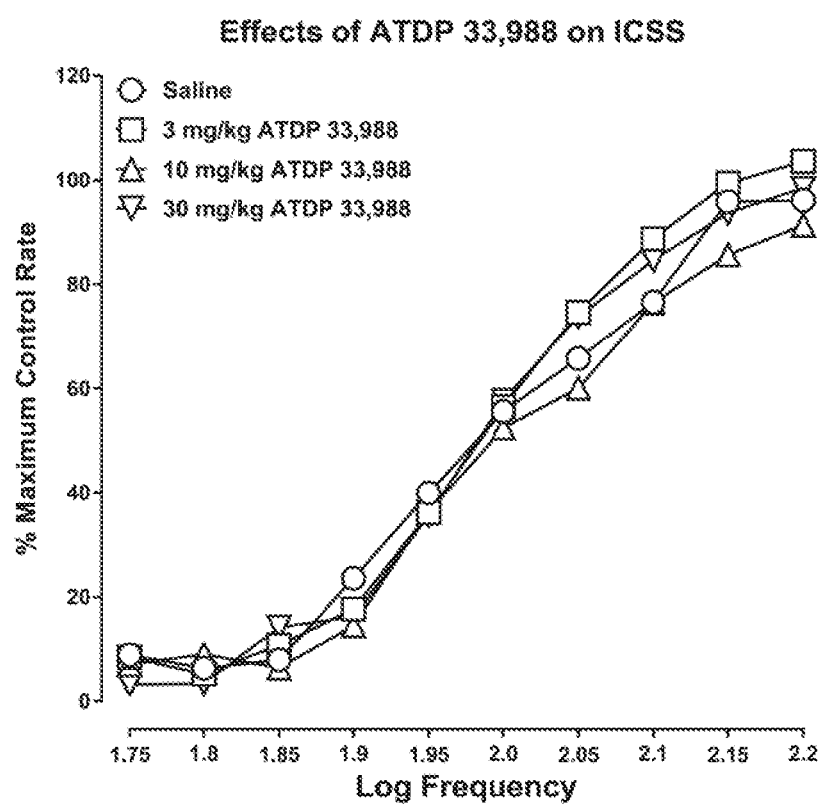
FIG. 10 is a plot showing the frequency-rate response curves for the effects of R(−)-ketamine and vehicle on intracranial self-stimulation (ICSS), and that R(−)-ketamine does not alter the intercranial self-stimulation function. ATDP 33,988=R(−)-ketamine. Frequency-rate responses rates for 1 mg/kg, 10 mg/kg and 30 mg/kg of R(−)-ketamine and saline vehicle are shown. Values represent the mean normalized response rate (% of maximum control responding) across 10 frequency presentations (1.75-2.20 log/Hz). Error bars are omitted for clarity due to overlapping treatment effects. There were no significant differences relative to vehicle produced by any dose of R(−)-ketamine.

Frequency-rate response data were analyzed using two-way (treatment×frequency) repeated measures ANOVA, and significant interactions were followed by Holm-Šidak multiple comparisons tests to identify treatment-related differences in responding by frequency (FIG. 10). For all analyses, vehicle (saline) served as the comparison condition. Leftward or upward shifts in the frequency-rate curve are inferred to be indicative of reward facilitation, and rightward or downward shifts in the frequency-rate curve of reward attenuation. Upward (rate increasing) or downward (rate decreasing) shifts in the frequency-rate curve at maximum response rates may be indicative of nonspecific motoric effects.

Figure 11:
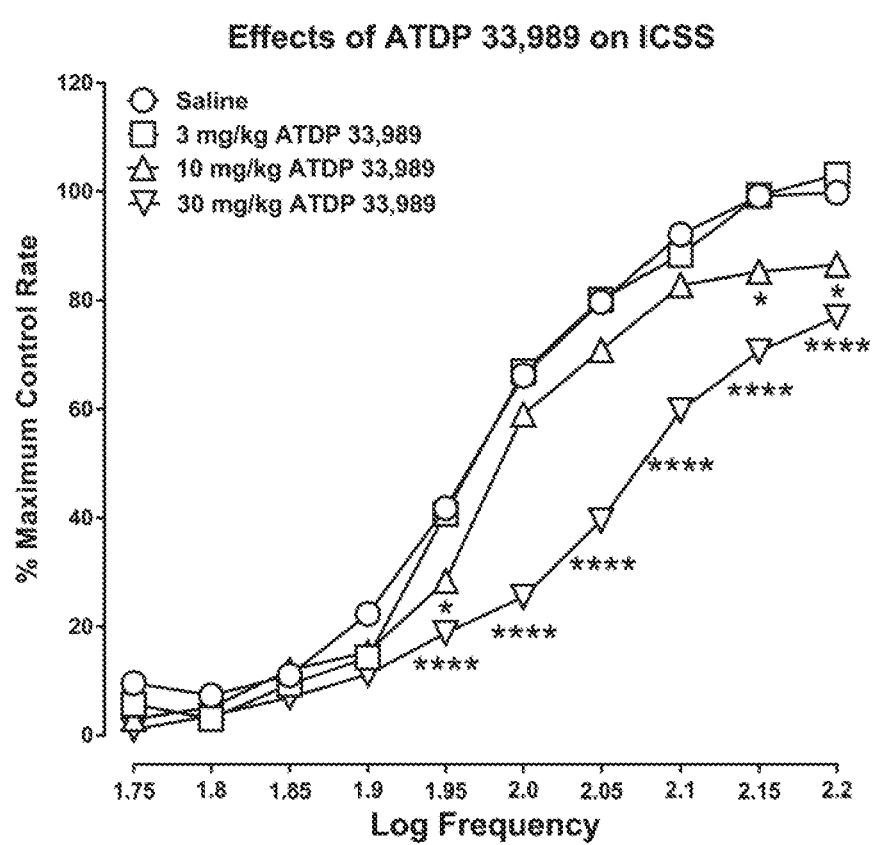
FIG. 11 is a plot showing the frequency-rate response curves for the effects of S(+)-ketamine and vehicle, and that S(+)-ketamine shifts the intercranial self-stimulation curve to the right suggesting that it produces an anhedonic and negative affect response. ATDP 33,989=S(+)-ketamine. Frequency-rate responses for 1 mg/kg, 10 mg/kg and 30 mg/kg of S(+)-ketamine and saline vehicle are shown. Values represent the mean normalized response rate (% of maximum control responding) across 10 frequency presentations (1.75-2.20 log/Hz). Error bars are omitted for clarity. Significant differences compared to vehicle at the respective frequencies are denoted by asterisks (*$p<0.05$: ****$p<0.0001$).

In addition to frequency-rate response curves, additional summary dependent measures were calculated and analyzed. Threshold (T0) is the theoretical frequency at which the linear portion of the frequency-rate curve intersects with the abscissa (i.e., zero responses). M50 is the estimated frequency that supports half-maximal responding (i.e., 50%). Linear regression analysis was used to calculate T0 and M50 raw frequencies for each rat during each condition and those values were normalized to each rat's individual baseline values (percent baseline T0 and M50) and were analyzed using repeated measures ANOVA. Multiple comparisons were conducted using Fisher's LSD test (FIG. 11). In addition, log transformations of T0 and M50 values were subsequently calculated using linear regression for each condition and analyzed using separate one-way repeated measures ANOVA for baselines and tests. Multiple comparisons were made using Fisher's LSD test to compare all doses to vehicle control (Tables 5-10 below). All statistical tests were conducted using microcomputer software (Prism 7.04, GraphPad Software, Inc., San Diego, Calif.), and all types of comparisons were considered statistically significant if $p<0.05$.

TABLE 5

Summary data for ATDP 33,988 (R(−)-ketamine)
Summary Data - ATDP 33,988

| Threshold ($T_0$) | Baseline | Test | N |
|---|---|---|---|
| Vehicle | 1.89 (0.03) | 1.90 (0.03) | 10 |
| 3 mg/kg ATDP 33,988 | 1.91 (0.02) | 1.88 (0.02) | 10 |
| 10 mg/kg ATDP 33,988 | 1.91 (0.03) | 1.93 (0.03) | 10 |
| 30 mg/kg ATDP 33,988 | 1.89 (0.02) | 1.90 (0.02) | 10 |

Summary table of log threshold $T_0$ values in rats tested with ATDP 33,988 (3, 10 and 30 mg/kg) or vehicle. Data represent the mean log $T_0$ frequency (log/Hz)+/−SEM of 10 rats. There were no significant differences between baseline or test log $T_0$ values compared to the respective vehicle baseline or test log $T_0$.

TABLE 6

Summary data for ATDP 33,988 (R(−)-ketamine

| $M_{50}$ | Baseline | Test | N |
|---|---|---|---|
| Vehicle | 2.00 (0.02) | 1.99 (0.02) | 10 |
| 3 mg/kg ATDP 33,988 | 2.00 (0.02) | 1.98 (0.01) | 10 |
| 10 mg/kg ATDP 33,988 | 2.00 (0.02) | 2.02 (0.02) | 10 |
| 30 mg/kg ATDP 33,988 | 1.98 (0.02) | 1.99 (0.02) | 10 |

Summary table of frequencies that sustained half-maximal responding (M50) in rats tested with ATDP 33,988 (3, 10 and 30 mg/kg) or vehicle. Data represent the mean log $M_{50}$ frequency (log/Hz)+/−SEM of 10 rats. There were no significant differences between baseline or test log $M_{50}$ values compared to the respective vehicle baseline or test log $M_{50}$.

TABLE 7

Summary data for ATDP 33,989 (S(+)-ketamine)
Summary Data - ATDP 33,989

| Threshold ($T_0$) | Baseline | Test | N |
|---|---|---|---|
| Vehicle | 1.85 (0.02) | 1.85 (0.02) | 10 |
| 3 mg/kg ATDP 33,989 | 1.86 (0.02) | 1.88 (0.01) | 10 |
| 10 mg/kg ATDP 33,989 | 1.87 (0.02) | 1.90 (0.02)* | 10 |
| 30 mg/kg ATDP 33,989 | 1.87 (0.02) | 1.95 (0.03)*** | 10 |

Summary table of log threshold $T_0$ values in rats tested with ATDP 33,989 (3, 10 and 30 mg/kg) or vehicle. Data represent the mean log $T_0$ frequency (log/Hz)+/−SEM of 10 rats. Significant differences between test threshold values compared to vehicle are denoted by asterisks (*p<0.05; ***p<0.001). There were no significant differences between baseline $T_0$ values following ATDP 33,989 treatment compared to vehicle baseline $T_0$.

TABLE 8

Summary data for ATDP 33,989 (S(+)-ketamine)

| $M_{50}$ | Baseline | Test | N |
|---|---|---|---|
| Vehicle | 1.97 (0.01) | 1.97 (0.01) | 10 |
| 3 mg/kg ATDP 33,989 | 1.97 (0.02) | 1.98 (0.01) | 10 |
| 15 mg/kg ATDP 33,989 | 1.97 (0.01) | 2.00 (0.03) | 10 |
| 30 mg/kg ATDP 33,989 | 1.98 (0.01) | 2.07 (0.03)**** | 10 |

Summary table of frequencies that sustained half-maximal responding ($M_{50}$) in rats tested with ATDP 33,988 (3, 10 and 30 mg/kg) or vehicle. Data represent the mean log $M_{50}$ frequency (log/Hz)+/−SEM of 10 rats. Significant differences between test threshold values compared to vehicle are denoted by asterisks (****p<0.0001). There were no significant differences between baseline $M_{50}$ values following ATDP 33,989 treatment compared to vehicle baseline $M_{50}$.

TABLE 9

Summary data for ATDP 33,990 (R-hydroxynorketamine)
Summary Data - ATDP 33,990

| Threshold ($T_0$) | Baseline | Test | N |
|---|---|---|---|
| Vehicle | 1.89 (0.02) | 1.87 (0.03) | 10 |
| 3 mg/kg ATDP 33,990 | 1.89 (0.02) | 1.92 (0.02) | 10 |
| 10 mg/kg ATDP 33,990 | 1.89 (0.02) | 1.90 (0.02) | 10 |
| 30 mg/kg ATDP 33,990 | 1.90 (0.02) | 1.91 (0.03) | 10 |

Summary table of log threshold $T_0$ values in rats tested with ATDP 33,990 (3, 10 and 30 mg/kg) or vehicle. Data represent the mean log $T_0$ frequency (log/Hz)+/−SEM of 10 rats. There were no significant differences between baseline or test log $T_0$ values compared to the respective vehicle baseline or test log $T_0$.

TABLE 10

Summary data for ATDP 33,990 (R-hydroxynorketamine)

| $M_{50}$ | Baseline | Test | N |
|---|---|---|---|
| Vehicle | 1.99 (0.01) | 1.99 (0.02) | 10 |
| 3 mg/kg ATDP 33,990 | 2.00 (0.02) | 2.00 (0.01) | 10 |
| 10 mg/kg ATDP 33,990 | 1.98 (0.01) | 2.00 (0.01) | 10 |
| 30 mg/kg ATDP 33,990 | 1.99 (0.02) | 1.99 (0.02) | 10 |

Summary table of frequencies that sustained half-maximal responding ($M_{50}$) in rats tested with ATDP 33,990 (3, 10 and 30 mg/kg) or vehicle. Data represent the mean log $M_{50}$ frequency (log/Hz)+/−SEM of 10 rats. There were no significant differences between baseline or test log $M_{50}$ values compared to the respective vehicle baseline or test log $M_{50}$.

Treatment of drug addiction requires initiation of abstinence from the drug of abuse. In withdrawal from drugs of abuse, a host of physiological and behavioral effects arise that are opposite in nature to the effects produced by the drug. Thus, whereas the drug of abuse induces states of well-being and euphoria, abstinence results in anxiety, depression, anhedonia, negative affect and drug craving (Deneau and Seevers, 1964). A substance abuse treatment that either dampened or did not exacerbate this psychophysiological state, would therefore be of value in substance abuse treatment (Huhn et al., 2016; Koob, 1992; Langdon et al., 2019). In contrast, a drug that increased anxiety, depression, and/or anhedonia or negative affect would be counter indicated (Koob et al., 1992; Langdon et al., 2019).

S(+)-ketamine induced an anhedonic state in rats that was dose-dependent. This was modeled in rats by observing their response to the stimulation of reward-detecting nerve cells in brain in a model called intercranial self-administration or ICSS (Negus and Miller, 2014). In contrast, although R(−)-ketamine is more potent in rodents than S(+)-ketamine, these same doses of R(−)-ketamine did not induce and anhedonic state. Likewise, in contrast to the drug of abuse cocaine, R(−)-ketamine did not shift the ICSS curve to the left suggesting a lack of abuse liability of R(−)-ketamine.

Racemic ketamine can produce psychotomimetic effects, dysphoria, and motor-impairing effects in humans (Rowland, 2005; Cooper et al., 2017; Ke et al., 2018; Liu et al., 2016) and these effects can be modeled in rodents (e.g., Ginski and Witkin, 1994). The effects of S(+)-ketamine shown in FIG. 11 likely represent the impact of side-effects of S(+)-ketamine, which were not observed with R(−)-ketamine (FIG. 10). These comparative data are consistent with recent reports that R(−)-ketamine displays are more benign side-effect profile than S-ketamine (c.f., Yang et al., 2015).

The dysphoria/anhedonia or negative affect seen with S(+)-ketamine was not observed with R(−)-ketamine. These data show that R(−)-ketamine, but not S(+)-ketamine would be a viable treatment for substance use disorders given its lack of induction of anhedonia or negative affect/dysphoria.

Figure 12:
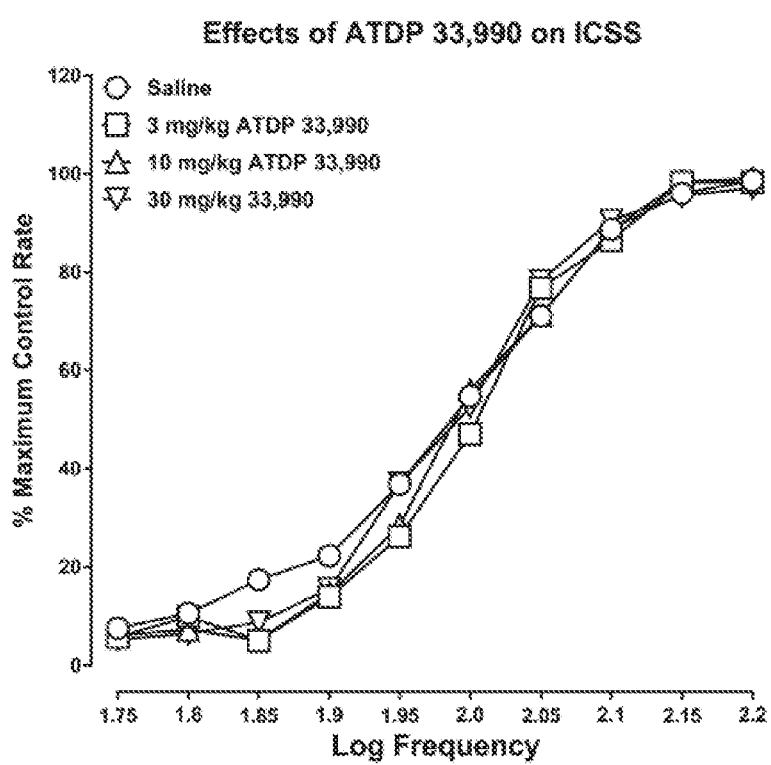
FIG. 12 is a plot showing the frequency-rate response curves for the effects of R-hydroxynorketamine and vehicle, and that the metabolite of R(−)-ketamine, R-hydroxy-norketamine, like R(−)-ketamine, does not influence the intercranial self-stimulation behavior of rats. ATDP 33,990=R-hydroxynorketamine. Frequency-rate responses for 1 mg/kg, 10 mg/kg and 30 mg/kg of R-hydroxynorketamine and saline vehicle are shown. Values represent the mean normalized response rate (% of maximum control responding) across 10 frequency presentations (1.75-2.20 log/Hz). Error bars are omitted for clarity due to overlapping treatment effects. There were no significant differences relative to the vehicle condition with any dose of R-hydroxynorketamine.
Figure 13:
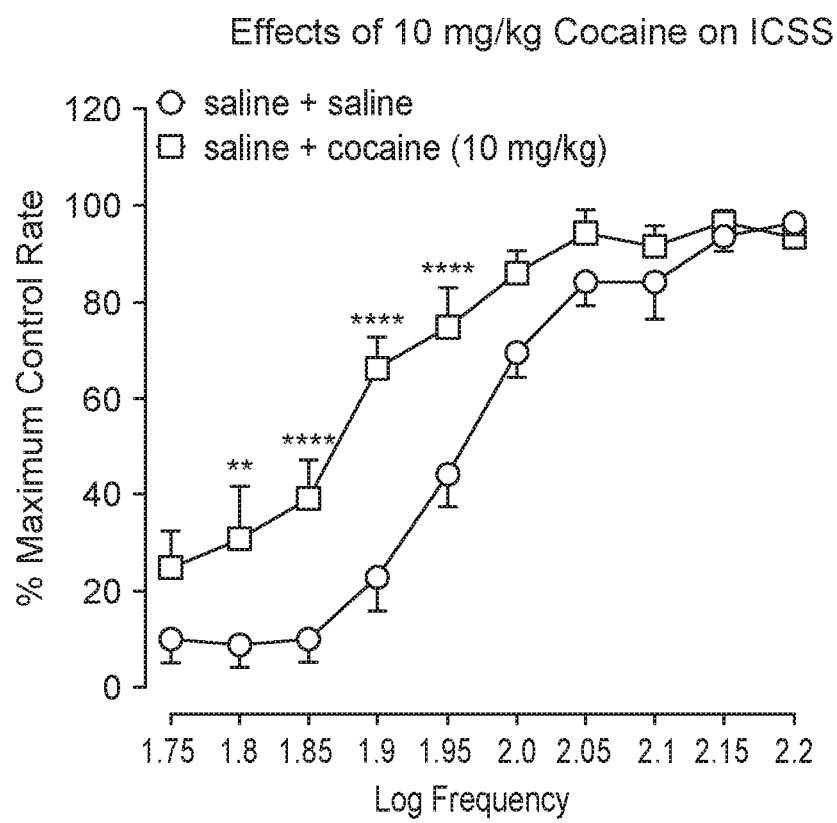
FIG. 13 is a plot showing the effects of cocaine on ICSS in rats. Cocaine (10 mg/kg) shifts the frequency curve to the left. R(−)-ketamine does not.

Under ICSS conditions in rats, R(−)-ketamine did not significantly alter behavior of rats (FIG. 10). In contrast, S(+)-ketamine produced a significant downward shift in the stimulation-frequency curve (FIG. 11). Likewise, the metabolite of R-ketamine, R-hydroxy-norketamine did not alter the frequency-response function (FIG. 12). These findings with S-ketamine are distinct from those arising with of some drugs of abuse (e.g., cocaine, FIG. 13), as has been reported previously (c.f., Negus and Miller, 2014). In FIG. 10, R(−)-ketamine does not alter the intercranial self-stimulation function. In contrast, S(+)-ketamine (FIG. 11) shifts the curve to the right, indicating that it produces an anhedonic response. Comparing the data in FIG. 10 to FIG. 11 indicates that S(+)-ketamine produces effects in rats that are behaviorally impairing, an effect not observed with R(−)-ketamine. An anhedonic response is counter-indicated for a medication for substance use disorders. Similarly, FIG. 12 shows that the metabolite of R(−)-ketamine, R-hydroxy-norketamine, like R(−)-ketamine, does not influence the intercranial self-stimulation behavior of rats. Thus, neither R(−)-ketamine or its hydroxy nor metabolite induce an anhedonic state like that of S(+)-ketamine.

Example 8: Comparative Pharmacology of Ketamine, S(+)-Ketamine and R(−)-Ketamine The pharmacology of ketamine, S(+)-ketamine, and R(−)-ketamine in models used to predict efficacy and/or side-effects of medications for substance use disorders was compared. Overall, R(−)-ketamine was about equipotent to racemic R,S-ketamine.

R(−)-ketamine is 2-4 fold less potent at the receptor (NMDA) than S(+)-ketamine. if effects are observed at similar doses in R(−)-ketamine and racemic ketamine, this by definition means that R(−)-ketamine will have a safety advantage since dissociation, and likely abuse potential, are dose related. Effects at similar doses indicate that R(−)-ketamine has a superior safety profile important in the substance use disorder population. Moreover, this safety advantage is not be expected since ketamine is known to work via the NMDA receptor in terms of any direct effect generally (with a host of receptors possibly involved but of unknown relevance). Therefore R(−)-ketamine would be expected like in pain to only work if a subject received more R(−)-ketamine compared S(+)-ketamine or the racemate to achieve an effect.

The potencies of R(−)-ketamine in table 11 were not predicted from other potency data. The comparison R(−)-ketamine, S(+)-ketamine and racemic ketamine from the current disclosure to previous studies are summarized in Table 11 below. Values are doses in mg/kg.

Plasma S(+)-ketamine concentration after intravenous (i.v.) R,S-ketamine administration in pain patients was also correlated with subjective reports of undesirable effects (From Persson et al., 1998, see FIG. 3).

R(−)-ketamine is less potent than S(+)-ketamine or R,S-ketamine. These potency estimates did not predict potency in substance use assays in Table 11 above.

INDUSTRIAL APPLICABILITY

As described above, the agents and pharmaceutical compositions for prevention and/or treatment of a substance use disorder according to the present disclosure have rapid and long-lasting antidepressant effects and less side effects such as psychotomimetic effects, and hence are useful as novel pharmaceuticals in the field of prevention and/or treatment of a number of substance use disorders, some of which exhibit depressive symptoms.

TABLE 11

Comparative Pharmacology of ketamine, S(+)-ketamine, and R(−)-ketamine in models used to predict efficacy and/or side-effects of medications for substance use disorders.

| Model | +/−Ketamine | S-Ketamine | R-Ketamine | Reference |
|---|---|---|---|---|
| Morphine CPP | 10 | 10 | 10 | Present study |
|  |  |  |  | Suzuki et al., 2000 |
| Morphine Withdrawal | 8, 16 | 10, 20 | 10, 20 | Present study |
|  | 25 |  |  | Ji et al., 2004 |
|  | 1 |  |  | Fidecka et al., 1987 |
|  |  |  |  | Koyuncuoğlu et al., 1990 |
| Ethanol Tolerance | 1 - tilt-plane test |  | 3 - grip strength | Present study |
|  |  |  |  | Khanna et al., 1993 |
| ICSS | 5.6, 10 anhedonia | 10, 30 anhedonia | 10, 30 - no anhedonia | Present study |
|  |  |  |  | Hillhouse et al., 2014 |

Morphine CPP: conditioned place preference—this test measures the ability of racemic, S(+)-ketamine or R(−)-ketamine to block the rewarding effects of morphine
Morphine withdrawal: this test measures the ability of racemic, S(+)-ketamine or R(−)-ketamine to attenuate withdrawal symptoms in patients
Ethanol tolerance: this test measures the ability of racemic, S(+)-ketamine or R(−)-ketamine to block the development of drug tolerance, a phenomenon associated with drug dependence
ICSS: inter-cranial self-stimulation—this test measures rewarding drug effects and anhedonia or negative affect of racemic, S(+)-ketamine or R(−)-ketamine.

Racemic ketamine, S(+)-ketamine and R(−)-ketamine were also compared when used against drugs of substance use disorders in several model systems. The comparative pharmacology of racemic ketamine, S(+)-ketamine and R(−)-ketamine is shown in Table 12 below:

What is claimed is:

1. A method of treating alcohol abuse in a subject, comprising administering to the subject a therapeutically effective amount of a composition comprising R(−)-ketamine or a pharmaceutically acceptable salt thereof, wherein the composition is substantially free of S(+)-ketamine or a pharmaceutically acceptable salt thereof.

2. The method of claim 1, wherein the therapeutically effective amount of the composition comprising R(−)-ketamine does not cause anhedonia or negative affect in the subject.

3. The method of claim 1, wherein administering the composition to the subject reduces a symptom of withdrawal or prevents a relapse of the alcohol abuse in the subject, reduces tolerance to alcohol, reduces dependence on alcohol, improves adherence to a treatment for alcohol abuse, reduces a preference for alcohol, decreases liking for alcohol, or increases abstinence from alcohol.

TABLE 12

Comparison of Racemic ketamine and its isomers in substance use disorders

| Model | +/− Ketamine | S-Ketamine | R-Ketamine | Reference |
|---|---|---|---|---|
| Morphine Seizures[a] | 0.3 | 0.03 | 0.3 | Kolesnikov et al., 1997 |
| Pain control[b] | 0.15, 0.3, 0.45 | Plasma levels of S analyzed (50-400 ng/ml) | | Persson et al., 1998 |
| Unconsciousness[c] | 275 ± 25 | 140 ± 21 | 429 ± 37 | White et al., 1985 |

Values are doses in mg/kg
[a]Not blocked by naloxone
[b]Chronic pain patients
[c]IV ketamine and isomers given - doses that produced equivalent unconsciousness are shown 4. The method of claim 1, wherein the method further comprises an additional pharmacotherapy for alcohol abuse.

5. The method of claim 4, wherein the additional pharmacotherapy comprises a gradually reducing regimen, a substitution therapy or a medication assisted treatment.

6. The method of claim 4, wherein the method further comprises a behavioral therapy.

7. The method of claim 5, wherein the medication assisted treatment comprises Disulfiram, Acamprosate or Naltrexone.

8. The method of claim 4, wherein the composition is administered prior to the additional therapy, at the same time as the additional therapy, or after the additional therapy.

9. The method of claim 1, wherein the composition is administered every day, every 2 days, every 3 days, every 4 days, every 7 days, every 10 days, every 14 days or every 30 days.

10. The method of claim 1, wherein composition further comprises a pharmaceutically acceptable carrier.

11. The method of claim 10, wherein the composition comprises about 0.01 mg to about 500 mg, about 0.1 mg to about 500 mg, or about 0.1 mg to about 100 mg, of R(−)-ketamine or a pharmaceutically acceptable salt thereof.

12. The method of claim 10, wherein the pharmaceutically acceptable salt of R(−)-ketamine is R(−)-ketamine hydrochloride.

13. The method of claim 10, wherein the composition is formulated for intravenous, intramuscular, sublingual, subcutaneous, transnasal, oral, rectal or transdermal administration.

14. The method of claim 1, wherein administering to the subject a therapeutically effective amount of a composition comprising R(−)-ketamine reduces tolerance to alcohol in the subject.

15. A method of treating at least one withdrawal symptom of alcohol abuse in a subject, comprising administering to the subject a therapeutically effective amount of a composition comprising R(−)-ketamine or a pharmaceutically acceptable salt thereof, wherein the composition is substantially free of S(+)-ketamine or a pharmaceutically acceptable salt thereof.

16. The method of claim 15, wherein the at least one withdrawal symptom of alcohol abuse comprises a physical symptom of withdrawal, a psychological symptom of withdrawal or a combination thereof.

17. The method of claim 16, wherein the physical symptom of withdrawal comprises tremors, insomnia, disturbed sleep, headache, sweating, nausea, vomiting, muscle pain, muscle stiffness, hypertension, irregular heart rate, elevated heart rate, heart palpitations, dizziness, shakiness, tremors, seizures, dehydration, shallow breathing, fatigue, loss of appetite, clammy skin, loss of color or a combination thereof.

18. The method of claim 16, wherein the psychological symptom of withdrawal comprises anxiety, irritability, difficulty concentrating, difficulty thinking clearly, mood swings, nightmares, depression, tension, panic attacks, short term memory loss, restlessness, a feeling of helplessness, stress-sensitivity, a heightened responsivity to substance-related cues, aberrant reward processing, a substance craving or a combination thereof.

19. A method of treating a psychological symptom associated with alcohol abuse in a subject, comprising administering to the subject a therapeutically effective amount of a composition comprising R(−)-ketamine or a pharmaceutically acceptable salt thereof, wherein the composition is substantially free of S(+)-ketamine or a pharmaceutically acceptable salt thereof.

* * * * *